(12) United States Patent
Lesburg et al.

(10) Patent No.: US 6,434,489 B1
(45) Date of Patent: Aug. 13, 2002

(54) COMPOSITIONS OF HEPATITIS C VIRUS NS5B POLYMERASE AND METHODS FOR CRYSTALLIZING SAME

(75) Inventors: Charles A. Lesburg, Weehawken; Michael Cable, Freehold, both of NJ (US); Zhi Hong, Nanuet, NY (US); Anthony F. Mannarino, North Plainfield, NJ (US); Patricia C. Weber, Yardley, PA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/541,990

(22) Filed: Apr. 3, 2000

(51) Int. Cl.[7] .......................... G01N 33/48; G01N 33/50; C12N 9/00
(52) U.S. Cl. .......................... 702/19; 702/27; 435/69.1; 435/183; 514/12
(58) Field of Search ................................. 435/69.1, 183, 435/320.1, 325; 830/350; 514/12; 702/19, 27

(56) References Cited

PUBLICATIONS

Abrahams and Leslie, "Methods used in the structure determination of bovine mitochondrial $F_1$ ATPase", *Acta Crystallogr*, D52:30–42 (1996).
Ago et al., "Crystal structure of the RNA–dependent RNA polymerase of hepatitis C virus", *Structure*, 7:1417–1426 (1999).
Alter and Mast, "The epidemiology of viral hepatitis in the United States", *Gastroenterol Clin North Am*, 23:437–455 (1994).
Bartenschlager et al., "Nonstructural protein 3 of the hepatitis C virus encodes a serine–type proteinase required for cleavage at the NS3/4 and NS4/5 junctions", *J Virol*, 67:3835–3844 (1993).
Bressanelli et al., "Crystal structure of the RNA–dependent RNA polymerase of hepatitis C virus" *Proc Natl Acad Sci USA*, 96:13034–13039 (1999).
Brünger et al., "Slow–cooling protocols for crystallographic refinement by simulated annealing", *Acta Crystallogr*, A46:585–593 (1990).
Choo et al., "Isolation of a cDNA clone derived from a blood–borne non–A, non–B viral hepatitis genome", *Science*, 244:359–362 (1989).
Choo et al. "Genetic organization and diversity of the hepatitis C virus", *Proc Natl Acad Sci USA*, 88:2451–2455 (1991).
de la Fortelle and Bricogne, "Maximum–likelihood heavy–atom parameter refinement for multiple isomorphous replacement and multiwavelength anomalous diffraction methods", *Methods Enzymol*, 276:472–494 (1996).
Doublié, "Preparation of selenomethionyl proteins for phase determination", *Methods Enzymol*, 276:523–530 (1997).

Doublié et al., "Crystal structure of a bacteriophage T7 DNA replication complex at 2.2 A resolution", *Nature*, 391:251–258 (1998).
Ferrari et al., "Characterization of soluble hepatitis C virus RNA–dependent RNA polymerase expressed in *Escherichia coli*", *J Virol*, 73:1649–1654 (1999).
French and Wilson, "On the treatment of negative intesity observations", *Acta Crystallogr*, A34:517–525 (1978).
Grakoui et al., "Characterization of the hepatitis C virus–encoded serine proteinase: determination of proteinase–dependent polyprotein cleavage sites", *J Virol*, 67:2832–2843 (1993).
Grakoui et al., "Expression and identification of hepatitis C virus polyprotein cleavage products", *J Virol*, 67:1385–1395 (1993).
Hansen et al., "Structure of the RNA–dependent RNA polymerase of poliovirus", *Structure*, 5:1109–1122 (1997).
Hendrickson and Ogata, "Phase determination from multiwavelength anomalous diffraction measurements", *Methods Enzymol*, 276:494–523 (1997).
Hooft et al., "Errors in protein structures", *Nature*, 381:272 (1996).
Huang et al., "Structure of a covalently trapped catalytic complex of HIV–1 reverse transcriptase: implications for drug resistance", *Science*, 282:1669–1675 (1998).
Iwarson, "The natural course of chronic hepatitis C ", *FEMS Microbiol Rev*, 14:201–204 (1994).
Jacobo–Molina et al., "Crystal structure of human immunodeficiency virus type 1 reverse transcriptase complexed with double–stranded DNA at 3.0 A resolution shows bent DNA", *Proc Natl Acad Sci USA*, 90:6320–6324 (1993).
Jones et al., "Improved methods for building protein models in electron density maps and the location of errors in these models", *Acta Crystallogr*, A47:110–119 (1991).
Joyce and Steitz, "Function and structure relationships in DNA polymerases", *Ann Rev Biochem*, 63:777–822 (1994).
Karplus et al., "Molecular dynamics: applications to proteins", *Cold Spring Harb Symp Quant Bio*, 52:381–390 (1987).
Kato et al., "Molecular cloning of the human hepatitis C virus genone from Japanese patients with non–A, non–B hepatitis", *Proc Natl Acad Sci USA*, 87:9524–9528 (1990).
Kew, "Hepatitis C virus and hepatocellular carcinoma", *FEMS Microbiol Rev*, 14:211–219 (1994).

(List continued on next page.)

Primary Examiner—Marianne P. Allen
(74) Attorney, Agent, or Firm—Darrell Fontenot

(57) ABSTRACT

The invention relates to the purification, crystallization of and structure of hepatitis C virus (HCV) NS5B RNA-dependent RNA polymerase. Also, crystallization conditions for NS5B are provided. Further, the atomic coordinates for the NS5B protein are disclosed. Examples of its use for the determination of the three-dimensional atomic structures of HCV NS5B or HCV NS5B in complex with substrates or substrate analogs or inhibitors are also provided.

38 Claims, 1 Drawing Sheet

PUBLICATIONS

Kiefer et al., "Visualizing DNA replication in a catalytically active Bacillus DNA polymerase crystal", *Nature*, 391:304–307 (1998).

Kleywegt and Brünger, "Checking your imagination: applications of the free R value", *Structure*, 4:897–904 (1996).

Kleywegt and Jones, "Where freedom is given, liberties are taken", *Structure*, 3:535–540 (1995).

Kraulis, "Molscript: a program to produce both detailed and schematic plots of protein structures", *J Appl Crystallogr*, 24:946–950 (1991).

Kuo et al., "An assay for circulating antibodies to a major etiologic virus of human non–A, non–B hepatitis", *Science*, 244:362–364 (1989).

Laskowski et al., "Procheck: a program to check the stereochemical quality of protein structures", *J Appl Crystallogr*, 26:283–291 (1993).

Lesburg et al., "Crystal structure of the RNA–dependent RNA polymerase from hepatitis C virus reveals a fully encircled active site", *Nat Struct Biol*, 6:937–943 (1999).

Matthews, "Solvent content of protein crystals", *J Mol Biol*, 33:491–497 (1968).

Merritt and Bacon, "Raster3D: Photorealistic molecular graphics", *Methods Enzymol*, 276:505–524 (1997).

Miller et al., "SnB; Crystal structure determination via shake–and–bake", *J Appl Crystallogr*, 27:613–621 (1994).

Otwinowshi and Minor, "Processing of X–ray diffraction data collected in oscillation mode", *Methods Enzymol*, 276:307–326(1997).

Pelletier et al., "Structures of ternary complexes of rat DNA polymerase beta, a DNA template–primer, and ddCTP", *Science*, 264:1891–1903 (1994).

Poch et al., "Identification of four conserved motifs among the RNA–dependent polymerase encoding elements", *EMBO J*, 8:3867–3874 (1984).

Purcell, "Hepatitis C virus: historical perspective and current concepts", *FEMS Microbiol Rev*, 14:181–191 (1994).

Saito et al., "Hepatitis C virus infection is associated with the development of hepatocellular carcinoma", *Proc Natl Acad Sci USA*, 87:6547–6549 (1990).

Simons et al., "Identification of two flavivirus–like genomes in the GB hepatitis agent", *Proc Natl Acad Sci USA*, 92:3401–3405 (1995).

Sousa, "Structural and mechanistic relationships between nucleic acid polymerases", *Trends Biochem Sci*, 21:186–190 (1996).

Takamizawa et al., "Structure and organization of the hepatitis C virus genome isolated from human carriers", *J Virol*, 65:1105–1113 (1991).

Tomei et al., "NS3 is a serine protease required for processing of hepatitis C virus polyprotein", *J Virol*, 67:4017–4026 (1993).

van der Poel, "Hepatitis C virus", *Curr Stud Hematol Blood Transf*, 61:137–163 (1994).

Weber, "Physical principles of protein crystallization", *Adv Protein Chem*, 41:1–36 (1991).

US 6,434,489 B1

COMPOSITIONS OF HEPATITIS C VIRUS NS5B POLYMERASE AND METHODS FOR CRYSTALLIZING SAME

FIELD OF THE INVENTION

The present invention relates to compositions and crystals of a hepatitis C virus RNA dependent RNA polymerase called NS5B and to methods of producing such crystals. This invention relates to methods of using the structure coordinates of hepatitis C virus NS5B to solve the structure of homologous NS5B proteins or complexes containing the NS5B protein.

BACKGROUND OF THE INVENTION

Infection by hepatitis C virus (HCV) is a compelling human medical problem. HCV is recognized as the causative agent for most cases of non-A and non-B hepatitis, with an estimated human seroprevalence of 1% globally [Choo, et al., Science, 244:359–362 (1989); Kuo, et al., Science, 244:362–364 (1989); Purcell, FEMS Microbiology Reviews; 14:181–191 (1994); Van der Poel. Current Studies in Hematology and Blood Transfusion, H. W. Reesink, Ed., (Basel: Karger), pp. 137–163 (1994)]. Four million individuals may be infected in the United States alone [Alter, and Mast, Gastroenterol. Clin. North Am., 23:437–455 (1994)].

Upon first exposure to HCV, only about 20% of infected individuals develop acute hepatitis and appear to resolve the infection spontaneously. In the most instances (~80%), however, the virus establishes a chronic infection that persists for decades [Iwarson, FEMS Microbiology Reviews, 14: 201–204 (1994)]. This usually results in recurrent and progressively worsening liver inflammation, which often leads to more severe disease states such as cirrhosis and hepatocellular carcinoma [Kew, FEMS Microbiology Reviews, 14: 211–219 (1994); Saito, et al., Proc. Natl. Acad. Sci. USA 87: 6547–6549 (1990)].

The HCV genome encodes a polyprotein of approximately 3000 amino acids [Choo, et al. Proc. Natl. Acad. Sci. USA, 88: 2451–2455 (1991); Kato, et al., Proc. Natl. Acad. Sci. USA, 87: 9524–9528 (1990); Takamizawa, et al., J. Virol., 65:1105–113 (1991)]. The HCV non-structural (NS) proteins provide catalytic machinery for viral replication. The NS proteins are derived by proteolytic cleavage of the polyprotein [Bartenschlager, et al., J. Virol., 67: 3835–3844 (1993); Grakoui, et al., J. Virol, 67: 2832–2843 (1993); Grakoui, et al., J. Virol., 67:1385–1395 (1993); Tomei, et al., J. Virol., 67:4017–4026 (1993)].

Until recently, the only therapy available for treating chronic HCV infection was interferon-α (IFN-α). However, not all patients are responsive to IFN-α treatment. While combination therapy of IFN-α and ribavirin has significantly improved the clinical outcome, a need exists for more effective methods of treatment.

The NS5B RNA dependent RNA polymerase is considered a valuable target for antiviral agents. However, drug discovery efforts directed towards the NS5B protein have been hampered by the lack of structural information about NS5B. Such structural information would provide valuable information for discovery of HCV NS5B polymerase inhibitors. However, efforts to determine the structure of HCV NS5B polymerase have been hampered by difficulties in obtaining sufficient quantities of pure active enzyme and by poor solubility of the enzyme. There have been no crystals reported of any NS5B polymerase polypeptide. Thus, x-ray crystallographic analysis of such proteins has not previously been available.

SUMMARY OF THE INVENTION

The present invention addresses this need by providing, for the first time, compositions comprising a crystallized hepatitis C virus (HCV) NS5B polypeptide. Methods for obtaining purified and crystallized NS5B polypeptide are also provided. Such methods comprise solubilizing a NS5B polypeptide in a solution containing a protein stabilizing agent, subjecting the NS5B preparation to cation exchange chromatography, and allowing crystals to form in a precipitant solution containing a protein stabilizing agent and polyethylene glycol under conditions in which crystallization occurs.

The invention also provides a machine-readable data storage medium encoded with the structural coordinates of a NS5B polypeptide or a homologue thereof. Such a homologue contains backbone atoms having a root mean square deviation of equivalent Cα atoms of less than 3.0 Å when compared to the NS5B polypeptide.

The invention also provides a method for determining at least a portion of the three-dimensional structure of molecules or molecular complexes which contain at least some structurally similar features to a HCV NS5B polypeptide.

Still another aspect of the present invention comprises a method of selecting or optimizing a potential ligand or inhibitor by performing drug design with a three-dimensional structure determined for the crystal, preferably in conjunction with computer modeling. The potential ligand or inhibitor is then contacted with the NS5B polypeptide and the binding thereof is detected. If the ligand is a potential inhibitor of NS5B activity, the candidate drug may then be contacted with NS5B and the inhibition of its activity can be measured.

In another embodiment of the invention, a method of obtaining structural information concerning a molecular complex of unknown structure by using the structure coordinates set forth in Table 1 is provided. Such a method comprises the steps of: generating x-ray diffraction data from a crystal of said complex, and applying crystallographic phases derived from at least a portion of the structure coordinates set forth in Table 1 to said x-ray diffraction pattern to generate a three-dimensional electron density map of at least a portion of the unknown structure.

DETAILED DESCRIPTION OF THE INVENTION

Figure 1A:
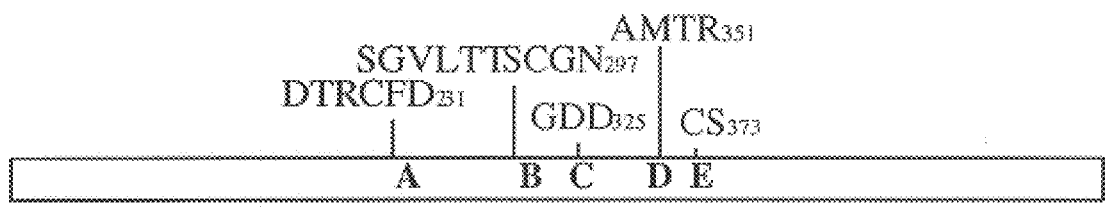
FIG. 1(a) depicts the motif organization of NS5B.

In order that the invention described herein may be more fully understood, the following detailed description is set forth. All references cited herein are incorporated in their entirety by reference.

The present invention provides, for the first time, crystallizable compositions comprising a HCV NS5B polymerase polypeptide. Thus, one embodiment of this invention provides a composition comprising a crystalline hepatitis C virus NS5B polypeptide.

Another embodiment of the invention provides a NS5B protein whose sequence is more similar to various HCV genotypes and subtypes, particularly at amino acid positions 335, 344 and 550 of SEQ ID NO: 1. Preferred amino acids at these positions are valine, alanine and glutamine respectively, while the published sequence (GenBank Accession No. 130458) of the BK isolate has threonine, valine and arginine at the corresponding positions.

Yet another embodiment of this invention provides methods of using NS5B polypeptides to grow a crystal containing such polypeptides. One such method comprises solubilizing a NS5B protein preparation in a solution containing a protein stabilizing agent; subjecting the NS5B protein preparation to cation exchange chromatography in a buffer containing glycine; and allowing crystals to form in the presence of a precipitant containing a protein stabilizing agent, a salt and polyethylene glycol under conditions in which crystallization occurs. Preferably, such a crystal effectively diffracts x-rays for the determination of the atomic coordinates of the protein to a resolution of greater than 4.0 Ångstrōms. More preferably, the crystal effectively diffracts x-rays for the determination of the atomic coordinates of the protein to a resolution of greater than 2.8 Ångströms. In a most preferred embodiment, the crystal effectively diffracts x-rays for the determination of the atomic coordinates of the protein to a resolution of greater than 2.2 Ångstrōms.

As used herein, the terms "HCV NS5B" and "NS5B" refers to the hepatitis C virus non-structural 5B protein as defined in Grakoui, et al., *J. Virol.* 67(3):1385–1395 (1993). See also Simons et al., *Proc. Natl. Acad. Sci. USA* 92(8): 3401–3405 (1995).

HCV "NS5B polypeptides" are polypeptides which have RNA dependent RNA polymerase-like domains similar to the naturally-occurring HCV NS5B. It also includes HCV NS5B and polypeptide fragments of NS5B having polymerase functionalities. These polypeptides also include polypeptides that differ from the NS5B polymerase by having amino acid deletions, substitutions, and additions. NS5B polypeptides may be derived from various HCV genotypes and subtypes known in the art.

The NS5B polypeptide may be produced by any well-known method, including synthetic methods, such as solid phase, liquid phase and combination solid/liquid phase syntheses; recombinant DNA methods, including cDNA cloning, optionally combined with site-directed mutagenesis; and/or purification of the natural products, optionally combined with enzymatic or chemical cleavage methods to produce NS5B or fragments thereof.

Various truncated forms of NS5B are within the scope of the invention and may enhance the solubility of the NS5B protein. A preferred truncation comprises a truncation of a stretch of amino acids in the carboxy terminal region of the protein, preferably containing hydrophobic amino acids. Most preferably, such a truncation includes the four leucine residues in the C-terminal region of NS5B. Truncations of 12–70 amino acids are preferred [Ferrari et al., *J.Virol.* 73:1649–1654 (1999)]. Optionally, it may also be desirable to add amino acids onto the NS5B protein or truncated NS5B. One preferred addition is a polyhistidine tag, 5–20 amino acids in length. Most preferred is a 6 amino acid histidine tag added to the amino-terminus of the NS5B protein or truncated NS5B. Preferably, the NS5B protein has a histidine tag at its amino-terminus for use in purifying the protein.

In one embodiment of the invention, the NS5B polymerase polypeptide is tNS5B, a recombinantly-produced truncated hepatitis C virus RNA dependent RNA polymerase polypeptide. The tNS5B protein contains both a 21 amino acid deletion at the carboxy-terminus and a 6 amino acid histidine tag at the amino-terminus [Ferrari, et al., *J.Virol.* 73:1649–1654 (1999)].

One aspect of the present invention relates to a method of purifying the NS5B polypeptides and obtaining NS5B crystals. Preferably, the NS5B polypeptide may be produced recombinantly in *E. coli* and initial purification may be accomplished by nickel chelate chromatography, as previously described [Petty (1996) "Metal chelate affinity chromatography" in: Ausubel, et al., eds. *Current Protocols in Molecular Biol.*, Vol.2 New York, John Wiley and Sons]. This NS5B preparation is transferred into a solution containing a protein stabilizing agent and glycine. Next, the preparation is applied to a cation exchange resin and subjected to chromatography, eluting the protein with a salt gradient. The resulting solution preferably contains a protein stabilizing agent, a salt, a buffering agent and optionally a reducing agent or an oxygen scavenger. Examples of suitable reducing agents are dithiothreitol (DTT), dithioerythritol (DET) and β-mercaptoethanol. If necessary, the reducing agent is present in the buffered solution at a concentration of about 5 mM and is preferably DTT. The pH of the buffering agent may range from 4.5 to 8, preferably between pH 7 and 8.

Although other solution components can be substituted for the above described components, the protein stabilizing agent and salt appear to be important for the solubility of the NS5B protein preparation. Protein stabilizing agents include polyols, sugars, as well as amino acids and amino acid analogs. Some examples include erythritol, sorbitol, glycerol, fructose, trehalose, proline, β-alanine, taurine and glycine betaine. These agents are sometimes referred to as cosmotropic agents and are well known in the art. [Jeruzalmi & Steitz, *J. Mol. Biol.* 274: 748–756 (1997)]. The concentration of such agents will vary depending upon the type of agent employed. For example, if glycerol is chosen, it is preferably provided in a concentration range from about 2 to about 20% (v/v), preferably about 10% (v/v), while a salt may be provided in a concentration of above about 150 mM. Many salts are routinely used in the art and may be variously used in the method of the present invention.

Glycine in the buffer solution maintains the solubility of the NS5B preparation in the absence of salt and allows further purification by cation exchange chromatography. Various types of cation exchange chromatography may be employed in this purification step. See Scopes, *Protein Purification: Principles and Practice*, Third ed., Springer-Verlag, New York (1994). Glycine can range in concentration from 500–1500 mM, preferably one molar. Glycine is preferably removed after cation exchange chromatography.

Compounds known as "precipitants" are often used to decrease the solubility of the polypeptide in a concentrated solution. Alternatively, "precipitants" can be changes in physical or chemical parameters which decrease polypeptide solubility, including temperature, pH and salt concentrations. Precipitants induce crystallization by forming an energetically unfavorable precipitant-depleted layer around the polypeptide molecules. To minimize the relative amount of this depletion layer, the polypeptides form associations and ultimately crystals as explained in Weber, *Advances in Protein Chemistry* 41:1–36 (1991) which is incorporated by reference. In addition to precipitants, other materials are sometimes added to the polypeptide crystallization solution. These include buffers to adjust the pH of the solution (and hence surface charge on the peptide) and salts to reduce the solubility of the polypeptide. Various precipitants are known in the art and include the following: ammonium sulfate, ethanol, 3-ethyl-2,4 pentanediol; and many of the polyglycols, such as polyethylene glycol. A suitable precipitant for crystallization of NS5B polypeptides is polyethylene glycol (PEG), which combines some of the characteristics of the salts and other organic precipitants.

Crystallization may be accomplished by using any of the known methods in the art [Giegé, et al., *Acta Crystallogr.* D50: 339–350 (1994); McPherson, *Eur. J. Biochem.* 189: 1–23 (1990)]. Such techniques include microbatch, hanging drop, seeding and dialysis. Preferably, hanging-drop vapor diffusion [McPherson, *J. Biol. Chem.* 251: 6300–6303 (1976)] or microbatch methods [Chayen, *Structure* 5: 1269–1274 (1997)] are used. In each of these methods, it is important to promote continued crystal growth after nucleation by maintaining a supersaturated solution. In the microbatch method, polypeptide is mixed with precipitants to achieve supersaturation, the vessel is sealed and set aside until crystals appear. In the dialysis method, polypeptide is retained in a sealed dialysis membrane which is placed into a solution containing precipitant. Equilibration across the membrane increases the precipitant concentration thereby causing the polypeptide to reach supersaturation levels.

It is desirable to use a NS5B protein preparation having a concentration of at least 1 mg/mL and preferably less than 65 mg/mL. Crystallization may be best achieved in a precipitant solution containing polyethylene glycol 1000–20,000 (PEG; average molecular weight ranging from 1000–20,000 Da), preferably 4000–5000 with concentrations ranging from 15–25% (w/v). It is further desirable to avoid the use of extremely high and low molecular weight PEGs. It may also be desirable to include a protein stabilizing agent. If glycerol is chosen as the protein stabilizing agent, it is preferably provided at concentration ranging from 0.5 to 20% (v/v). A suitable salt, such as sodium chloride, may also be desirable in the precipitant solution, preferably in concentration ranging from 1 to 1000 mM. The precipitant is preferably buffered to a pH of about 4.5 to 8.0. Most preferred is a buffer solution at a pH of about 5 to 6. Specific buffers useful in the precipitant solution may vary and are well-known in the art [Scopes, *Protein Purification: Principles and Practice*, Third ed., (1994) Springer-Verlag, New York]. Examples of useful buffers include but are not limited to Tris, MES and acetate. Crystals routinely grow in a wide range of temperature. It is however preferred that crystals form at temperatures between 4° C. and 26° C., and more preferably at 20° C. to 22° C.

The crystals of the present invention have a wide range of uses. For example, high quality crystals are suitable for x-ray or neutron diffraction analysis to determine the three dimensional structure of NS5B polypeptides and in particular to assist in the identification of the protein's active and effector sites. Knowledge of these sites and solvent accessible residues allow rational design and construction of agonists and antagonists for NS5B polypeptides.

In addition, crystallization itself can be used as a purification method. In some instances, a polypeptide or protein crystallizes from a heterogeneous mixture into crystals. Isolation of such crystals by filtration and/or centrifugation, followed by redissolving the polypeptide affords a purified solution suitable for use in growing the high-quality crystals necessary for diffraction analysis.

Once a crystal of the present invention is grown, x-ray diffraction data can be collected. One method for determining structure uses synchrotron radiation, under standard cryogenic conditions for such x-ray diffraction data collection. However alternative methods may also be used. For example, crystals can be characterized by using x-rays produced in a conventional source (such as a sealed tube or a rotating anode), optionally under cryogenic conditions. Methods of characterization include, but are not limited to, precession photography, oscillation photography and diffractometer data collection.

Advantageously, the crystallizable compositions provided by this invention are amenable to x-ray crystallography. Thus, this invention also provides the three-dimensional structure of an HCV NS5B polypeptide at 1.9 Å resolution. Importantly, this has provided for the first time, detailed information about the shape and structure of the NS5B polymerase protein.

The three-dimensional structure of the HCV NS5B polymerase of this invention is defined by a set of structure coordinates as set forth in Table 1. The term "structure coordinates" refers to Cartesian coordinates derived from mathematical equations related to the patterns obtained on diffraction of a beam of x-rays by the atoms (scattering centers) of NS5B polymerase in crystal form. The diffraction data are used to calculate electron density maps and to establish the positions of the individual atoms of the NS5B enzyme.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above may be generated because of mathematical manipulations of the structure coordinates. For example, the structure coordinates set forth in Table 1 can be manipulated by crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the original coordinates, the resulting three-dimensional shape is considered to be the same.

Various computational analyses are therefore necessary to determine whether a molecular complex or a portion thereof is sufficiently similar to all or parts of the NS5B polypeptide structure described above as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) input the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA (Molecular Simulations Inc., San Diego, Calif.) is defined by user input, for the purpose of this invention, equivalent atoms are defined as protein alpha carbon atoms ($C\alpha$). When the Cα atoms of the working structure are superimposed on the relevant reference Cα atoms described by structure coordinates listed in Table 1 with an RMSD of less than 3 Å, the two structures are considered identical. More preferably, the root mean square deviation is less than 2.0 Å.

The term "root mean square deviation" or "RMSD" means the square root of the arithmetic mean of the squares of the deviations from the mean. It is a way to express the deviation or variation from a trend or object. For purposes of this invention, the "root mean square deviation" defines the variation in the alpha carbon of a protein or protein complex from the relevant portion of the alpha carbon of the NS5B polypeptide as defined by the structure coordinates described herein.

Thus, in accordance with the present invention, the structure coordinates of the NS5B polypeptide and portions thereof are stored in a machine-readable storage medium. Such data may be used for a variety of purposes, such as drug discovery and x-ray crystallographic analysis of a protein crystal.

Accordingly, one aspect of this invention provides a machine-readable data storage medium comprising a data storage material encoded with the structure coordinates set forth in Table 1.

A computer system useful in reading the machine readable data storage medium includes a computer comprising a central processing unit ("CPU") and a memory storage device. In general, the computer system may be any computer with an operating system such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages will be known to those skilled in the art.

Input hardware coupled to the computer system by input lines, may be implemented in a variety of ways. Machine-readable data of this invention may be inputted via the use of a modem or modems connected by a telephone line or a dedicated data line. Alternatively or additionally, the input hardware may comprise CD-ROM drives or disk drives. A keyboard or optical scanner may also be used as an input device.

Output hardware, coupled to the computer system by output lines, may similarly be implemented by conventional devices. By way of example, output hardware may include a display terminal for displaying a graphical representation of a binding pocket of this invention using a program such as INSIGHT (Molecular Simulations Inc., San Diego, Calif.) as described herein. Output hardware might also include a printer, so that hard copy output may be produced, or a disk drive, to store system output for later use.

In operation, the CPU coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the computer system are included as appropriate throughout the following description of the data storage medium.

A magnetic data storage medium can be encoded with a machine-readable data by a computer system as described above. Storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. Storage medium may also have an opening for receiving the spindle of a disk drive or other data storage device. Alternatively, an optically-readable data storage medium can be encoded with such a machine-readable data, or a set of instructions. Medium can be a conventional compact disk read only memory (CD-ROM) or a rewritable medium such as a magneto-optical disk which is optically readable and magneto-optically writable.

In the case of CD-ROM, as is well known, a coating is reflective and is impressed with a plurality of pits to encode the machine-readable data. The arrangement of pits is read by reflecting laser light off the surface of the coating. A protective coating, which preferably is substantially transparent, is provided on top of the coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

The present invention permits the use of structure-based drug design techniques to design, select, and optionally optimize the structure of chemical entities, including inhibitory compounds that are capable of binding to HCV NS5B polymerase or any portion thereof. Also, de novo drug design methods with iterative structure-based drug design methods can be used to develop inhibitors from the crystal structure of the present invention.

One particularly useful drug design technique enabled by this invention is structure-based drug design. Structure-based drug design is a method for optimizing associations between a protein and a compound by determining and evaluating the three-dimensional structures of one or more sets of protein/compound complexes.

Those skilled in the art will realize that association of natural ligands or substrates with the binding pockets of their corresponding receptors or enzymes is the basis of many biological mechanisms of action. The term "binding pocket", as used herein, refers to any region of a molecule or molecular complex, that, as a result of its shape, favorably associates with another chemical entity or compound. Similarly, drugs may exert their biological effects through association with the binding pockets of receptors and enzymes. Such association may occur with all or a subset of the binding pockets. An understanding of such associations will help lead to the design of drugs having more favorable associations with the target enzyme, and thus, improved biological effects. Therefore, this information is valuable in designing enzyme inhibitors, such as inhibitors of HCV NS5B polypeptides.

In iterative structure-based drug design, crystals of a series of protein/compound complexes are obtained and then the three-dimensional structures of each complex are solved. Such an approach provides insight into the association between the proteins and compounds of each complex. This is accomplished by selecting a compound with inhibitory activity, obtaining crystals of the polypeptide in complex with this compound, solving the three-dimensional structure of the complex, and comparing the polypeptide/compound associations between the new structure and previously solved structure(s). By observing how changes in the compound affect the protein/compound associations, these associations may be optimized.

In some cases, iterative structure-based drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, the HCV NS5B polymerase crystals provided by this invention may be soaked in the presence of a compound or compounds, such as NS5B inhibitors, substrates or other ligands to provide NS5B polypeptide compound crystal complexes. As used herein, the term "soaked" refers to a process in which the crystal is transferred to a solution containing the compound of interest or the compound of interest is added to the solution containing the crystal.

The structure coordinates set forth in Table 1 can also be used to aid in obtaining structural information about another crystallized molecule or molecular complex. This may be achieved by any of a number of well-known techniques, including molecular replacement.

The structure coordinates set forth in Table 1 can also be used for determining at least a portion of the three-dimensional structure of molecules or molecular complexes which contain at least some structurally similar features to HCV NS5B. In particular, structural information about another crystallized molecule or molecular complex may be obtained using well-known techniques, including molecular replacement.

Therefore, another aspect of this invention provides a method of utilizing molecular replacement to obtain structural information about a crystallized molecule or molecular complex whose structure is unknown comprising the steps of:

a) generating an x-ray diffraction pattern from said crystallized molecule or molecular complex; and b) applying crystallographic phases derived from at least a portion of the structure coordinates set forth in Table 1 to the x-ray diffraction pattern to generate a three-dimensional electron density map of at least a portion of the molecule or molecular complex whose structure is unknown.

Once the structure coordinates of a protein crystal have been determined, they are useful in solving the structures of other crystals. In addition, the structures of NS5B complexes can be determined from the structure coordinates of the present invention. For example, complexes may be crystallized and their structure elucidated using such methods as difference Fourier or molecular replacement. NS5B complexes suitable for such analysis include, for example, NS5B in complex with an oligonucleotide template/primer duplex (i.e. substrate), wherein the duplex may have a single-stranded overhang of one or both strands on either or both ends of the oligonucleotide. Another example complex is NS5B complexed with a nucleotide triphosphate (i.e. substrate) or analog thereof. Most preferred is NS5B complexed with inhibitors such as nucleotide analogs, non-nucleotide inhibitors or inhibitors unrelated to substrate molecules. Yet another NS5B complex suitable for structure determination using the structure coordinates of NS5B is NS5B in complex with other members of the putative replicase complex, such as HCV NS3 protein, NS3 helicase domain, NS3 protease domain or other HCV proteins. A further NS5B complex suitable for structure determination is NS5B in complex with one or more cellular host factors (Cf. thioredoxin and T7 DNA polymerase) [Doublié et al., *Nature* 391: 251–258(1998)]. Suitable complexes of NS5B may contain several other molecules or combinations of the above described complexes.

Preferably, the crystallized molecule or molecular complex comprises a NS5B polypeptide. More preferably, the crystallized molecule or molecular complex is obtained by soaking a crystal of this invention in a solution. By using molecular replacement, all or part of the structure coordinates of the NS5B polymerase provided by this invention (and set forth in Table 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor, in equations used to solve crystal structures, that can not be measured experimentally. Obtaining accurate values for the phases, by methods other than molecular replacement, is a time-consuming process. However, when the crystal structure of a protein containing at least a homologous portion has been solved, the phases from the known structure may provide a satisfactory initial estimate of the phases for the unknown structure.

Thus, this method involves generating a preliminary model of a molecule or molecular complex whose structure coordinates are unknown, by orienting and positioning the relevant portion of the NS5B polymerase according to Table 1 within the unit cell of the crystal of the unknown molecule or molecular complex so as best to account for the observed x-ray diffraction pattern amplitudes to generate an electron density map of the structure whose coordinates are unknown. This, in turn, can be subjected to any well-known model building and structure refinement technique to provide a final, accurate structure of the unknown crystallized molecule or molecular complex [Lattman, "Use of the Rotation and Translation Functions", in *Meth. Enzymol.*, 115: 55–77 (1985); Rossman, ed., "The Molecular Replacement Method", *Int. Sci. Rev. Ser.*, No. 13, Gordon & Breach, New York (1972)].

Phase information from the structure coordinates of the present invention may be used to elucidate the structure of other crystals. For example, NS5B molecules in complex with other atoms or molecules, as described above, including complexes containing a heavy atom substructure from which useful phasing information may be extracted. Such complexes include, for example, those containing sulfur atoms of the endogenous cysteine and methionine amino acids as well as any atoms incorporated into, soaked into or cocrystallized within the crystal lattice. Other structures which can be elucidated using the phase information of the present invention include for example other RNA-dependent RNA polymerases (RdRps) of sufficient three-dimensional structure similarity to HCV NS5B as to be solved using molecular replacement. Examples of such RdRps include but are not limited to RdRp from bovine viral diarrhea virus, RdRp from yellow fever virus and RdRp from Dengue virus. Also, RdRps in a complex with a small molecule substrate, inhibitor, intermediate, transition state analog, product or analog of any of these may also be solved using phase information contained in the present invention. Other complexes whose structure can be elucidated from the phase information of the present invention include an RdRp in a complex with a macromolecule such as a template/primer substrate or host elongation factor, such as T7 DdDp/thioredoxin, or with a transcription inhibitor, such as T7 DdRp/T7 lysozyme, or with another HCV protein, such as NS3 protein, NS3 helicase or NS3 protease for example.

Complexes containing a combination of the above molecules may also be solved using phase information of the present invention.

The structure of any portion of any crystallized molecule or molecular complex that is sufficiently homologous to any portion of the NS5B polymerase can be solved by this method. The difference Fourier method simply calculates an electron density map using phases calculated from the structure coordinates and observed diffraction amplitudes from a crystal of an unknown structure. This well-known method is often used to solve structures of protein/ligand complexes where the ligand is small and does not affect the crystal form significantly.

In a preferred embodiment, the method of molecular replacement is utilized to obtain structural information about a molecule wherein the molecule comprises a NS5B polypeptide or variant or complex thereof. Preferably the NS5B polypeptide comprises tNS5B or homologues thereof.

The structure coordinates of NS5B polymerase provided by this invention are particularly useful in solving the structure of other crystal forms of NS5B polypeptides.

The structure coordinates are also particularly useful to solve the structure of crystals of NS5B polypeptides, particularly tNS5B and polypeptides related in structure to NS5B. This approach enables the determination of the optimal sites for interaction between chemical entities, including interaction of candidate NS5B inhibitors with NS5B.

All of the complexes referred to above may be studied using well-known x-ray diffraction techniques may be refined versus x-ray data to 3 Å resolution or better, to an $R_{free}$ value of about 0.40 or less using computer software, such as X-PLOR [Yale University, ©1992, distributed by Molecular Simulations, Inc.; see e.g., Blundell & Johnson, supra; *Meth, Enzymol.*, vol. 114 & 115, H. W. Wyckoff et al., eds., Academic Press (1985)]. This information may thus be used to optimize known NS5B inhibitors, and to design new NS5B inhibitors.

In order that this invention be more fully understood, the following examples are set forth. These examples are for the illustrative purposes only and are not to be construed as limiting the scope of this invention in any way.

EXAMPLE 1
Construction of tNS5B

The amino acid sequence of NS5B (BK) was compared to 16 NS5B proteins from different genotypes and subtypes. Four isolates represent genotype 1 subtype a (HCV-1a) and five are from HCV-1b. The rest are from HCV-2a, 2b, 3a, 3b, 4a, 5a and 6a. Two substitutions were made to the NS5B (BK) sequence, one "T" to "V" at position 335, the other "V" to "A" at position 344 numbered according to SEQ ID NO: 1. The NS5B protein contains an additional change from the published NS5B (BK) sequence (GenBank Accession No. 130458), namely, an "R" to "Q" at position 550 numbered according to SEQ ID NO:1. This NS5B protein has an amino acid sequence more similar than the published NS5B sequence to the other genotypes analyzed.

To make these substitutions, site-directed mutagenesis using the "Quick Change" mutagenesis kit (Stratagene, Calif.) was performed. The resulting clone was verified by direct sequencing. This NS5B construct was subcloned into pET-21b (Novagen, Wis.) between NheI and BamHI sites. Additional codons were engineered at the N-terminus (coding for a polyhistidine tag, MASHHHHHH, and replacing the native amino acids "SM" at the N-terminus of NS5B) to facilitate the cloning and purification. The C-terminal 21 amino acids were deleted to improve the solubility of NS5B. The sequence of the modified NS5B (designated as His-NS5BΔCT21) is set forth as SEQ ID NO: 1.

EXAMPLE 2
Expression and Purification of tNS5B

Hepatitis C virus (HCV) NS5B RNA-dependent RNA polymerase (RdRp) was cloned, transformed into *E. coli* and purified as previously described using nickel chelate chromatography. The particular construct used in this Example is described above and incorporated a six-histidine tag at the N-terminus and a 21-residue truncation from the C-terminus. See also Ferrari, et al., *J. Virol.* 73:1649–1654 (1999). HCV NS5B RdRp was further purified using cation exchange resin (Mono-S HR 16/10, (Amersham Pharmacia Biotech AB, Uppsala, Sweden)) after overnight dialysis into 10% (v/v) glycerol, and 1 M glycine pH 7.0. After gel filtration chromatography (HiPrep 16/60 Sephacryl S100 High Resolution (Amersham Pharmacia AB, Uppsala, Sweden)) into 10% (v/v) glycerol, 600 mM NaCl, 5 mM DTT and 10 mM Tris pH 7.5, recombinant HCV NS5B was concentrated to between 10 and 40 mg/mL. At this stage, the concentrated protein was stored at −80° C. until needed.

EXAMPLE 3
Crystallization and Data Collection

Crystallization experiments were conducted using both hanging-drop vapor diffusion and microbatch methods using newly prepared or freshly-thawed protein. For vapor-diffusion experiments, 2 μL of protein was mixed with an equal volume of precipitant solution, placed on the underside of a siliconized glass coverslip, and sealed in close proximity to 1 mL of the precipitant solution. For the microbatch experiments, 2 μL of protein was mixed thoroughly with an equal volume of precipitant solution and dispensed beneath a layer of paraffin oil. The precipitant solution contained poly(ethylene)glycol 1000 to 20,000 (PEG; average MW ranging from 1000 to 20,000 Da) with concentrations ranging from 15 to 25% [(v/v) or (w/v)]. The precipitant solution also contained 10% (v/v) glycerol and concentrations of NaCl ranging from 0 to 600 mM NaCl, using various buffers between pH 4.5 and 7.0. These buffers included acetate, MES, and Tris. After incubation at temperatures between 4° C. and 26° C. for 24 h, small plate-like crystals formed. Crystals grew to terminal size within two weeks with dimensions up to 300×300×50 μm. After transfer of the crystals to cryoprotectant containing a few percent more PEG than the crystallization medium and up to 30% (v/v) glycerol, the crystals could be either frozen directly in liquid propane for storage prior to diffraction data collection or frozen in a gaseous nitrogen stream immediately before diffraction data collection.

EXAMPLE 4
Protein Preparation. MAD Experiment and Phasing

In preparation for a multiwavelength anomalous diffraction (MAD) experiment for the purpose of obtaining experimental crystallographic phases, a suitable atom or set of atoms must be incorporated into the crystal lattice. It is essential that this atom have an absorption edge within the practical range of x-ray wavelengths used for diffraction data collection. Rather than absorption, fluorescence is conventionally measured. This atom or set of atoms may be added exogenously to the native protein molecule (by soaking or cocrystallization methods), incorporated synthetically or incorporated biosynthetically into the protein itself. We chose the last method by substituting selenomethionine into the protein for the native methionine. This was accomplished by inhibiting the expression system's pathway for methionine biosynthesis and adding a suitable amount of selenomethionine to the growth medium for incorporation into the overexpressed protein. One may also use an expression system which is auxotrophic for methionine and similarly provide selenomethionine in the growth medium. This process is described in Doublié [Doublié, *Meth. Enz.* 276: 523–530 (1997)].

The selenomethionine-incorporated HCV NS5B protein was purified and crystallized in the same manner as the wild-type (sulfur-containing methionine) enzyme.

A MAD experiment was performed at beamline 17-ID-B at the Advanced Photon Source at Argonne National Laboratory as described in Hendrickson and Ogata [Hendrickson & Ogata, *Meth. Enz.* 276: 494–523 (1997)]. Briefly, an x-ray fluorescence energy scan was collected from a Se met NS5B crystal. Data from this scan were used to assign the fluorescence edge and peak to determine the precise wavelengths of x-ray radiation required for the experiment. Complete x-ray diffraction data sets were collected, using the inverse-beam method [Hendrickson & Ogata, *Meth. Enz.* 276: 494–523 (1997)], at the peak fluorescence (wavelength=0.979 Å), at the fluorescence edge (0.980 Å) and at a low-energy remote wavelength (1.032 Å).

Unprocessed diffraction images were indexed and the diffraction intensities integrated using the HKL computer program package [Otwinowski & Minor, *Meth. Enzymol.* 276: 307–326 (1997)]. Integrated intensities were reduced to unique data (as amplitides) using the programs of the CCP4 package including SCALA and TRUNCATE [Evans, *Joint CP4 and ESF-EACBM Newsletter* 33: 22–24 (1997); French & Wilson, *Acta Crystallogr.* A34: 517–525 (1978)].

The selenium atom substructure was deduced using the direct methods structure solution software Shake-and-Bake version 2.0 beta [Miller et al., *J. Appl. Crystallogr.* 27: 613–621 (1994)] using the reduced, unique data from the peak fluorescence wavelength only.

The calculated sites for the 22 expected (based on amino acid sequence of the NS5B monomer and the anticipation of two NS5B monomers per asymmetric unit, which is based on calculation of the Matthews coefficient and other crystallographic analyses [Matthews, *J. Mol. Biol.* 33: 491–497 (1968)]) were then refined and experimental MAD phases calculated using the software SHARP [de La Fortelle & Bricogne, *Meth. Enzymol.* 276: 472–494 (1996)]. Subsequent density modification using the program SOLOMON [Abrahams & Leslie, *Acta Crystallogr.* D52: 30–42 (1996)] resulted in an interpretable electron density map.

EXAMPLE 5
Model Building and Refinement

After the polypeptide backbone was fit into the experimental electron density using the software O [Jones et al., *Acta Crystallogr.* A47: 110–119 (1991)], amino acid side chains were fit into electron density and the HCV NS5B primary sequence was registered onto the three dimensional polypeptide trace. After an initial cycle of manual fitting, the three dimensional coordinates were subjected to coordinate and B-factor refinement using simulated-annealing techniques implemented in the program X-PLOR [Brünger et al., *Acta Crystallogr* A 46: 585–93 (1990); Karplus et al., *Cold Spring Harb Symp Quant Biol* 52: 381–90 (1987)]. Iterative cycles of manual rebuilding, placement of solvent molecules, and refinement followed until convergence of the free R-factor to 0.30 [Kleywegt & Brunger, *Structure* 4:897–904 (1996); Kleywegt & Jones, *Structure* 3: 535–40 (1995)]. The stereochemical quality of the model was checked and verified at each cycle with the aid of the programs PROCHECK [Laskowski et al., *J. Appl. Crystallogr.* 26: 283–291 (1993)] and WHATIF [Hooft et al., *Nature* 381: 272 (1996)].

Crystals contain two HCV NS5B monomers per asymmetric unit and belong to space group $P2_12_12_1$ with unit cell dimensions 86×105×126 Å. These crystals diffract to at least 1.9 Å resolution. A refined model of HCV NS5B RdRp was produced using data collected from a selenomethionine-incorporated protein. This three-dimensional atomic model contains greater than 95% of the expected scattering matter in the crystal and may be used to solve, using difference Fourier or molecular replacement techniques, the crystal structures of HCV NS5B:ligand complexes where the ligand is a small-molecule inhibitor or substrate of this enzyme. This crystal form is suitable for structure-based drug design due to: (a) only modest concentrations of NaCl and PEG used for crystallization and (b) exposure of the active site to solvent channels. A schematic-representation of the HCV NS5B RdRp structure is shown in FIG. 1(b).

Figure 1B:
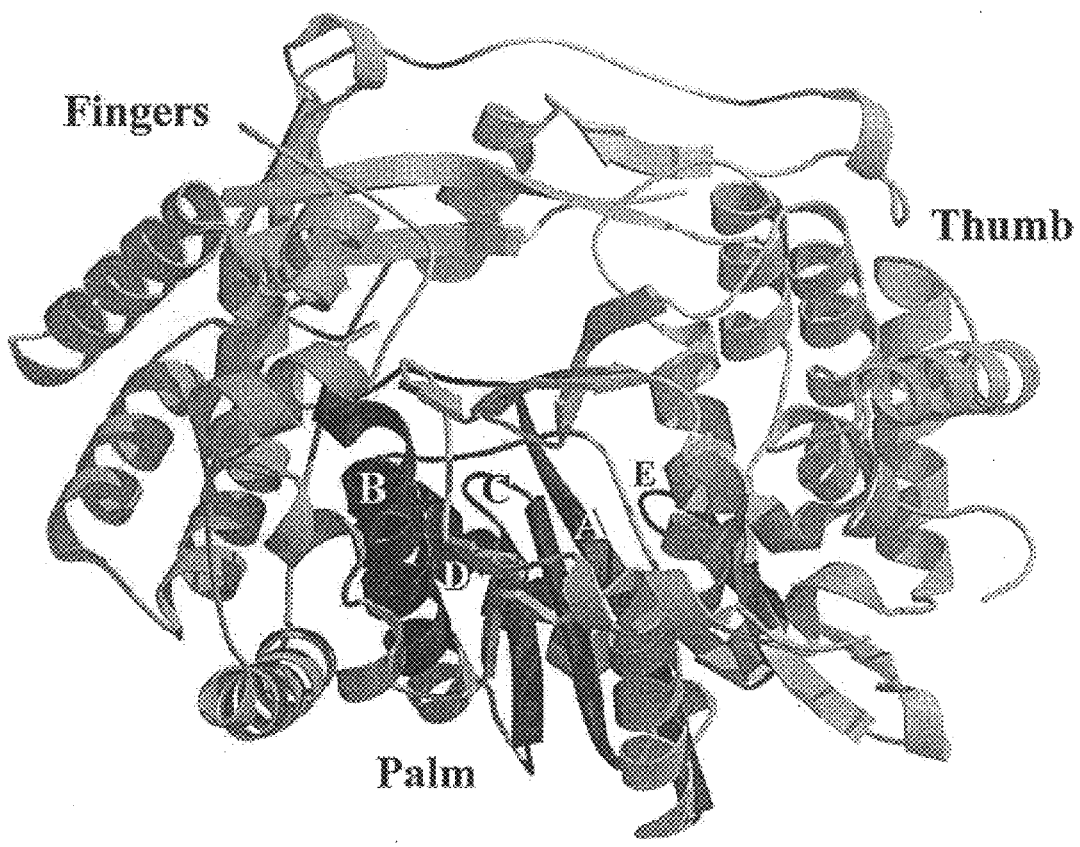
FIG. 1(b) depicts a schematic diagram of NS5B polymerase.

FIG. 1(b) contains schematic representations of the HCV NS5B RdRp monomer in a single large image, showing the location of the structural motifs in the three dimensional structure. The conserved structural motifs found in polymerases [Hansen et al., *Structure*, 5:1109–1122 (1997)] are denoted as lettered dark gray regions; the remainder of the molecule is lighter. The amino acid sequence of these motifs is shown (FIG. 1(a)), above FIG. 1(b) and are:

Motif A: This region forms one strand of the central beta-sheet and contributes an aspartate (D) to the active site;

Motif B: This region determines specificity between a NTP and dNTP substrate;

Motif C: This motif contains the sequence motif GDD and is directly implicated in divalent metal binding and nucleotidyl transferase activity;

Motif D: Buttresses the central beta-sheet; and

Motif E: Determines specificity between DNA and RNA template.

These motifs have all individually been shown to be required for catalytic activity [Hansen et al., *Structure*, 5:1109–1122 (1997); Joyce & Steitz, *Ann. Rev. Biochem.* 63:777–822 (1994); Poch et al., *EMBO J.* 8:3867–3874 (1989); Sousa, *Trends Biochem Sci.* 21:186–190 (1996)]. The three-dimensional colocalization of the motifs (in the 'palm' subdomain) defines the position of the catalytic active site. Additionally, the 'thumb' and 'fingers' regions (denoted on the Figure), have been shown to bind to the primer strand substrate and template strand substrate, respectively, in other members of the greater polymerase family [Doublié et al., *Nature* 391:251–258 (1998); Huang et al., *Science* 282:1669–1675 (1998); Jacobo-Molina et al., *Proc. Natl. Acad. Sci.* USA 90:6320–6324 (1993); Kiefer et al., *Nature* 391:304–307 (1998), Pelletier et al., *Science* 264:1891–1903 (1994)].

FIG. 1(b) was created using Molscript and Raster3D [Kraulis, *J. Appl. Crystallogr.* 24:946–950 (1991); Merritt & Bacon, *Meth. Enzymol.* 277:505–524 (1997)].

Table 1 lists the atomic structure coordinates for hepatitis C virus recombinant tNS5B polymerase, as derived by x-ray diffraction from crystals. The specific columns in Table 1 are defined as follows:

| Column | Description |
|---|---|
| 1 | Residue number (using numbering scheme of Table 1) |
| 2 | Residue name, using one-letter code (X = solvent) |
| 3 | Atom name, conventional PDB nomenclature (OW = solvent) |
| 4 | X-coordinate in orthogonal Ångstroms, multiplied by 10 |
| 5 | Y-coordinate in orthogonal Ångstroms, multiplied by 10 |
| 6 | Z-coordinate in orthogonal Ångstroms, multiplied by 10 |
| 7 | B-factor, in Å$^2$ |

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to utilize the invention in various embodiments and with various modifications as are suited to the particular use contemplated. It is intended that the scope of the invention be defined by the claims appended hereto.

TABLE 1

The following table contains one line for each atom in one HCV NS5B monomer as well as solvent molecules. The columns are: 1) residue number, 2) 1-letter amino acid code, 3) atom name, 4) x-coordinate multiplied by 10, 5) y-coordinate multiplied by 10, 6) z-coordinate multiplied by 10, and 7) B-factor. The coordinates of the second monomer ($x_2$, $y_2$, $z_2$) are related to the coordinates of the first monomer ($x_1$, $y_1$, $z_1$) listed below according to the following operation:

$$x_2 = x_1 \cdot a_{11} + y_1 \cdot a_{12} + z_1 \cdot a_{13} + t_1$$
$$y_2 = x_1 \cdot a_{21} + y_1 \cdot a_{22} + z_1 \cdot a_{23} + t_2$$
$$z_2 = x_1 \cdot a_{31} + y_1 \cdot a_{32} + z_1 \cdot a_{33} + t_3 \quad \text{where}$$

$$\begin{array}{l} a_{11}\ a_{12}\ a_{13} \\ a_{21}\ a_{22}\ a_{23} = \\ a_{31}\ a_{32}\ a_{33} \end{array} \begin{array}{rrr} -0.99978 & 0.01956 & 0.00754 \\ 0.01940 & 0.99961 & -0.01986 \\ -0.00793 & -0.01971 & 0.99977 \end{array} \quad \text{and}$$

$$t_1 \quad t_2 \quad t_3 \quad = -1.37838 \quad 0.34470 \quad 41.27925$$

The noncrystallographic operation described above should only be applied to the HCV NS5B protein atoms (i.e. residues 7 through 569). Following the protein atoms are listed all discrete solvent molecules (residue X, atom OW) which were modeled into the asymmetric unit.

| | | | | | | |
|---|---|---|---|---|---|---|
| 7 | H | N | 161 | 376 | 196 | 40 |
| 7 | H | CA | 152 | 378 | 208 | 40 |
| 7 | H | C | 159 | 374 | 222 | 36 |
| 7 | H | O | 152 | 369 | 231 | 32 |
| 7 | H | CB | 138 | 371 | 207 | 42 |
| 7 | H | CG | 129 | 376 | 196 | 44 |
| 7 | H | ND1 | 124 | 368 | 187 | 43 |
| 7 | H | CD2 | 125 | 389 | 193 | 42 |
| 7 | H | CE1 | 117 | 375 | 178 | 46 |
| 7 | H | NE2 | 117 | 388 | 182 | 43 |
| 8 | H | N | 172 | 376 | 223 | 33 |
| 8 | H | CA | 178 | 373 | 235 | 31 |
| 8 | H | C | 178 | 384 | 245 | 24 |
| 8 | H | O | 178 | 395 | 241 | 19 |
| 8 | H | CB | 193 | 369 | 232 | 38 |
| 8 | H | CG | 195 | 356 | 225 | 45 |
| 8 | H | ND1 | 201 | 354 | 213 | 44 |
| 8 | H | CD2 | 190 | 343 | 229 | 45 |
| 8 | H | CE1 | 200 | 342 | 209 | 48 |
| 8 | H | NE2 | 194 | 335 | 219 | 50 |
| 9 | S | N | 177 | 380 | 258 | 22 |
| 9 | S | CA | 177 | 391 | 268 | 20 |
| 9 | S | C | 189 | 399 | 268 | 18 |
| 9 | S | O | 189 | 411 | 271 | 17 |
| 9 | S | CB | 175 | 384 | 282 | 18 |
| 9 | S | OG | 183 | 372 | 283 | 19 |

TABLE 1-continued

| | | | | | | |
|---|---|---|---|---|---|---|
| 10 | Y | N | 201 | 393 | 265 | 18 |
| 10 | Y | CA | 214 | 400 | 265 | 21 |
| 10 | Y | C | 223 | 394 | 255 | 20 |
| 10 | Y | O | 222 | 383 | 251 | 20 |
| 10 | Y | CB | 221 | 399 | 278 | 17 |
| 10 | Y | CG | 214 | 405 | 291 | 17 |
| 10 | Y | CD1 | 216 | 419 | 294 | 16 |
| 10 | Y | CD2 | 206 | 397 | 299 | 19 |
| 10 | Y | CE1 | 209 | 424 | 305 | 19 |
| 10 | Y | CE2 | 200 | 403 | 310 | 19 |
| 10 | Y | CZ | 201 | 416 | 313 | 17 |
| 10 | Y | OH | 195 | 421 | 323 | 25 |
| 11 | T | N | 233 | 403 | 250 | 22 |
| 11 | T | CA | 243 | 398 | 241 | 25 |
| 11 | T | C | 256 | 404 | 248 | 25 |
| 11 | T | O | 256 | 415 | 253 | 26 |
| 11 | T | CB | 243 | 404 | 226 | 25 |
| 11 | T | OG1 | 240 | 418 | 226 | 28 |
| 11 | T | CG2 | 232 | 396 | 218 | 26 |
| 12 | W | N | 266 | 396 | 249 | 25 |
| 12 | W | CA | 279 | 400 | 256 | 26 |
| 12 | W | C | 291 | 401 | 247 | 27 |
| 12 | W | O | 293 | 393 | 238 | 28 |
| 12 | W | CB | 281 | 390 | 267 | 20 |
| 12 | W | CG | 269 | 388 | 276 | 20 |
| 12 | W | CD1 | 261 | 378 | 277 | 19 |
| 12 | W | CD2 | 265 | 398 | 286 | 19 |
| 12 | W | NE1 | 252 | 380 | 287 | 19 |
| 12 | W | CE2 | 254 | 392 | 293 | 19 |
| 12 | W | CE3 | 269 | 410 | 291 | 17 |
| 12 | W | CZ2 | 247 | 398 | 303 | 16 |
| 12 | W | CZ3 | 262 | 416 | 301 | 21 |
| 12 | W | CH2 | 251 | 410 | 307 | 14 |
| 13 | T | N | 299 | 411 | 250 | 28 |
| 13 | T | CA | 312 | 413 | 242 | 28 |
| 13 | T | C | 323 | 405 | 248 | 31 |
| 13 | T | O | 332 | 400 | 241 | 35 |
| 13 | T | CB | 317 | 428 | 242 | 26 |
| 13 | T | OG1 | 319 | 432 | 256 | 27 |
| 13 | T | CG2 | 307 | 437 | 235 | 26 |
| 14 | G | N | 323 | 403 | 261 | 31 |
| 14 | G | CA | 333 | 395 | 267 | 30 |
| 14 | G | C | 341 | 404 | 277 | 30 |
| 14 | G | O | 350 | 399 | 284 | 31 |
| 15 | A | N | 339 | 417 | 277 | 27 |
| 15 | A | CA | 345 | 426 | 286 | 26 |
| 15 | A | C | 339 | 422 | 300 | 29 |
| 15 | A | O | 327 | 419 | 301 | 29 |
| 15 | A | CB | 343 | 441 | 283 | 22 |
| 16 | L | N | 347 | 423 | 310 | 31 |
| 16 | L | CA | 342 | 419 | 324 | 30 |
| 16 | L | C | 334 | 429 | 331 | 24 |
| 16 | L | O | 336 | 441 | 329 | 25 |
| 16 | L | CB | 354 | 415 | 332 | 30 |
| 16 | L | CG | 363 | 404 | 328 | 33 |
| 16 | L | CD1 | 375 | 403 | 337 | 35 |
| 16 | L | CD2 | 356 | 391 | 328 | 32 |
| 17 | I | N | 325 | 425 | 339 | 26 |
| 17 | I | CA | 316 | 433 | 347 | 25 |
| 17 | I | C | 326 | 436 | 359 | 25 |
| 17 | I | O | 330 | 426 | 366 | 26 |
| 17 | I | CB | 303 | 427 | 353 | 21 |
| 17 | I | CG1 | 294 | 423 | 341 | 19 |
| 17 | I | CG2 | 296 | 436 | 362 | 18 |
| 17 | I | CD1 | 281 | 418 | 344 | 21 |
| 18 | T | N | 331 | 448 | 360 | 25 |
| 18 | T | CA | 341 | 451 | 370 | 27 |
| 18 | T | C | 336 | 459 | 382 | 28 |
| 18 | T | O | 326 | 466 | 382 | 26 |
| 18 | T | CB | 352 | 459 | 363 | 22 |
| 18 | T | OG1 | 347 | 471 | 357 | 23 |
| 18 | T | CG2 | 359 | 451 | 353 | 20 |
| 19 | P | N | 343 | 457 | 393 | 30 |
| 19 | P | CA | 339 | 463 | 406 | 33 |
| 19 | P | C | 344 | 478 | 406 | 38 |
| 19 | P | O | 352 | 482 | 398 | 37 |
| 19 | P | CB | 346 | 455 | 417 | 32 |
| 19 | P | CG | 358 | 450 | 410 | 33 |
| 19 | P | CD | 354 | 447 | 396 | 30 |

TABLE 1-continued

| | | | | | | |
|---|---|---|---|---|---|---|
| 20 | C | N | 339 | 485 | 416 | 43 |
| 20 | C | CA | 343 | 499 | 418 | 46 |
| 20 | C | C | 355 | 498 | 428 | 48 |
| 20 | C | O | 366 | 497 | 424 | 52 |
| 20 | C | CB | 332 | 508 | 423 | 48 |
| 20 | C | SG | 334 | 525 | 417 | 65 |
| 21 | A | N | 351 | 498 | 441 | 47 |
| 21 | A | CA | 361 | 497 | 451 | 45 |
| 21 | A | C | 364 | 482 | 454 | 44 |
| 21 | A | O | 359 | 474 | 447 | 46 |
| 21 | A | CB | 357 | 504 | 464 | 46 |
| 22 | A | N | 372 | 479 | 464 | 44 |
| 22 | A | CA | 375 | 466 | 468 | 42 |
| 22 | A | C | 362 | 460 | 473 | 40 |
| 22 | A | O | 353 | 467 | 479 | 38 |
| 22 | A | CB | 386 | 465 | 479 | 44 |
| 23 | E | N | 361 | 446 | 472 | 37 |
| 23 | E | CA | 349 | 439 | 476 | 35 |
| 23 | E | C | 353 | 428 | 486 | 33 |
| 23 | E | O | 362 | 421 | 484 | 35 |
| 23 | E | CB | 342 | 433 | 464 | 32 |
| 23 | E | CG | 337 | 442 | 453 | 30 |
| 23 | E | CD | 332 | 435 | 441 | 33 |
| 23 | E | OE1 | 339 | 427 | 435 | 33 |
| 23 | E | OE2 | 320 | 437 | 437 | 33 |
| 24 | E | N | 345 | 427 | 497 | 32 |
| 24 | E | CA | 346 | 417 | 507 | 29 |
| 24 | E | C | 336 | 406 | 505 | 27 |
| 24 | E | O | 324 | 410 | 502 | 28 |
| 24 | E | CB | 344 | 423 | 521 | 30 |
| 24 | E | CG | 354 | 434 | 525 | 39 |
| 24 | E | CD | 351 | 437 | 540 | 41 |
| 24 | E | OE1 | 342 | 445 | 542 | 40 |
| 24 | E | OE2 | 359 | 432 | 548 | 43 |
| 25 | S | N | 339 | 394 | 506 | 28 |
| 25 | S | CA | 329 | 383 | 505 | 28 |
| 25 | S | C | 327 | 377 | 519 | 26 |
| 25 | S | O | 316 | 372 | 522 | 26 |
| 25 | S | CB | 334 | 373 | 495 | 30 |
| 25 | S | OG | 345 | 365 | 500 | 34 |
| 26 | K | N | 338 | 377 | 527 | 26 |
| 26 | K | CA | 337 | 370 | 540 | 28 |
| 26 | K | C | 332 | 380 | 551 | 20 |
| 26 | K | O | 336 | 392 | 551 | 20 |
| 26 | K | CB | 351 | 365 | 544 | 29 |
| 26 | K | CG | 363 | 375 | 544 | 41 |
| 26 | K | CD | 367 | 378 | 529 | 43 |
| 26 | K | CE | 372 | 392 | 528 | 40 |
| 26 | K | NZ | 370 | 396 | 514 | 41 |
| 27 | L | N | 324 | 375 | 560 | 23 |
| 27 | L | CA | 318 | 383 | 571 | 22 |
| 27 | L | C | 329 | 390 | 579 | 21 |
| 27 | L | O | 337 | 384 | 585 | 23 |
| 27 | L | CB | 310 | 374 | 580 | 23 |
| 27 | L | CG | 302 | 380 | 592 | 16 |
| 27 | L | CD1 | 293 | 391 | 588 | 14 |
| 27 | L | CD2 | 295 | 369 | 599 | 16 |
| 28 | P | N | 329 | 404 | 579 | 22 |
| 28 | P | CA | 338 | 411 | 587 | 23 |
| 28 | P | C | 335 | 408 | 601 | 23 |
| 28 | P | O | 324 | 407 | 605 | 22 |
| 28 | P | CB | 335 | 426 | 583 | 23 |
| 28 | P | CG | 327 | 425 | 571 | 25 |
| 28 | P | CD | 319 | 412 | 572 | 22 |
| 29 | I | N | 346 | 407 | 609 | 20 |
| 29 | I | CA | 344 | 403 | 623 | 19 |
| 29 | I | C | 350 | 414 | 633 | 23 |
| 29 | I | O | 362 | 417 | 632 | 24 |
| 29 | I | CB | 350 | 390 | 627 | 17 |
| 29 | I | CG1 | 342 | 379 | 619 | 20 |
| 29 | I | CG2 | 349 | 387 | 641 | 20 |
| 29 | I | CD1 | 328 | 377 | 622 | 12 |
| 30 | N | N | 342 | 419 | 642 | 22 |
| 30 | N | CA | 347 | 429 | 652 | 20 |
| 30 | N | C | 344 | 423 | 666 | 16 |
| 30 | N | O | 342 | 411 | 667 | 18 |
| 30 | N | CB | 341 | 443 | 650 | 18 |
| 30 | N | CG | 327 | 445 | 653 | 17 |
| 30 | N | OD1 | 320 | 435 | 657 | 20 |
| 30 | N | ND2 | 322 | 457 | 652 | 18 |
| 31 | A | N | 345 | 431 | 676 | 19 |
| 31 | A | CA | 342 | 426 | 690 | 20 |
| 31 | A | C | 328 | 423 | 693 | 22 |
| 31 | A | O | 325 | 415 | 702 | 23 |
| 31 | A | CB | 348 | 436 | 700 | 19 |
| 32 | I | N | 318 | 429 | 686 | 23 |
| 32 | I | CA | 304 | 427 | 688 | 23 |
| 32 | I | C | 298 | 415 | 681 | 23 |
| 32 | I | O | 288 | 410 | 685 | 26 |
| 32 | I | CB | 296 | 440 | 683 | 20 |
| 32 | I | CG | 301 | 453 | 689 | 23 |
| 32 | I | CD1 | 294 | 465 | 683 | 21 |
| 32 | I | CD2 | 298 | 453 | 704 | 29 |
| 33 | S | N | 305 | 411 | 670 | 23 |
| 33 | S | CA | 301 | 399 | 662 | 22 |
| 33 | S | C | 295 | 387 | 669 | 24 |
| 33 | S | O | 284 | 383 | 667 | 24 |
| 33 | S | CB | 312 | 395 | 653 | 18 |
| 33 | S | OG | 316 | 406 | 645 | 17 |
| 34 | N | N | 303 | 381 | 678 | 26 |
| 34 | N | CA | 299 | 369 | 685 | 25 |
| 34 | N | C | 287 | 369 | 695 | 23 |
| 34 | N | O | 281 | 359 | 698 | 22 |
| 34 | N | CB | 312 | 362 | 692 | 29 |
| 34 | N | CG | 322 | 357 | 682 | 35 |
| 34 | N | OD1 | 318 | 351 | 672 | 37 |
| 34 | N | ND2 | 334 | 358 | 685 | 40 |
| 35 | S | N | 284 | 381 | 700 | 22 |
| 35 | S | CA | 272 | 382 | 708 | 25 |
| 35 | S | C | 259 | 380 | 700 | 27 |
| 35 | S | O | 249 | 377 | 705 | 28 |
| 35 | S | CB | 271 | 396 | 715 | 23 |
| 35 | S | OG | 270 | 407 | 706 | 30 |
| 36 | L | N | 261 | 382 | 686 | 26 |
| 36 | L | CA | 249 | 379 | 677 | 24 |
| 36 | L | C | 250 | 366 | 669 | 24 |
| 36 | L | O | 241 | 358 | 669 | 26 |
| 36 | L | CB | 248 | 391 | 668 | 22 |
| 36 | L | CG | 237 | 390 | 656 | 20 |
| 36 | L | CD1 | 223 | 389 | 662 | 22 |
| 36 | L | CD2 | 238 | 401 | 647 | 19 |
| 37 | L | N | 262 | 364 | 663 | 23 |
| 37 | L | CA | 263 | 352 | 654 | 25 |
| 37 | L | C | 277 | 345 | 655 | 25 |
| 37 | L | O | 287 | 351 | 654 | 27 |
| 37 | L | CB | 261 | 356 | 640 | 21 |
| 37 | L | CG | 258 | 346 | 629 | 21 |
| 37 | L | CD1 | 247 | 352 | 619 | 18 |
| 37 | L | CD2 | 270 | 344 | 621 | 22 |
| 38 | R | N | 277 | 332 | 658 | 27 |
| 38 | R | CA | 289 | 324 | 659 | 31 |
| 38 | R | C | 294 | 317 | 647 | 30 |
| 38 | R | O | 306 | 315 | 644 | 27 |
| 38 | R | CB | 289 | 315 | 671 | 38 |
| 38 | R | CG | 289 | 322 | 684 | 47 |
| 38 | R | CD | 286 | 313 | 696 | 57 |
| 38 | R | NE | 294 | 316 | 708 | 68 |
| 38 | R | CZ | 296 | 307 | 717 | 73 |
| 38 | R | NH1 | 291 | 295 | 717 | 75 |
| 38 | R | NH2 | 304 | 311 | 728 | 75 |
| 39 | H | N | 284 | 312 | 639 | 29 |
| 39 | H | CA | 288 | 304 | 627 | 30 |
| 39 | H | C | 291 | 314 | 615 | 29 |
| 39 | H | O | 284 | 313 | 605 | 32 |
| 39 | H | CB | 276 | 295 | 623 | 28 |
| 39 | H | CG | 273 | 284 | 633 | 28 |
| 39 | H | ND1 | 263 | 275 | 632 | 32 |
| 39 | H | CD2 | 280 | 282 | 645 | 32 |
| 39 | H | CE1 | 263 | 267 | 642 | 33 |
| 39 | H | NE2 | 273 | 271 | 650 | 33 |
| 40 | H | N | 302 | 321 | 616 | 26 |
| 40 | H | CA | 306 | 331 | 606 | 29 |
| 40 | H | C | 307 | 326 | 591 | 29 |
| 40 | H | O | 305 | 334 | 582 | 27 |
| 40 | H | CB | 320 | 337 | 610 | 28 |
| 40 | H | CG | 320 | 342 | 624 | 33 |
| 40 | H | ND1 | 332 | 344 | 632 | 31 |
| 40 | H | CD2 | 310 | 346 | 633 | 33 |

TABLE 1-continued

| | | | | | |
|---|---|---|---|---|---|
| 40 H | CE1 | 329 | 348 | 644 | 32 |
| 40 H | NE2 | 316 | 349 | 645 | 32 |
| 41 N | N | 311 | 313 | 589 | 29 |
| 41 N | CA | 312 | 308 | 576 | 33 |
| 41 N | C | 299 | 305 | 569 | 34 |
| 41 N | O | 299 | 301 | 557 | 37 |
| 41 N | CB | 320 | 295 | 577 | 38 |
| 41 N | CG | 335 | 297 | 581 | 45 |
| 41 N | OD1 | 340 | 308 | 581 | 47 |
| 41 N | ND2 | 342 | 286 | 584 | 48 |
| 42 M | N | 288 | 308 | 575 | 35 |
| 42 M | CA | 275 | 307 | 569 | 33 |
| 42 M | C | 271 | 320 | 561 | 33 |
| 42 M | O | 263 | 319 | 552 | 33 |
| 42 M | CB | 265 | 304 | 579 | 38 |
| 42 M | CG | 267 | 292 | 588 | 41 |
| 42 M | SD | 262 | 275 | 579 | 57 |
| 42 M | CE | 242 | 278 | 576 | 48 |
| 43 V | N | 278 | 331 | 565 | 28 |
| 43 V | CA | 275 | 344 | 560 | 26 |
| 43 V | C | 285 | 349 | 549 | 26 |
| 43 V | O | 297 | 348 | 551 | 28 |
| 43 V | CB | 274 | 354 | 571 | 20 |
| 43 V | CG1 | 271 | 368 | 565 | 16 |
| 43 V | CG2 | 262 | 351 | 580 | 20 |
| 44 Y | N | 280 | 354 | 538 | 25 |
| 44 Y | CA | 288 | 359 | 527 | 24 |
| 44 Y | C | 281 | 370 | 520 | 23 |
| 44 Y | O | 269 | 372 | 520 | 21 |
| 44 Y | CB | 292 | 347 | 518 | 22 |
| 44 Y | CG | 280 | 343 | 509 | 25 |
| 44 Y | CD1 | 271 | 334 | 514 | 26 |
| 44 Y | CD2 | 278 | 348 | 496 | 25 |
| 44 Y | CE1 | 260 | 330 | 507 | 24 |
| 44 Y | CE2 | 267 | 344 | 489 | 22 |
| 44 Y | CZ | 258 | 335 | 494 | 25 |
| 44 Y | OH | 246 | 331 | 487 | 27 |
| 45 A | N | 289 | 378 | 513 | 21 |
| 45 A | CA | 284 | 389 | 504 | 23 |
| 45 A | C | 287 | 384 | 490 | 27 |
| 45 A | O | 297 | 377 | 487 | 30 |
| 45 A | CB | 290 | 402 | 507 | 16 |
| 46 T | N | 277 | 387 | 481 | 24 |
| 46 T | CA | 280 | 383 | 467 | 21 |
| 46 T | C | 289 | 394 | 462 | 22 |
| 46 T | O | 289 | 405 | 466 | 24 |
| 46 T | CB | 267 | 384 | 458 | 15 |
| 46 T | OG1 | 261 | 397 | 460 | 17 |
| 46 T | CG2 | 258 | 373 | 462 | 17 |
| 47 T | N | 297 | 390 | 452 | 26 |
| 47 T | CA | 307 | 400 | 446 | 26 |
| 47 T | C | 308 | 398 | 431 | 25 |
| 47 T | O | 303 | 388 | 425 | 23 |
| 47 T | CB | 321 | 396 | 453 | 25 |
| 47 T | OG1 | 330 | 407 | 452 | 33 |
| 47 T | CG2 | 327 | 384 | 446 | 22 |
| 48 S | N | 314 | 408 | 424 | 26 |
| 48 S | CA | 315 | 407 | 409 | 26 |
| 48 S | C | 322 | 395 | 404 | 29 |
| 48 S | O | 320 | 391 | 393 | 31 |
| 48 S | CB | 322 | 420 | 404 | 24 |
| 48 S | OG | 336 | 419 | 407 | 26 |
| 49 R | N | 329 | 388 | 413 | 29 |
| 49 R | CA | 336 | 376 | 410 | 27 |
| 49 R | C | 327 | 365 | 405 | 28 |
| 49 R | O | 332 | 355 | 399 | 28 |
| 49 R | CB | 345 | 371 | 421 | 32 |
| 49 R | CG | 357 | 380 | 425 | 35 |
| 49 R | CD | 367 | 374 | 434 | 42 |
| 49 R | NE | 363 | 374 | 448 | 52 |
| 49 R | CZ | 364 | 385 | 456 | 54 |
| 49 R | NH1 | 369 | 396 | 451 | 55 |
| 49 R | NH2 | 361 | 384 | 469 | 55 |
| 50 S | N | 314 | 366 | 407 | 26 |
| 50 S | CA | 304 | 356 | 402 | 26 |
| 50 S | C | 295 | 362 | 392 | 24 |
| 50 S | O | 285 | 356 | 388 | 22 |
| 50 S | CB | 296 | 350 | 414 | 26 |
| 50 S | OG | 287 | 360 | 419 | 29 |
| 51 A | N | 298 | 374 | 386 | 25 |
| 51 A | CA | 290 | 381 | 376 | 26 |
| 51 A | C | 288 | 372 | 364 | 28 |
| 51 A | O | 277 | 372 | 357 | 27 |
| 51 A | CB | 296 | 394 | 373 | 18 |
| 52 G | N | 299 | 364 | 360 | 30 |
| 52 G | CA | 299 | 355 | 349 | 27 |
| 52 G | C | 287 | 345 | 350 | 29 |
| 52 G | O | 280 | 343 | 340 | 29 |
| 53 L | N | 286 | 339 | 362 | 29 |
| 53 L | CA | 276 | 329 | 364 | 30 |
| 53 L | C | 262 | 335 | 363 | 29 |
| 53 L | O | 253 | 329 | 358 | 30 |
| 53 L | CB | 278 | 324 | 378 | 32 |
| 53 L | CG | 287 | 312 | 380 | 34 |
| 53 L | CD1 | 290 | 310 | 394 | 34 |
| 53 L | CD2 | 281 | 300 | 373 | 35 |
| 54 R | N | 260 | 348 | 368 | 27 |
| 54 R | CA | 248 | 355 | 367 | 27 |
| 54 R | C | 244 | 357 | 352 | 26 |
| 54 R | O | 233 | 354 | 348 | 23 |
| 54 R | CB | 248 | 368 | 375 | 26 |
| 54 R | CG | 235 | 376 | 374 | 26 |
| 54 R | CD | 223 | 369 | 379 | 28 |
| 54 R | NE | 223 | 364 | 393 | 34 |
| 54 R | CZ | 214 | 357 | 398 | 35 |
| 54 R | NH1 | 204 | 353 | 391 | 35 |
| 54 R | NH2 | 215 | 353 | 411 | 31 |
| 55 Q | N | 254 | 362 | 345 | 28 |
| 55 Q | CA | 253 | 365 | 331 | 29 |
| 55 Q | C | 247 | 353 | 324 | 29 |
| 55 Q | O | 238 | 354 | 315 | 29 |
| 55 Q | CB | 266 | 369 | 324 | 24 |
| 55 Q | CG | 271 | 383 | 326 | 25 |
| 55 Q | CD | 285 | 386 | 321 | 30 |
| 55 Q | OE1 | 287 | 394 | 312 | 30 |
| 55 Q | NE2 | 294 | 379 | 327 | 35 |
| 56 K | N | 251 | 341 | 327 | 29 |
| 56 K | CA | 247 | 329 | 321 | 31 |
| 56 K | C | 232 | 325 | 325 | 34 |
| 56 K | O | 225 | 320 | 316 | 37 |
| 56 K | CB | 256 | 317 | 325 | 32 |
| 56 K | CG | 270 | 319 | 320 | 37 |
| 56 K | CD | 279 | 307 | 324 | 41 |
| 56 K | CE | 293 | 309 | 317 | 45 |
| 56 K | NZ | 291 | 309 | 302 | 44 |
| 57 K | N | 228 | 328 | 337 | 35 |
| 57 K | CA | 214 | 325 | 341 | 33 |
| 57 K | C | 204 | 335 | 334 | 28 |
| 57 K | O | 194 | 331 | 329 | 33 |
| 57 K | CB | 212 | 326 | 356 | 34 |
| 57 K | CG | 221 | 316 | 364 | 44 |
| 57 K | CD | 217 | 316 | 379 | 49 |
| 57 K | CE | 227 | 307 | 387 | 49 |
| 57 K | NZ | 228 | 294 | 381 | 54 |
| 58 V | N | 207 | 348 | 334 | 26 |
| 58 V | CA | 199 | 358 | 328 | 24 |
| 58 V | C | 199 | 359 | 313 | 23 |
| 58 V | O | 190 | 366 | 307 | 22 |
| 58 V | CB | 202 | 372 | 334 | 23 |
| 58 V | CG1 | 202 | 372 | 349 | 23 |
| 58 V | CG2 | 216 | 377 | 330 | 22 |
| 59 T | N | 207 | 352 | 306 | 25 |
| 59 T | CA | 208 | 353 | 291 | 24 |
| 59 T | C | 201 | 341 | 284 | 24 |
| 59 T | O | 206 | 330 | 285 | 24 |
| 59 T | CB | 223 | 353 | 286 | 23 |
| 59 T | OG1 | 229 | 364 | 293 | 23 |
| 59 T | CG2 | 223 | 356 | 271 | 22 |
| 60 F | N | 190 | 344 | 278 | 24 |
| 60 F | CA | 182 | 334 | 271 | 25 |
| 60 F | C | 173 | 341 | 260 | 23 |
| 60 F | O | 172 | 353 | 260 | 23 |
| 60 F | CB | 174 | 325 | 280 | 28 |
| 60 F | CG | 165 | 333 | 291 | 32 |
| 60 F | CD1 | 152 | 337 | 287 | 31 |
| 60 F | CD2 | 170 | 335 | 303 | 31 |
| 60 F | CE1 | 144 | 344 | 297 | 28 |
| 60 F | CE2 | 162 | 342 | 313 | 34 |

TABLE 1-continued

| | | | | | |
|---|---|---|---|---|---|
| 60 F | CZ | 149 | 346 | 310 | 35 |
| 61 D | N | 168 | 332 | 251 | 26 |
| 61 D | CA | 159 | 337 | 240 | 29 |
| 61 D | C | 145 | 336 | 245 | 27 |
| 61 D | O | 141 | 326 | 251 | 29 |
| 61 D | CB | 162 | 328 | 228 | 34 |
| 61 D | CG | 154 | 332 | 216 | 41 |
| 61 D | OD1 | 155 | 344 | 211 | 44 |
| 61 D | OD2 | 146 | 324 | 210 | 45 |
| 62 R | N | 137 | 346 | 242 | 26 |
| 62 R | CA | 123 | 345 | 246 | 25 |
| 62 R | C | 113 | 346 | 235 | 25 |
| 62 R | O | 115 | 352 | 224 | 23 |
| 62 R | CB | 119 | 355 | 258 | 23 |
| 62 R | CG | 125 | 368 | 257 | 26 |
| 62 R | CD | 139 | 369 | 260 | 21 |
| 62 R | NE | 142 | 381 | 268 | 25 |
| 62 R | CZ | 141 | 393 | 263 | 23 |
| 62 R | NH1 | 139 | 395 | 250 | 31 |
| 62 R | NH2 | 141 | 404 | 271 | 29 |
| 63 L | N | 102 | 338 | 237 | 27 |
| 63 L | CA | 91 | 338 | 227 | 26 |
| 63 L | C | 78 | 341 | 234 | 23 |
| 63 L | O | 76 | 337 | 246 | 25 |
| 63 L | CB | 90 | 324 | 221 | 28 |
| 63 L | CG | 103 | 319 | 214 | 30 |
| 63 L | CD1 | 101 | 304 | 211 | 33 |
| 63 L | CD2 | 105 | 327 | 201 | 31 |
| 64 Q | N | 69 | 348 | 228 | 24 |
| 64 Q | CA | 56 | 351 | 233 | 20 |
| 64 Q | C | 45 | 348 | 223 | 21 |
| 64 Q | O | 45 | 352 | 212 | 18 |
| 64 Q | CB | 55 | 366 | 237 | 19 |
| 64 Q | CG | 61 | 369 | 250 | 22 |
| 64 Q | CD | 58 | 383 | 253 | 23 |
| 64 Q | OE1 | 60 | 393 | 245 | 25 |
| 64 Q | NE2 | 53 | 386 | 266 | 24 |
| 65 V | N | 34 | 341 | 228 | 22 |
| 65 V | CA | 23 | 338 | 220 | 23 |
| 65 V | C | 11 | 345 | 228 | 22 |
| 65 V | O | 7 | 341 | 239 | 23 |
| 65 V | CB | 21 | 322 | 220 | 23 |
| 65 V | CG1 | 8 | 319 | 214 | 24 |
| 65 V | CG2 | 33 | 316 | 212 | 23 |
| 66 L | N | 7 | 356 | 222 | 19 |
| 66 L | CA | −3 | 364 | 227 | 20 |
| 66 L | C | −17 | 361 | 223 | 20 |
| 66 L | O | −20 | 362 | 211 | 21 |
| 66 L | CB | 0 | 379 | 225 | 18 |
| 66 L | CG | 11 | 385 | 234 | 17 |
| 66 L | CD1 | 20 | 375 | 240 | 18 |
| 66 L | CD2 | 18 | 396 | 228 | 10 |
| 67 D | N | −25 | 357 | 232 | 19 |
| 67 D | CA | −39 | 353 | 228 | 20 |
| 67 D | C | −50 | 364 | 232 | 17 |
| 67 D | O | −47 | 375 | 236 | 15 |
| 67 D | CB | −43 | 339 | 234 | 20 |
| 67 D | CG | −44 | 339 | 249 | 20 |
| 67 D | OD1 | −41 | 349 | 256 | 18 |
| 67 D | OD2 | −47 | 328 | 255 | 28 |
| 68 D | N | −63 | 359 | 230 | 19 |
| 68 D | CA | −74 | 368 | 233 | 20 |
| 68 D | C | −76 | 372 | 247 | 17 |
| 68 D | O | −79 | 384 | 250 | 17 |
| 68 D | CB | −87 | 362 | 228 | 23 |
| 68 D | CG | −88 | 364 | 213 | 22 |
| 68 D | OD1 | −91 | 375 | 208 | 27 |
| 68 D | OD2 | −86 | 354 | 205 | 21 |
| 69 H | N | −73 | 363 | 257 | 17 |
| 69 H | CA | −74 | 366 | 271 | 19 |
| 69 H | C | −63 | 377 | 274 | 20 |
| 69 H | O | −66 | 387 | 282 | 20 |
| 69 H | CB | −71 | 354 | 280 | 20 |
| 69 H | CG | −83 | 344 | 280 | 21 |
| 69 H | ND1 | −81 | 331 | 279 | 20 |
| 69 H | CD2 | −96 | 347 | 282 | 19 |
| 69 H | CE1 | −93 | 325 | 280 | 21 |
| 69 H | NE2 | −102 | 334 | 282 | 22 |
| 70 Y | N | −52 | 377 | 268 | 19 |
| 70 Y | CA | −41 | 387 | 270 | 16 |
| 70 Y | C | −46 | 400 | 265 | 17 |
| 70 Y | O | −45 | 410 | 273 | 19 |
| 70 Y | CB | −28 | 382 | 263 | 18 |
| 70 Y | CG | −17 | 392 | 263 | 19 |
| 70 Y | CD1 | −16 | 403 | 254 | 20 |
| 70 Y | CD2 | −7 | 392 | 273 | 18 |
| 70 Y | CE1 | −5 | 412 | 255 | 19 |
| 70 Y | CE2 | 3 | 401 | 274 | 17 |
| 70 Y | CZ | 3 | 411 | 265 | 17 |
| 70 Y | OH | 13 | 421 | 266 | 19 |
| 71 R | N | −51 | 401 | 253 | 18 |
| 71 R | CA | −57 | 414 | 248 | 19 |
| 71 R | C | −69 | 419 | 255 | 16 |
| 71 R | O | −71 | 431 | 256 | 16 |
| 71 R | CB | −59 | 414 | 232 | 22 |
| 71 R | CG | −47 | 413 | 224 | 21 |
| 71 R | CD | −50 | 412 | 209 | 18 |
| 71 R | NE | −58 | 400 | 206 | 17 |
| 71 R | CZ | −52 | 388 | 204 | 18 |
| 71 R | NH1 | −39 | 386 | 204 | 20 |
| 71 R | NH2 | −60 | 377 | 202 | 19 |
| 72 D | N | −78 | 410 | 260 | 18 |
| 72 D | CA | −90 | 414 | 267 | 18 |
| 72 D | C | −86 | 421 | 280 | 20 |
| 72 D | O | −92 | 431 | 284 | 18 |
| 72 D | CB | −98 | 401 | 271 | 19 |
| 72 D | CG | −106 | 396 | 259 | 21 |
| 72 D | OD1 | −108 | 403 | 249 | 23 |
| 72 D | OD2 | −111 | 384 | 260 | 24 |
| 73 V | N | −77 | 415 | 288 | 18 |
| 73 V | CA | −73 | 420 | 301 | 17 |
| 73 V | C | −66 | 434 | 298 | 17 |
| 73 V | O | −69 | 444 | 305 | 14 |
| 73 V | CB | −63 | 411 | 308 | 17 |
| 73 V | CG1 | −57 | 417 | 320 | 15 |
| 73 V | CG2 | −70 | 398 | 313 | 15 |
| 74 L | N | −57 | 435 | 288 | 14 |
| 74 L | CA | −50 | 447 | 285 | 14 |
| 74 L | C | −60 | 458 | 282 | 15 |
| 74 L | O | −58 | 470 | 286 | 15 |
| 74 L | CB | −40 | 446 | 273 | 16 |
| 74 L | CG | −33 | 458 | 268 | 16 |
| 74 L | CD1 | −25 | 465 | 279 | 13 |
| 74 L | CD2 | −23 | 454 | 257 | 17 |
| 75 K | N | −71 | 455 | 274 | 17 |
| 75 K | CA | −81 | 465 | 271 | 18 |
| 75 K | C | −88 | 471 | 283 | 13 |
| 75 K | O | −90 | 482 | 284 | 17 |
| 75 K | CB | −91 | 460 | 261 | 19 |
| 75 K | CG | −99 | 472 | 255 | 20 |
| 75 K | CD | −110 | 467 | 245 | 22 |
| 75 K | CE | −116 | 479 | 238 | 27 |
| 75 K | NZ | −126 | 475 | 229 | 30 |
| 76 E | N | −90 | 462 | 293 | 16 |
| 76 E | CA | −96 | 466 | 305 | 20 |
| 76 E | C | −87 | 475 | 313 | 17 |
| 76 E | O | −91 | 485 | 319 | 19 |
| 76 E | CB | −100 | 454 | 314 | 22 |
| 76 E | CG | −110 | 445 | 307 | 30 |
| 76 E | CD | −112 | 432 | 314 | 32 |
| 76 E | OE1 | −108 | 431 | 326 | 35 |
| 76 E | OE2 | −116 | 422 | 307 | 35 |
| 77 M | N | −74 | 472 | 313 | 16 |
| 77 M | CA | −64 | 480 | 321 | 16 |
| 77 M | C | −63 | 494 | 315 | 16 |
| 77 M | O | −63 | 503 | 323 | 15 |
| 77 M | CB | −51 | 473 | 321 | 17 |
| 77 M | CG | −50 | 461 | 330 | 18 |
| 77 M | SD | −34 | 449 | 327 | 20 |
| 77 M | CE | −19 | 461 | 335 | 20 |
| 78 K | N | −62 | 495 | 302 | 17 |
| 78 K | CA | −61 | 508 | 296 | 16 |
| 78 K | C | −74 | 516 | 298 | 18 |
| 78 K | O | −72 | 529 | 300 | 17 |
| 78 K | CB | −59 | 506 | 281 | 17 |
| 78 K | CG | −46 | 500 | 277 | 16 |
| 78 K | CD | −43 | 503 | 262 | 23 |
| 78 K | CE | −33 | 494 | 256 | 30 |

TABLE 1-continued

| | | | | | |
|---|---|---|---|---|---|
| 78 K | NZ | −32 | 497 | 242 | 33 |
| 79 A | N | −86 | 510 | 299 | 20 |
| 79 A | CA | −98 | 518 | 302 | 19 |
| 79 A | C | −97 | 525 | 316 | 17 |
| 79 A | O | −101 | 537 | 317 | 16 |
| 79 A | CB | −110 | 509 | 301 | 14 |
| 80 K | N | −91 | 518 | 325 | 18 |
| 80 K | CA | −88 | 523 | 339 | 18 |
| 80 K | C | −77 | 534 | 338 | 18 |
| 80 K | O | −78 | 545 | 344 | 18 |
| 80 K | CB | −85 | 512 | 348 | 19 |
| 80 K | CG | −97 | 504 | 352 | 23 |
| 80 K | CD | −92 | 492 | 360 | 30 |
| 80 K | CE | −104 | 484 | 365 | 35 |
| 80 K | NZ | −115 | 493 | 371 | 41 |
| 81 A | N | −66 | 531 | 331 | 18 |
| 81 A | CA | −55 | 540 | 330 | 19 |
| 81 A | C | −59 | 554 | 324 | 21 |
| 81 A | O | −54 | 564 | 326 | 18 |
| 81 A | CB | −43 | 534 | 321 | 18 |
| 82 S | N | −70 | 553 | 316 | 22 |
| 82 S | CA | −75 | 565 | 309 | 22 |
| 82 S | C | −81 | 575 | 319 | 21 |
| 82 S | O | −83 | 587 | 316 | 21 |
| 82 S | CB | −85 | 562 | 298 | 24 |
| 82 S | OG | −79 | 555 | 288 | 35 |
| 83 T | N | −85 | 571 | 331 | 22 |
| 83 T | CA | −90 | 580 | 341 | 20 |
| 83 T | C | −79 | 587 | 349 | 19 |
| 83 T | O | −82 | 597 | 356 | 21 |
| 83 T | CB | −100 | 573 | 351 | 23 |
| 83 T | OG1 | −92 | 563 | 359 | 22 |
| 83 T | CG2 | −110 | 565 | 343 | 22 |
| 84 V | N | −67 | 583 | 348 | 18 |
| 84 V | CA | −56 | 589 | 355 | 17 |
| 84 V | C | −51 | 602 | 348 | 17 |
| 84 V | O | −51 | 603 | 336 | 21 |
| 84 V | CB | −43 | 579 | 355 | 16 |
| 84 V | CG1 | −31 | 586 | 361 | 12 |
| 84 V | CG2 | −47 | 566 | 362 | 13 |
| 85 K | N | −48 | 612 | 357 | 17 |
| 85 K | CA | −43 | 625 | 352 | 19 |
| 85 K | C | −30 | 626 | 360 | 22 |
| 85 K | O | −30 | 626 | 372 | 20 |
| 85 K | CB | −52 | 637 | 355 | 21 |
| 85 K | CG | −47 | 650 | 350 | 21 |
| 85 K | CD | −57 | 661 | 350 | 26 |
| 85 K | CE | −50 | 674 | 344 | 31 |
| 85 K | NZ | −60 | 685 | 343 | 39 |
| 86 A | N | −19 | 627 | 352 | 21 |
| 86 A | CA | −6 | 629 | 359 | 19 |
| 86 A | C | 0 | 642 | 356 | 22 |
| 86 A | O | −1 | 647 | 345 | 24 |
| 86 A | CB | 2 | 617 | 355 | 21 |
| 87 K | N | 8 | 647 | 365 | 21 |
| 87 K | CA | 14 | 660 | 364 | 24 |
| 87 K | C | 29 | 658 | 361 | 22 |
| 87 K | O | 35 | 648 | 365 | 21 |
| 87 K | CB | 13 | 668 | 376 | 30 |
| 87 K | CG | 0 | 668 | 383 | 42 |
| 87 K | CD | −12 | 675 | 375 | 48 |
| 87 K | CE | −12 | 690 | 376 | 53 |
| 87 K | NZ | −2 | 697 | 367 | 56 |
| 88 L | N | 36 | 668 | 355 | 20 |
| 88 L | CA | 50 | 668 | 352 | 23 |
| 88 L | C | 56 | 674 | 365 | 24 |
| 88 L | O | 51 | 684 | 370 | 26 |
| 88 L | CB | 52 | 677 | 340 | 24 |
| 88 L | CG | 64 | 675 | 330 | 24 |
| 88 L | CD1 | 66 | 661 | 325 | 20 |
| 88 L | CD2 | 60 | 684 | 318 | 26 |
| 89 L | N | 67 | 668 | 370 | 22 |
| 89 L | CA | 74 | 674 | 381 | 23 |
| 89 L | C | 84 | 685 | 376 | 23 |
| 89 L | O | 90 | 684 | 366 | 27 |
| 89 L | CB | 82 | 663 | 389 | 23 |
| 89 L | CG | 78 | 657 | 402 | 23 |
| 89 L | CD1 | 63 | 653 | 401 | 18 |
| 89 L | CD2 | 87 | 646 | 405 | 20 |
| 90 S | N | 86 | 696 | 384 | 23 |
| 90 S | CA | 95 | 706 | 380 | 23 |
| 90 S | C | 110 | 701 | 383 | 23 |
| 90 S | O | 111 | 690 | 388 | 21 |
| 90 S | CB | 93 | 719 | 389 | 23 |
| 90 S | OG | 95 | 716 | 403 | 26 |
| 91 V | N | 120 | 708 | 379 | 25 |
| 91 V | CA | 134 | 704 | 381 | 26 |
| 91 V | C | 137 | 703 | 396 | 26 |
| 91 V | O | 142 | 693 | 401 | 25 |
| 91 V | CB | 144 | 712 | 374 | 23 |
| 91 V | CG1 | 158 | 707 | 376 | 23 |
| 91 V | CG2 | 141 | 713 | 359 | 28 |
| 92 E | N | 133 | 713 | 403 | 28 |
| 92 E | CA | 135 | 714 | 418 | 31 |
| 92 E | C | 128 | 702 | 425 | 28 |
| 92 E | O | 134 | 696 | 434 | 27 |
| 92 E | CB | 131 | 727 | 424 | 34 |
| 92 E | CG | 118 | 734 | 418 | 47 |
| 92 E | CD | 121 | 744 | 407 | 52 |
| 92 E | OE1 | 127 | 741 | 396 | 52 |
| 92 E | OE2 | 116 | 756 | 409 | 53 |
| 93 E | N | 116 | 699 | 421 | 27 |
| 93 E | CA | 109 | 687 | 427 | 23 |
| 93 E | C | 116 | 674 | 425 | 21 |
| 93 E | O | 117 | 666 | 434 | 21 |
| 93 E | CB | 94 | 687 | 423 | 25 |
| 93 E | CG | 86 | 699 | 427 | 32 |
| 93 E | CD | 72 | 698 | 423 | 37 |
| 93 E | OE1 | 69 | 695 | 411 | 39 |
| 93 E | OE2 | 63 | 700 | 431 | 40 |
| 94 A | N | 120 | 671 | 412 | 21 |
| 94 A | CA | 127 | 659 | 409 | 19 |
| 94 A | C | 140 | 658 | 416 | 17 |
| 94 A | O | 145 | 648 | 420 | 20 |
| 94 A | CB | 128 | 657 | 394 | 20 |
| 95 C | N | 147 | 670 | 417 | 18 |
| 95 C | CA | 160 | 670 | 424 | 20 |
| 95 C | C | 159 | 666 | 439 | 20 |
| 95 C | O | 168 | 659 | 444 | 21 |
| 95 C | CB | 166 | 684 | 423 | 15 |
| 95 C | SG | 172 | 689 | 406 | 25 |
| 96 K | N | 149 | 671 | 445 | 23 |
| 96 K | CA | 146 | 668 | 460 | 24 |
| 96 K | C | 143 | 654 | 462 | 25 |
| 96 K | O | 143 | 650 | 474 | 27 |
| 96 K | CB | 135 | 677 | 465 | 26 |
| 96 K | CG | 137 | 692 | 465 | 34 |
| 96 K | CD | 126 | 700 | 471 | 45 |
| 96 K | CE | 114 | 700 | 462 | 49 |
| 96 K | NZ | 106 | 713 | 464 | 46 |
| 97 L | N | 140 | 646 | 452 | 22 |
| 97 L | CA | 137 | 632 | 453 | 19 |
| 97 L | C | 150 | 623 | 452 | 16 |
| 97 L | O | 149 | 611 | 453 | 17 |
| 97 L | CB | 127 | 628 | 443 | 20 |
| 97 L | CG | 112 | 632 | 445 | 20 |
| 97 L | CD1 | 105 | 629 | 432 | 17 |
| 97 L | CD2 | 106 | 624 | 456 | 16 |
| 98 T | N | 161 | 629 | 449 | 22 |
| 98 T | CA | 174 | 622 | 447 | 21 |
| 98 T | C | 181 | 619 | 460 | 19 |
| 98 T | O | 183 | 628 | 468 | 20 |
| 98 T | CB | 183 | 632 | 437 | 23 |
| 98 T | OG1 | 176 | 634 | 425 | 20 |
| 98 T | CG2 | 197 | 626 | 435 | 18 |
| 99 P | N | 185 | 606 | 462 | 19 |
| 99 P | CA | 192 | 602 | 474 | 19 |
| 99 P | C | 205 | 610 | 475 | 25 |
| 99 P | O | 212 | 612 | 466 | 25 |
| 99 P | CB | 195 | 587 | 472 | 17 |
| 99 P | CG | 183 | 583 | 464 | 18 |
| 99 P | CD | 182 | 594 | 454 | 17 |
| 100 P | N | 208 | 614 | 488 | 27 |
| 100 P | CA | 221 | 622 | 490 | 29 |
| 100 P | C | 233 | 615 | 485 | 28 |
| 100 P | O | 243 | 621 | 481 | 32 |
| 100 P | CB | 221 | 624 | 505 | 28 |
| 100 P | CG | 207 | 625 | 508 | 28 |

TABLE 1-continued

| | | | | | |
|---|---|---|---|---|---|
| 100 P | CD | 201 | 613 | 500 | 28 |
| 101 H | N | 233 | 601 | 485 | 30 |
| 101 H | CA | 244 | 593 | 480 | 31 |
| 101 H | C | 242 | 586 | 467 | 30 |
| 101 H | O | 248 | 575 | 465 | 30 |
| 101 H | CB | 249 | 584 | 492 | 38 |
| 101 H | CG | 256 | 591 | 503 | 46 |
| 101 H | ND1 | 251 | 593 | 516 | 46 |
| 101 H | CD2 | 268 | 598 | 503 | 49 |
| 101 H | CE1 | 259 | 600 | 523 | 50 |
| 101 H | NE2 | 270 | 603 | 516 | 51 |
| 102 S | N | 234 | 591 | 459 | 28 |
| 102 S | CA | 231 | 585 | 446 | 25 |
| 102 S | C | 244 | 586 | 437 | 25 |
| 102 S | O | 251 | 596 | 439 | 25 |
| 102 S | CB | 219 | 593 | 439 | 23 |
| 102 S | OG | 215 | 587 | 427 | 22 |
| 103 A | N | 247 | 576 | 429 | 23 |
| 103 A | CA | 259 | 576 | 421 | 21 |
| 103 A | C | 260 | 590 | 413 | 24 |
| 103 A | O | 250 | 594 | 406 | 22 |
| 103 A | CB | 258 | 565 | 411 | 19 |
| 104 K | N | 272 | 596 | 414 | 23 |
| 104 K | CA | 274 | 609 | 407 | 24 |
| 104 K | C | 274 | 608 | 392 | 21 |
| 104 K | O | 276 | 597 | 386 | 20 |
| 104 K | CB | 288 | 615 | 411 | 25 |
| 104 K | CG | 300 | 606 | 407 | 30 |
| 104 K | CD | 313 | 614 | 408 | 37 |
| 104 K | CE | 325 | 605 | 404 | 39 |
| 104 K | NZ | 338 | 612 | 405 | 43 |
| 105 S | N | 272 | 619 | 385 | 22 |
| 105 S | CA | 271 | 620 | 371 | 25 |
| 105 S | C | 285 | 619 | 364 | 28 |
| 105 S | O | 295 | 623 | 370 | 28 |
| 105 S | CB | 264 | 633 | 367 | 24 |
| 105 S | OG | 264 | 635 | 353 | 23 |
| 106 K | N | 286 | 614 | 352 | 27 |
| 106 K | CA | 298 | 613 | 345 | 27 |
| 106 K | C | 302 | 627 | 340 | 27 |
| 106 K | O | 313 | 629 | 335 | 30 |
| 106 K | CB | 297 | 603 | 333 | 29 |
| 106 K | CG | 294 | 589 | 336 | 40 |
| 106 K | CD | 294 | 580 | 323 | 44 |
| 106 K | CE | 290 | 566 | 326 | 48 |
| 106 K | NZ | 293 | 557 | 315 | 50 |
| 107 F | N | 292 | 636 | 341 | 28 |
| 107 F | CA | 294 | 650 | 336 | 24 |
| 107 F | C | 298 | 661 | 346 | 26 |
| 107 F | O | 294 | 672 | 344 | 27 |
| 107 F | CB | 282 | 653 | 327 | 25 |
| 107 F | CG | 278 | 643 | 317 | 23 |
| 107 F | CD1 | 286 | 643 | 305 | 24 |
| 107 F | CD2 | 269 | 633 | 319 | 21 |
| 107 F | CE1 | 283 | 632 | 296 | 23 |
| 107 F | CE2 | 267 | 623 | 310 | 19 |
| 107 F | CZ | 274 | 623 | 299 | 24 |
| 108 G | N | 305 | 657 | 356 | 28 |
| 108 G | CA | 310 | 667 | 366 | 27 |
| 108 G | C | 301 | 673 | 377 | 26 |
| 108 G | O | 303 | 685 | 380 | 24 |
| 109 Y | N | 293 | 665 | 383 | 28 |
| 109 Y | CA | 284 | 669 | 394 | 23 |
| 109 Y | C | 278 | 657 | 400 | 21 |
| 109 Y | O | 278 | 646 | 393 | 22 |
| 109 Y | CB | 273 | 679 | 389 | 26 |
| 109 Y | CG | 262 | 673 | 380 | 27 |
| 109 Y | CD1 | 251 | 666 | 386 | 28 |
| 109 Y | CD2 | 263 | 674 | 366 | 25 |
| 109 Y | CE1 | 241 | 661 | 378 | 27 |
| 109 Y | CE2 | 254 | 668 | 358 | 25 |
| 109 Y | CZ | 243 | 662 | 364 | 27 |
| 109 Y | OH | 233 | 656 | 356 | 25 |
| 110 G | N | 274 | 658 | 412 | 22 |
| 110 G | CA | 268 | 646 | 419 | 23 |
| 110 G | C | 255 | 649 | 426 | 22 |
| 110 G | O | 250 | 660 | 424 | 23 |
| 111 A | N | 250 | 639 | 433 | 22 |
| 111 A | CA | 237 | 640 | 441 | 22 |
| 111 A | C | 236 | 652 | 450 | 28 |
| 111 A | O | 226 | 658 | 451 | 29 |
| 111 A | CB | 235 | 627 | 448 | 19 |
| 112 K | N | 247 | 656 | 456 | 34 |
| 112 K | CA | 247 | 667 | 465 | 35 |
| 112 K | C | 245 | 680 | 457 | 34 |
| 112 K | O | 239 | 690 | 462 | 32 |
| 112 K | CB | 259 | 668 | 474 | 41 |
| 112 K | CG | 261 | 656 | 484 | 49 |
| 112 K | CD | 248 | 655 | 493 | 52 |
| 112 K | CE | 249 | 643 | 502 | 57 |
| 112 K | NZ | 262 | 642 | 511 | 59 |
| 113 D | N | 251 | 680 | 445 | 32 |
| 113 D | CA | 250 | 692 | 436 | 29 |
| 113 D | C | 236 | 692 | 431 | 26 |
| 113 D | O | 230 | 703 | 429 | 26 |
| 113 D | CB | 260 | 690 | 425 | 31 |
| 113 D | CG | 274 | 690 | 429 | 33 |
| 113 D | OD1 | 278 | 699 | 437 | 36 |
| 113 D | OD2 | 282 | 681 | 425 | 31 |
| 114 V | N | 230 | 681 | 428 | 26 |
| 114 V | CA | 216 | 679 | 423 | 24 |
| 114 V | C | 206 | 684 | 434 | 24 |
| 114 V | O | 199 | 694 | 431 | 22 |
| 114 V | CB | 213 | 664 | 419 | 22 |
| 114 V | CG1 | 198 | 663 | 417 | 19 |
| 114 V | CG2 | 221 | 660 | 407 | 18 |
| 115 R | N | 207 | 678 | 446 | 22 |
| 115 R | CA | 198 | 682 | 457 | 25 |
| 115 R | C | 200 | 697 | 461 | 27 |
| 115 R | O | 190 | 704 | 465 | 27 |
| 115 R | CB | 200 | 674 | 469 | 25 |
| 115 R | CG | 198 | 659 | 467 | 22 |
| 115 R | CD | 200 | 651 | 480 | 25 |
| 115 R | NE | 193 | 658 | 491 | 25 |
| 115 R | CZ | 179 | 657 | 493 | 25 |
| 115 R | NH1 | 172 | 649 | 485 | 29 |
| 115 R | NH2 | 173 | 665 | 502 | 26 |
| 116 N | N | 212 | 703 | 459 | 29 |
| 116 N | CA | 215 | 717 | 462 | 31 |
| 116 N | C | 211 | 726 | 450 | 31 |
| 116 N | O | 212 | 739 | 452 | 28 |
| 116 N | CB | 230 | 718 | 464 | 36 |
| 116 N | CG | 234 | 716 | 479 | 43 |
| 116 N | OD1 | 229 | 724 | 487 | 47 |
| 116 N | ND2 | 243 | 707 | 482 | 44 |
| 117 L | N | 207 | 721 | 439 | 30 |
| 117 LI | CA | 202 | 728 | 427 | 29 |
| 117 LI | C | 213 | 737 | 421 | 29 |
| 117 LI | O | 211 | 748 | 416 | 30 |
| 117 LI | CB | 190 | 737 | 431 | 26 |
| 117 LI | CG | 178 | 730 | 438 | 22 |
| 117 LI | CD1 | 167 | 740 | 441 | 24 |
| 117 LI | CD2 | 173 | 718 | 430 | 20 |
| 118 S | N | 226 | 732 | 421 | 29 |
| 118 S | CA | 237 | 740 | 416 | 31 |
| 118 S | C | 235 | 742 | 401 | 32 |
| 118 S | O | 230 | 733 | 394 | 32 |
| 118 S | CB | 250 | 733 | 418 | 33 |
| 118 S | OG | 252 | 722 | 409 | 36 |
| 119 S | N | 239 | 754 | 396 | 33 |
| 119 S | CA | 238 | 757 | 382 | 33 |
| 119 S | C | 243 | 747 | 372 | 30 |
| 119 S | O | 238 | 744 | 362 | 29 |
| 119 S | CB | 243 | 771 | 379 | 36 |
| 119 S | OG | 257 | 773 | 384 | 40 |
| 120 K | N | 255 | 741 | 375 | 31 |
| 120 K | CA | 261 | 731 | 367 | 31 |
| 120 K | C | 252 | 719 | 365 | 31 |
| 120 K | O | 249 | 715 | 354 | 27 |
| 120 K | CB | 275 | 727 | 373 | 33 |
| 120 K | CG | 282 | 717 | 364 | 37 |
| 120 K | CD | 296 | 715 | 369 | 41 |
| 120 K | CE | 304 | 706 | 360 | 46 |
| 120 K | NZ | 318 | 704 | 365 | 49 |
| 121 A | N | 246 | 714 | 376 | 28 |
| 121 A | CA | 237 | 702 | 376 | 25 |
| 121 A | C | 224 | 706 | 369 | 26 |
| 121 A | O | 219 | 698 | 360 | 27 |

TABLE 1-continued

| | | | | | |
|---|---|---|---|---|---|
| 121 A | CB | 234 | 697 | 390 | 21 |
| 122 V | N | 218 | 717 | 373 | 25 |
| 122 V | CA | 205 | 721 | 367 | 27 |
| 122 V | C | 206 | 724 | 352 | 27 |
| 122 V | O | 197 | 721 | 344 | 27 |
| 122 V | CB | 199 | 734 | 375 | 27 |
| 122 V | CG1 | 189 | 741 | 367 | 28 |
| 122 V | CG2 | 193 | 729 | 388 | 26 |
| 123 N | N | 217 | 730 | 348 | 28 |
| 123 N | CA | 219 | 733 | 334 | 28 |
| 123 N | C | 221 | 720 | 326 | 25 |
| 123 N | O | 214 | 719 | 316 | 25 |
| 123 N | CB | 232 | 742 | 332 | 30 |
| 123 N | CG | 230 | 756 | 338 | 38 |
| 123 N | OD1 | 219 | 761 | 339 | 40 |
| 123 N | ND2 | 241 | 763 | 341 | 42 |
| 124 H | N | 228 | 711 | 331 | 25 |
| 124 H | CA | 229 | 698 | 325 | 25 |
| 124 H | C | 216 | 690 | 324 | 27 |
| 124 H | O | 214 | 682 | 314 | 24 |
| 124 H | CB | 240 | 690 | 331 | 21 |
| 124 H | CG | 242 | 676 | 325 | 24 |
| 124 H | ND1 | 239 | 664 | 331 | 23 |
| 124 H | CD2 | 246 | 672 | 313 | 23 |
| 124 H | CE1 | 241 | 654 | 323 | 23 |
| 124 H | NE2 | 246 | 659 | 312 | 26 |
| 125 I | N | 209 | 690 | 335 | 26 |
| 125 I | CA | 196 | 683 | 335 | 22 |
| 125 I | C | 187 | 689 | 324 | 21 |
| 125 I | O | 181 | 681 | 317 | 20 |
| 125 I | CB | 189 | 685 | 350 | 24 |
| 125 I | CG1 | 196 | 675 | 360 | 20 |
| 125 I | CG2 | 174 | 682 | 349 | 20 |
| 125 I | CD1 | 195 | 680 | 374 | 23 |
| 126 H | N | 187 | 702 | 323 | 22 |
| 126 H | CA | 179 | 709 | 313 | 26 |
| 126 H | C | 184 | 704 | 298 | 29 |
| 126 H | O | 175 | 703 | 289 | 28 |
| 126 H | CB | 180 | 724 | 314 | 28 |
| 126 H | CG | 170 | 730 | 324 | 36 |
| 126 H | ND1 | 173 | 741 | 331 | 39 |
| 126 H | CD2 | 158 | 726 | 327 | 39 |
| 126 H | CE1 | 163 | 744 | 339 | 40 |
| 126 H | NE2 | 153 | 734 | 337 | 40 |
| 127 S | N | 197 | 702 | 297 | 27 |
| 127 S | CA | 201 | 697 | 284 | 25 |
| 127 S | C | 197 | 683 | 281 | 23 |
| 127 S | O | 194 | 680 | 269 | 25 |
| 127 S | CB | 217 | 700 | 282 | 27 |
| 127 S | OG | 225 | 692 | 290 | 28 |
| 128 V | N | 197 | 675 | 291 | 20 |
| 128 V | CA | 192 | 661 | 289 | 18 |
| 128 V | C | 178 | 660 | 286 | 20 |
| 128 V | O | 174 | 652 | 277 | 19 |
| 128 V | CB | 194 | 652 | 302 | 16 |
| 128 V | CG1 | 191 | 638 | 300 | 9 |
| 128 V | CG2 | 209 | 654 | 307 | 19 |
| 129 W | N | 169 | 668 | 293 | 21 |
| 129 W | CA | 155 | 669 | 290 | 21 |
| 129 W | C | 152 | 673 | 276 | 21 |
| 129 W | O | 145 | 667 | 268 | 19 |
| 129 W | CB | 149 | 679 | 300 | 17 |
| 129 W | CG | 133 | 679 | 299 | 22 |
| 129 W | CD1 | 126 | 689 | 294 | 20 |
| 129 W | CD2 | 124 | 669 | 304 | 21 |
| 129 W | NE1 | 112 | 686 | 295 | 19 |
| 129 W | CE2 | 111 | 674 | 301 | 18 |
| 129 W | CE3 | 126 | 657 | 310 | 17 |
| 129 W | CZ2 | 100 | 667 | 305 | 20 |
| 129 W | CZ3 | 114 | 649 | 314 | 17 |
| 129 W | CH2 | 102 | 654 | 311 | 17 |
| 130 K | N | 159 | 684 | 272 | 23 |
| 130 K | CA | 158 | 690 | 258 | 24 |
| 130 K | C | 161 | 679 | 248 | 24 |
| 130 K | O | 154 | 677 | 238 | 23 |
| 130 K | CB | 167 | 702 | 256 | 27 |
| 130 K | CG | 166 | 709 | 243 | 34 |
| 130 K | CD | 175 | 721 | 242 | 40 |
| 130 K | CE | 170 | 733 | 251 | 49 |
| 130 K | NZ | 180 | 745 | 252 | 52 |
| 131 D | N | 172 | 672 | 251 | 23 |
| 131 D | CA | 177 | 661 | 242 | 22 |
| 131 D | C | 166 | 650 | 241 | 22 |
| 131 D | O | 165 | 644 | 231 | 20 |
| 131 D | CB | 190 | 656 | 246 | 23 |
| 131 D | CG | 196 | 645 | 237 | 21 |
| 131 D | OD1 | 199 | 648 | 225 | 25 |
| 131 D | OD2 | 196 | 633 | 240 | 21 |
| 132 L | N | 159 | 647 | 252 | 20 |
| 132 L | CA | 149 | 637 | 252 | 19 |
| 132 L | C | 137 | 641 | 243 | 19 |
| 132 L | O | 131 | 632 | 237 | 21 |
| 132 L | CB | 144 | 634 | 266 | 18 |
| 132 L | CG | 152 | 625 | 276 | 19 |
| 132 L | CD1 | 144 | 625 | 289 | 16 |
| 132 L | CD2 | 154 | 612 | 270 | 18 |
| 133 L | N | 134 | 653 | 243 | 20 |
| 133 L | CA | 123 | 658 | 234 | 20 |
| 133 L | C | 126 | 658 | 220 | 25 |
| 133 L | O | 118 | 656 | 211 | 26 |
| 133 L | CB | 118 | 672 | 239 | 16 |
| 133 L | CG | 113 | 674 | 253 | 17 |
| 133 L | CD1 | 108 | 688 | 254 | 18 |
| 133 L | CD2 | 102 | 664 | 257 | 13 |
| 134 E | N | 139 | 661 | 217 | 25 |
| 134 E | CA | 143 | 662 | 203 | 25 |
| 134 E | C | 149 | 650 | 196 | 25 |
| 134 E | O | 148 | 649 | 184 | 28 |
| 134 E | CB | 153 | 674 | 201 | 29 |
| 134 E | CG | 146 | 687 | 205 | 39 |
| 134 E | CD | 154 | 699 | 205 | 44 |
| 134 E | OE1 | 167 | 698 | 208 | 48 |
| 134 E | OE2 | 149 | 710 | 203 | 47 |
| 135 D | N | 152 | 639 | 204 | 26 |
| 135 D | CA | 157 | 627 | 199 | 22 |
| 135 D | C | 149 | 615 | 205 | 23 |
| 135 D | O | 149 | 614 | 217 | 23 |
| 135 D | CB | 172 | 626 | 203 | 24 |
| 135 D | CG | 180 | 614 | 197 | 23 |
| 135 D | OD1 | 173 | 603 | 194 | 21 |
| 135 D | OD2 | 192 | 615 | 195 | 26 |
| 136 T | N | 143 | 607 | 197 | 21 |
| 136 T | CA | 134 | 596 | 201 | 20 |
| 136 T | C | 141 | 583 | 197 | 17 |
| 136 T | O | 135 | 572 | 198 | 17 |
| 136 T | CB | 120 | 598 | 196 | 22 |
| 136 T | OG1 | 112 | 606 | 205 | 26 |
| 136 T | CG2 | 112 | 585 | 193 | 26 |
| 137 V | N | 153 | 583 | 192 | 19 |
| 137 V | CA | 159 | 571 | 187 | 19 |
| 137 V | C | 172 | 566 | 193 | 17 |
| 137 V | O | 173 | 554 | 195 | 20 |
| 137 V | CB | 160 | 571 | 171 | 20 |
| 137 V | CG1 | 147 | 574 | 164 | 22 |
| 137 V | CG2 | 170 | 581 | 167 | 21 |
| 138 T | N | 181 | 575 | 196 | 18 |
| 138 T | CA | 194 | 571 | 201 | 19 |
| 138 T | C | 195 | 563 | 214 | 20 |
| 138 T | O | 191 | 569 | 225 | 21 |
| 138 T | CB | 204 | 583 | 202 | 18 |
| 138 T | OG1 | 201 | 592 | 191 | 17 |
| 138 T | CG2 | 219 | 578 | 201 | 17 |
| 139 P | N | 200 | 551 | 215 | 22 |
| 139 P | CA | 201 | 543 | 227 | 22 |
| 139 P | C | 209 | 551 | 238 | 21 |
| 139 P | O | 219 | 557 | 234 | 22 |
| 139 P | CB | 208 | 530 | 223 | 22 |
| 139 P | CG | 203 | 528 | 209 | 23 |
| 139 P | CD | 204 | 543 | 203 | 21 |
| 140 I | N | 204 | 552 | 250 | 21 |
| 140 I | CA | 211 | 559 | 261 | 20 |
| 140 I | C | 221 | 549 | 268 | 17 |
| 140 I | O | 218 | 537 | 269 | 19 |
| 140 I | CB | 200 | 565 | 270 | 19 |
| 140 I | CG1 | 193 | 577 | 263 | 18 |
| 140 I | CG2 | 206 | 569 | 284 | 18 |
| 140 I | CD1 | 181 | 582 | 270 | 21 |
| 141 D | N | 232 | 555 | 272 | 19 |

TABLE 1-continued

| | | | | | |
|---|---|---|---|---|---|
| 141 D | CA | 242 | 547 | 279 | 19 |
| 141 D | C | 237 | 542 | 293 | 20 |
| 141 D | O | 230 | 549 | 300 | 21 |
| 141 D | CB | 255 | 555 | 281 | 22 |
| 141 D | CG | 267 | 547 | 286 | 27 |
| 141 D | OD1 | 268 | 535 | 282 | 23 |
| 141 D | OD2 | 275 | 552 | 294 | 36 |
| 142 T | N | 242 | 531 | 296 | 19 |
| 142 T | CA | 239 | 524 | 309 | 22 |
| 142 T | C | 251 | 518 | 315 | 25 |
| 142 T | O | 261 | 514 | 308 | 25 |
| 142 T | CB | 228 | 513 | 305 | 23 |
| 142 T | OG1 | 215 | 518 | 309 | 30 |
| 142 T | CG2 | 232 | 500 | 311 | 22 |
| 143 T | N | 251 | 518 | 329 | 24 |
| 143 T | CA | 263 | 511 | 336 | 22 |
| 143 T | C | 258 | 498 | 342 | 20 |
| 143 T | O | 247 | 497 | 347 | 22 |
| 143 T | CB | 267 | 520 | 348 | 20 |
| 143 T | OG1 | 272 | 533 | 343 | 19 |
| 143 T | CG2 | 278 | 513 | 356 | 20 |
| 144 I | N | 266 | 488 | 341 | 15 |
| 144 I | CA | 263 | 475 | 346 | 18 |
| 144 I | C | 272 | 472 | 358 | 23 |
| 144 I | O | 284 | 473 | 357 | 21 |
| 144 I | CB | 263 | 463 | 335 | 18 |
| 144 I | CG1 | 257 | 451 | 341 | 16 |
| 144 I | CG2 | 277 | 461 | 330 | 21 |
| 144 I | CD1 | 254 | 440 | 331 | 15 |
| 145 M | N | 266 | 468 | 369 | 22 |
| 145 M | CA | 274 | 465 | 381 | 24 |
| 145 M | C | 269 | 452 | 388 | 22 |
| 145 M | O | 257 | 448 | 385 | 20 |
| 145 M | CB | 271 | 476 | 392 | 26 |
| 145 M | CG | 276 | 490 | 389 | 33 |
| 145 M | SD | 297 | 491 | 389 | 45 |
| 145 M | CE | 299 | 510 | 397 | 45 |
| 146 A | N | 278 | 446 | 395 | 21 |
| 146 A | CA | 274 | 434 | 402 | 22 |
| 146 A | C | 271 | 439 | 416 | 25 |
| 146 A | O | 278 | 448 | 422 | 24 |
| 146 A | CB | 286 | 424 | 403 | 22 |
| 147 K | N | 259 | 435 | 422 | 27 |
| 147 K | CA | 255 | 440 | 435 | 27 |
| 147 K | C | 262 | 431 | 446 | 21 |
| 147 K | O | 263 | 419 | 444 | 21 |
| 147 K | CB | 240 | 439 | 437 | 30 |
| 147 K | CG | 232 | 448 | 428 | 34 |
| 147 K | CD | 217 | 445 | 431 | 43 |
| 147 K | CE | 208 | 452 | 420 | 45 |
| 147 K | NZ | 193 | 448 | 422 | 44 |
| 148 N | N | 266 | 438 | 457 | 25 |
| 148 N | CA | 272 | 431 | 468 | 26 |
| 148 N | C | 260 | 429 | 478 | 23 |
| 148 N | O | 257 | 439 | 485 | 26 |
| 148 N | CB | 282 | 439 | 475 | 29 |
| 148 N | CG | 293 | 443 | 466 | 30 |
| 148 N | OD1 | 296 | 455 | 465 | 33 |
| 148 N | ND2 | 300 | 434 | 459 | 28 |
| 149 E | N | 255 | 417 | 480 | 26 |
| 149 E | CA | 244 | 415 | 489 | 28 |
| 149 E | C | 247 | 403 | 498 | 26 |
| 149 E | O | 254 | 394 | 494 | 26 |
| 149 E | CB | 231 | 413 | 482 | 28 |
| 149 E | CG | 226 | 424 | 474 | 30 |
| 149 E | CD | 213 | 422 | 467 | 34 |
| 149 E | OE1 | 212 | 412 | 459 | 32 |
| 149 E | OE2 | 204 | 430 | 468 | 39 |
| 150 V | N | 243 | 404 | 511 | 24 |
| 150 V | CA | 246 | 394 | 521 | 21 |
| 150 V | C | 236 | 383 | 522 | 20 |
| 150 V | O | 224 | 386 | 522 | 23 |
| 150 V | CB | 249 | 400 | 535 | 20 |
| 150 V | CG1 | 251 | 390 | 546 | 21 |
| 150 V | CG2 | 260 | 411 | 535 | 16 |
| 151 F | N | 240 | 370 | 523 | 18 |
| 151 F | CA | 231 | 359 | 524 | 20 |
| 151 F | C | 237 | 349 | 533 | 24 |
| 151 F | O | 249 | 350 | 537 | 24 |
| 151 F | CB | 228 | 352 | 510 | 24 |
| 151 F | CG | 221 | 361 | 500 | 23 |
| 151 F | CD1 | 208 | 363 | 500 | 24 |
| 151 F | CD2 | 229 | 368 | 491 | 25 |
| 151 F | CE1 | 202 | 371 | 490 | 25 |
| 151 F | CE2 | 224 | 376 | 481 | 25 |
| 151 F | CZ | 210 | 378 | 481 | 23 |
| 152 C | N | 229 | 339 | 537 | 25 |
| 152 C | CA | 233 | 327 | 544 | 28 |
| 152 C | C | 235 | 316 | 534 | 31 |
| 152 C | O | 226 | 315 | 525 | 33 |
| 152 C | CB | 223 | 324 | 555 | 26 |
| 152 C | SG | 227 | 308 | 564 | 28 |
| 153 V | N | 245 | 308 | 535 | 33 |
| 153 V | CA | 248 | 297 | 526 | 39 |
| 153 V | C | 236 | 287 | 525 | 43 |
| 153 V | O | 229 | 284 | 535 | 45 |
| 153 V | CB | 261 | 290 | 529 | 40 |
| 153 V | CG1 | 263 | 279 | 519 | 45 |
| 153 V | CG2 | 272 | 300 | 529 | 39 |
| 154 Q | N | 234 | 282 | 513 | 49 |
| 154 Q | CA | 224 | 272 | 509 | 51 |
| 154 Q | C | 210 | 277 | 511 | 53 |
| 154 Q | O | 205 | 284 | 501 | 57 |
| 154 Q | CB | 225 | 259 | 518 | 54 |
| 154 Q | CG | 239 | 252 | 516 | 60 |
| 154 Q | CD | 241 | 241 | 526 | 63 |
| 154 Q | OE1 | 241 | 243 | 538 | 63 |
| 154 Q | NE2 | 241 | 228 | 521 | 66 |
| 160 R | N | 262 | 288 | 470 | 41 |
| 160 R | CA | 261 | 302 | 472 | 40 |
| 160 R | C | 255 | 309 | 459 | 40 |
| 160 R | O | 258 | 304 | 448 | 41 |
| 160 R | CB | 274 | 308 | 476 | 39 |
| 160 R | CG | 281 | 300 | 486 | 42 |
| 160 R | CD | 291 | 308 | 495 | 48 |
| 160 R | NE | 298 | 318 | 487 | 49 |
| 160 R | CZ | 309 | 325 | 491 | 51 |
| 160 R | NH1 | 314 | 323 | 503 | 52 |
| 160 R | NH2 | 314 | 334 | 483 | 55 |
| 161 K | N | 247 | 319 | 460 | 37 |
| 161 K | CA | 241 | 327 | 449 | 37 |
| 161 K | C | 251 | 336 | 442 | 34 |
| 161 K | O | 259 | 343 | 448 | 35 |
| 161 K | CB | 230 | 336 | 454 | 36 |
| 161 K | CG | 217 | 329 | 460 | 39 |
| 161 K | CD | 208 | 340 | 465 | 41 |
| 161 K | CE | 194 | 334 | 468 | 44 |
| 161 K | NZ | 193 | 324 | 479 | 47 |
| 162 P | N | 249 | 337 | 428 | 33 |
| 162 P | CA | 258 | 346 | 421 | 29 |
| 162 P | C | 253 | 360 | 423 | 28 |
| 162 P | O | 241 | 362 | 426 | 27 |
| 162 P | CB | 256 | 342 | 406 | 29 |
| 162 P | CG | 250 | 328 | 407 | 29 |
| 162 P | CD | 241 | 329 | 419 | 31 |
| 163 A | N | 261 | 370 | 422 | 23 |
| 163 A | CA | 257 | 384 | 424 | 21 |
| 163 A | C | 245 | 387 | 415 | 25 |
| 163 A | O | 244 | 381 | 404 | 24 |
| 163 A | CB | 269 | 393 | 421 | 18 |
| 164 R | N | 236 | 397 | 419 | 24 |
| 164 R | CA | 226 | 401 | 410 | 26 |
| 164 R | C | 231 | 413 | 403 | 27 |
| 164 R | O | 240 | 420 | 408 | 27 |
| 164 R | CB | 213 | 405 | 418 | 30 |
| 164 R | CG | 205 | 393 | 423 | 38 |
| 164 R | CD | 191 | 397 | 426 | 44 |
| 164 R | NE | 191 | 408 | 436 | 52 |
| 164 R | CZ | 184 | 420 | 434 | 58 |
| 164 R | NH1 | 176 | 422 | 424 | 65 |
| 164 R | NH2 | 184 | 429 | 444 | 59 |
| 165 L | N | 226 | 416 | 391 | 26 |
| 165 L | CA | 231 | 427 | 383 | 27 |
| 165 L | C | 222 | 439 | 383 | 25 |
| 165 L | O | 210 | 438 | 383 | 29 |
| 165 L | CB | 234 | 422 | 369 | 30 |
| 165 L | CG | 247 | 415 | 365 | 30 |
| 165 L | CD1 | 254 | 408 | 376 | 25 |

TABLE 1-continued

| | | | | | |
|---|---|---|---|---|---|
| 165 | L | CD2 | 244 | 405 | 353 | 29 |
| 166 | I | N | 228 | 451 | 384 | 20 |
| 166 | I | CA | 221 | 464 | 384 | 22 |
| 166 | I | C | 225 | 471 | 371 | 23 |
| 166 | I | O | 237 | 472 | 368 | 21 |
| 166 | I | CB | 223 | 472 | 397 | 23 |
| 166 | I | CG1 | 216 | 486 | 396 | 25 |
| 166 | I | CG2 | 238 | 475 | 398 | 25 |
| 166 | I | CD1 | 201 | 485 | 401 | 25 |
| 167 | V | N | 215 | 476 | 364 | 20 |
| 167 | V | CA | 217 | 484 | 352 | 17 |
| 167 | V | C | 211 | 497 | 354 | 16 |
| 167 | V | O | 199 | 498 | 356 | 17 |
| 167 | V | CB | 211 | 476 | 340 | 14 |
| 167 | V | CG1 | 211 | 485 | 327 | 15 |
| 167 | V | CG2 | 218 | 463 | 338 | 15 |
| 168 | F | N | 218 | 508 | 353 | 12 |
| 168 | F | CA | 213 | 521 | 355 | 16 |
| 168 | F | C | 218 | 533 | 346 | 19 |
| 168 | F | O | 230 | 532 | 342 | 21 |
| 168 | F | CB | 214 | 526 | 370 | 15 |
| 168 | F | CG | 229 | 526 | 375 | 16 |
| 168 | F | CD1 | 236 | 514 | 378 | 15 |
| 168 | F | CD2 | 236 | 538 | 376 | 16 |
| 168 | F | CE1 | 249 | 514 | 382 | 14 |
| 168 | F | CE2 | 249 | 538 | 380 | 15 |
| 168 | F | CZ | 256 | 526 | 383 | 9 |
| 169 | P | N | 210 | 543 | 343 | 19 |
| 169 | P | CA | 214 | 554 | 334 | 19 |
| 169 | P | C | 221 | 564 | 343 | 22 |
| 169 | P | O | 221 | 564 | 355 | 25 |
| 169 | P | CB | 201 | 559 | 329 | 16 |
| 169 | P | CG | 192 | 556 | 340 | 17 |
| 169 | P | CD | 195 | 542 | 344 | 18 |
| 170 | D | N | 227 | 574 | 337 | 19 |
| 170 | D | CA | 234 | 585 | 344 | 21 |
| 170 | D | C | 225 | 593 | 352 | 24 |
| 170 | D | O | 213 | 594 | 350 | 27 |
| 170 | D | CB | 241 | 594 | 334 | 21 |
| 170 | D | CG | 250 | 604 | 340 | 19 |
| 170 | D | OD1 | 261 | 599 | 345 | 22 |
| 170 | D | OD2 | 247 | 616 | 341 | 17 |
| 171 | L | N | 230 | 600 | 362 | 22 |
| 171 | L | CA | 223 | 609 | 371 | 23 |
| 171 | L | C | 214 | 618 | 364 | 23 |
| 171 | L | O | 202 | 619 | 368 | 21 |
| 171 | L | CB | 233 | 616 | 381 | 19 |
| 171 | L | CG | 228 | 626 | 391 | 23 |
| 171 | L | CD1 | 217 | 620 | 399 | 23 |
| 171 | L | CD2 | 240 | 631 | 399 | 21 |
| 172 | G | N | 219 | 626 | 354 | 23 |
| 172 | G | CA | 210 | 635 | 347 | 23 |
| 172 | G | C | 198 | 629 | 341 | 20 |
| 172 | G | O | 187 | 636 | 340 | 20 |
| 173 | V | N | 199 | 617 | 336 | 19 |
| 173 | V | CA | 188 | 609 | 330 | 19 |
| 173 | V | C | 178 | 605 | 341 | 20 |
| 173 | V | O | 166 | 605 | 339 | 16 |
| 173 | V | CB | 194 | 597 | 323 | 17 |
| 173 | V | CG1 | 182 | 587 | 318 | 12 |
| 173 | V | CG2 | 202 | 601 | 310 | 14 |
| 174 | R | N | 184 | 601 | 352 | 18 |
| 174 | R | CA | 176 | 597 | 364 | 18 |
| 174 | R | C | 167 | 608 | 369 | 18 |
| 174 | R | O | 155 | 605 | 372 | 19 |
| 174 | R | CB | 184 | 592 | 375 | 18 |
| 174 | R | CG | 190 | 578 | 373 | 21 |
| 174 | R | CD | 194 | 572 | 386 | 23 |
| 174 | R | NE | 208 | 569 | 386 | 33 |
| 174 | R | CZ | 217 | 577 | 392 | 29 |
| 174 | R | NH1 | 213 | 588 | 399 | 39 |
| 174 | R | NH2 | 230 | 575 | 391 | 36 |
| 175 | V | N | 172 | 620 | 369 | 16 |
| 175 | V | CA | 164 | 632 | 374 | 17 |
| 175 | V | C | 153 | 634 | 363 | 21 |
| 175 | V | O | 141 | 638 | 367 | 18 |
| 175 | V | CB | 172 | 644 | 375 | 15 |
| 175 | V | CG1 | 164 | 656 | 379 | 15 |
| 175 | V | CG2 | 182 | 642 | 387 | 16 |
| 176 | C | N | 156 | 632 | 351 | 20 |
| 176 | C | CA | 146 | 634 | 340 | 20 |
| 176 | C | C | 135 | 623 | 340 | 17 |
| 176 | C | O | 123 | 627 | 337 | 16 |
| 176 | C | CB | 153 | 634 | 326 | 16 |
| 176 | C | SG | 162 | 649 | 322 | 18 |
| 177 | E | N | 138 | 611 | 344 | 17 |
| 177 | E | CA | 128 | 600 | 345 | 18 |
| 177 | E | C | 118 | 605 | 356 | 19 |
| 177 | E | O | 106 | 603 | 354 | 16 |
| 177 | E | CB | 134 | 587 | 350 | 14 |
| 177 | E | CG | 142 | 580 | 340 | 20 |
| 177 | E | CD | 146 | 566 | 345 | 22 |
| 177 | E | OE1 | 138 | 557 | 345 | 20 |
| 177 | E | OE2 | 157 | 565 | 350 | 28 |
| 178 | K | N | 123 | 611 | 367 | 20 |
| 178 | K | CA | 114 | 616 | 378 | 20 |
| 178 | K | C | 104 | 626 | 373 | 21 |
| 178 | K | O | 92 | 625 | 375 | 22 |
| 178 | K | CB | 123 | 622 | 389 | 18 |
| 178 | K | CG | 131 | 612 | 397 | 20 |
| 178 | K | CD | 140 | 619 | 407 | 20 |
| 178 | K | CE | 147 | 610 | 417 | 16 |
| 178 | K | NZ | 155 | 600 | 410 | 21 |
| 179 | M | N | 109 | 637 | 367 | 21 |
| 179 | M | CA | 101 | 647 | 361 | 25 |
| 179 | M | C | 90 | 642 | 352 | 24 |
| 179 | M | O | 78 | 646 | 353 | 23 |
| 179 | M | CB | 109 | 657 | 353 | 27 |
| 179 | M | CG | 118 | 665 | 362 | 33 |
| 179 | M | SD | 131 | 677 | 351 | 38 |
| 179 | M | CE | 147 | 664 | 351 | 35 |
| 180 | A | N | 93 | 633 | 343 | 21 |
| 180 | A | CA | 84 | 627 | 333 | 22 |
| 180 | A | C | 74 | 616 | 339 | 23 |
| 180 | A | O | 63 | 616 | 335 | 25 |
| 180 | A | CB | 91 | 621 | 321 | 18 |
| 181 | L | N | 79 | 607 | 348 | 21 |
| 181 | L | CA | 71 | 596 | 352 | 18 |
| 181 | L | C | 68 | 594 | 367 | 17 |
| 181 | L | O | 61 | 585 | 371 | 20 |
| 181 | L | CB | 77 | 583 | 346 | 18 |
| 181 | L | CG | 74 | 581 | 331 | 20 |
| 181 | L | CD1 | 86 | 574 | 325 | 14 |
| 181 | L | CD2 | 61 | 573 | 329 | 16 |
| 182 | Y | N | 74 | 602 | 376 | 19 |
| 182 | Y | CA | 71 | 600 | 390 | 20 |
| 182 | Y | C | 57 | 600 | 394 | 22 |
| 182 | Y | O | 52 | 590 | 401 | 20 |
| 182 | Y | CB | 79 | 611 | 399 | 22 |
| 182 | Y | CG | 78 | 608 | 414 | 21 |
| 182 | Y | CD1 | 86 | 598 | 419 | 20 |
| 182 | Y | CD2 | 70 | 615 | 422 | 20 |
| 182 | Y | CE1 | 85 | 594 | 433 | 22 |
| 182 | Y | CE2 | 69 | 612 | 436 | 23 |
| 182 | Y | CZ | 76 | 602 | 441 | 23 |
| 182 | Y | OH | 76 | 599 | 454 | 25 |
| 183 | D | N | 49 | 609 | 390 | 23 |
| 183 | D | CA | 35 | 610 | 393 | 23 |
| 183 | D | C | 27 | 598 | 387 | 22 |
| 183 | D | O | 19 | 592 | 394 | 16 |
| 183 | D | CB | 29 | 623 | 388 | 26 |
| 183 | D | CG | 16 | 626 | 396 | 25 |
| 183 | D | OD1 | 14 | 621 | 407 | 27 |
| 183 | D | OD2 | 8 | 635 | 390 | 27 |
| 184 | V | N | 31 | 594 | 375 | 22 |
| 184 | V | CA | 25 | 582 | 369 | 20 |
| 184 | V | C | 28 | 569 | 376 | 19 |
| 184 | V | O | 19 | 562 | 379 | 16 |
| 184 | V | CB | 29 | 581 | 354 | 16 |
| 184 | V | CG1 | 26 | 567 | 349 | 15 |
| 184 | V | CG2 | 21 | 591 | 346 | 19 |
| 185 | V | N | 41 | 566 | 379 | 16 |
| 185 | V | CA | 44 | 554 | 386 | 15 |
| 185 | V | C | 39 | 553 | 400 | 16 |
| 185 | V | O | 37 | 543 | 406 | 19 |
| 185 | V | CB | 60 | 551 | 386 | 15 |
| 185 | V | CG1 | 66 | 551 | 371 | 12 |
| 185 | V | CG2 | 67 | 561 | 394 | 17 |

TABLE 1-continued

| | | | | | |
|---|---|---|---|---|---|
| 186 S | N | 36 | 565 | 406 | 18 |
| 186 S | CA | 30 | 566 | 419 | 19 |
| 186 S | C | 15 | 564 | 419 | 23 |
| 186 S | O | 9 | 558 | 429 | 25 |
| 186 S | CB | 33 | 579 | 425 | 16 |
| 186 S | OG | 47 | 582 | 426 | 18 |
| 187 T | N | 8 | 569 | 409 | 23 |
| 187 T | CA | −5 | 569 | 408 | 23 |
| 187 T | C | −13 | 558 | 400 | 23 |
| 187 T | O | −22 | 552 | 404 | 21 |
| 187 T | CB | −10 | 583 | 404 | 25 |
| 187 T | OG1 | −4 | 593 | 412 | 28 |
| 187 T | CG2 | −26 | 584 | 406 | 32 |
| 188 L | N | −7 | 556 | 388 | 22 |
| 188 L | CA | −13 | 547 | 379 | 21 |
| 188 L | C | −15 | 532 | 383 | 20 |
| 188 L | O | −26 | 526 | 380 | 20 |
| 188 L | CB | −6 | 547 | 365 | 24 |
| 188 L | CG | −10 | 539 | 352 | 23 |
| 188 L | CD1 | −4 | 545 | 340 | 25 |
| 188 L | CD2 | −6 | 525 | 353 | 27 |
| 189 P | N | −6 | 526 | 390 | 20 |
| 189 P | CA | −8 | 512 | 394 | 18 |
| 189 P | C | −20 | 509 | 403 | 18 |
| 189 P | O | −27 | 499 | 401 | 19 |
| 189 P | CB | 4 | 509 | 402 | 19 |
| 189 P | CG | 14 | 519 | 397 | 18 |
| 189 P | CD | 6 | 531 | 396 | 17 |
| 190 Q | N | −23 | 518 | 413 | 19 |
| 190 Q | CA | −35 | 515 | 421 | 21 |
| 190 Q | C | −48 | 517 | 413 | 21 |
| 190 Q | O | −58 | 510 | 415 | 20 |
| 190 Q | CB | −35 | 523 | 434 | 22 |
| 190 Q | CG | −46 | 520 | 444 | 30 |
| 190 Q | CD | −59 | 526 | 441 | 31 |
| 190 Q | OE1 | −60 | 538 | 437 | 30 |
| 190 Q | NE2 | −70 | 518 | 443 | 31 |
| 191 V | N | −48 | 527 | 404 | 19 |
| 191 V | CA | −60 | 530 | 396 | 21 |
| 191 V | C | −63 | 518 | 387 | 24 |
| 191 V | O | −75 | 514 | 386 | 25 |
| 191 V | CB | −58 | 543 | 388 | 16 |
| 191 V | CG1 | −70 | 545 | 378 | 17 |
| 191 V | CG2 | −58 | 555 | 398 | 16 |
| 192 V | N | −53 | 512 | 381 | 20 |
| 192 V | CA | −54 | 501 | 371 | 19 |
| 192 V | C | −58 | 488 | 377 | 24 |
| 192 V | O | −65 | 480 | 372 | 19 |
| 192 V | CB | −41 | 500 | 362 | 19 |
| 192 V | CG1 | −42 | 487 | 354 | 17 |
| 192 V | CG2 | −40 | 512 | 353 | 19 |
| 193 M | N | −52 | 485 | 389 | 25 |
| 193 M | CA | −53 | 472 | 395 | 25 |
| 193 M | C | −62 | 471 | 408 | 22 |
| 193 M | O | −64 | 461 | 414 | 21 |
| 193 M | CB | −39 | 466 | 398 | 26 |
| 193 M | CG | −29 | 470 | 387 | 32 |
| 193 M | SD | −11 | 462 | 389 | 33 |
| 193 M | CE | −17 | 449 | 404 | 19 |
| 194 G | N | −66 | 483 | 413 | 21 |
| 194 G | CA | −73 | 484 | 425 | 23 |
| 194 G | C | −66 | 478 | 437 | 27 |
| 194 G | O | −54 | 480 | 439 | 28 |
| 195 S | N | −74 | 470 | 445 | 25 |
| 195 S | CA | −69 | 463 | 457 | 23 |
| 195 S | C | −58 | 453 | 454 | 21 |
| 195 S | O | −51 | 448 | 464 | 23 |
| 195 S | CB | −80 | 456 | 464 | 24 |
| 195 S | OG | −87 | 447 | 456 | 29 |
| 196 S | N | −55 | 449 | 442 | 21 |
| 196 S | CA | −45 | 439 | 438 | 22 |
| 196 S | C | −31 | 445 | 438 | 20 |
| 196 S | O | −21 | 438 | 438 | 21 |
| 196 S | CB | −48 | 434 | 424 | 19 |
| 196 S | OG | −59 | 425 | 425 | 26 |
| 197 Y | N | −30 | 459 | 439 | 19 |
| 197 Y | CA | −17 | 465 | 439 | 19 |
| 197 Y | C | −11 | 464 | 453 | 19 |
| 197 Y | O | −15 | 471 | 462 | 21 |
| 197 Y | CB | −18 | 480 | 435 | 14 |
| 197 Y | CG | −4 | 486 | 434 | 13 |
| 197 Y | CD1 | 5 | 480 | 427 | 15 |
| 197 Y | CD2 | −2 | 499 | 440 | 14 |
| 197 Y | CE1 | 18 | 487 | 426 | 14 |
| 197 Y | CE2 | 9 | 505 | 439 | 18 |
| 197 Y | CZ | 19 | 499 | 431 | 15 |
| 197 Y | OH | 31 | 506 | 430 | 16 |
| 198 G | N | −1 | 456 | 455 | 21 |
| 198 G | CA | 4 | 454 | 468 | 21 |
| 198 G | C | 11 | 465 | 475 | 19 |
| 198 G | O | 10 | 467 | 487 | 20 |
| 199 F | N | 18 | 474 | 468 | 19 |
| 199 F | CA | 25 | 485 | 474 | 18 |
| 199 F | C | 16 | 496 | 481 | 21 |
| 199 F | O | 21 | 506 | 486 | 19 |
| 199 F | CB | 35 | 492 | 464 | 19 |
| 199 F | CG | 46 | 482 | 460 | 16 |
| 199 F | CD1 | 55 | 477 | 469 | 19 |
| 199 F | CD2 | 47 | 478 | 446 | 18 |
| 199 F | CE1 | 66 | 469 | 465 | 17 |
| 199 F | CE2 | 58 | 470 | 442 | 16 |
| 199 F | CZ | 67 | 465 | 451 | 17 |
| 200 Q | N | 3 | 495 | 480 | 20 |
| 200 Q | CA | −5 | 505 | 486 | 20 |
| 200 Q | C | −7 | 502 | 501 | 20 |
| 200 Q | O | −12 | 510 | 509 | 21 |
| 200 Q | CB | −18 | 507 | 479 | 20 |
| 200 Q | CG | −28 | 495 | 481 | 21 |
| 200 Q | CD | −40 | 495 | 473 | 20 |
| 200 Q | OE1 | −49 | 504 | 474 | 18 |
| 200 Q | NE2 | −42 | 486 | 464 | 17 |
| 201 Y | N | −3 | 490 | 505 | 21 |
| 201 Y | CA | −5 | 485 | 518 | 19 |
| 201 Y | C | 6 | 485 | 527 | 23 |
| 201 Y | O | 17 | 482 | 523 | 22 |
| 201 Y | CB | −10 | 470 | 518 | 17 |
| 201 Y | CG | −22 | 467 | 509 | 16 |
| 201 Y | CD1 | −34 | 475 | 511 | 18 |
| 201 Y | CD2 | −22 | 457 | 500 | 18 |
| 201 Y | CE1 | −45 | 472 | 504 | 21 |
| 201 Y | CE2 | −34 | 454 | 492 | 22 |
| 201 Y | CZ | −45 | 462 | 494 | 24 |
| 201 Y | OH | −57 | 459 | 487 | 21 |
| 202 S | N | 4 | 487 | 540 | 25 |
| 202 S | CA | 14 | 487 | 550 | 21 |
| 202 S | C | 14 | 472 | 554 | 18 |
| 202 S | O | 4 | 465 | 550 | 20 |
| 202 S | CB | 10 | 495 | 563 | 23 |
| 202 S | OG | 0 | 489 | 570 | 23 |
| 203 P | N | 24 | 466 | 560 | 20 |
| 203 P | CA | 23 | 452 | 563 | 20 |
| 203 P | C | 10 | 447 | 570 | 19 |
| 203 P | O | 5 | 436 | 567 | 21 |
| 203 P | CB | 36 | 450 | 572 | 19 |
| 203 P | CG | 45 | 460 | 567 | 17 |
| 203 P | CD | 36 | 472 | 566 | 18 |
| 204 G | N | 4 | 455 | 579 | 22 |
| 204 G | CA | −7 | 452 | 586 | 21 |
| 204 G | C | −19 | 452 | 576 | 23 |
| 204 G | O | −27 | 443 | 577 | 25 |
| 205 Q | N | −19 | 462 | 567 | 23 |
| 205 Q | CA | −30 | 463 | 557 | 22 |
| 205 Q | C | −29 | 452 | 547 | 24 |
| 205 Q | O | −39 | 448 | 541 | 27 |
| 205 Q | CB | −29 | 476 | 551 | 20 |
| 205 Q | CG | −33 | 488 | 560 | 22 |
| 205 Q | CD | −30 | 501 | 554 | 24 |
| 205 Q | OE1 | −20 | 503 | 547 | 27 |
| 205 Q | NE2 | −38 | 511 | 557 | 23 |
| 206 R | N | −17 | 447 | 545 | 24 |
| 206 R | CA | −15 | 436 | 535 | 21 |
| 206 R | C | −20 | 423 | 541 | 21 |
| 206 R | O | −26 | 415 | 534 | 19 |
| 206 R | CB | 0 | 434 | 532 | 21 |
| 206 R | CG | 3 | 422 | 525 | 20 |
| 206 R | CD | 18 | 420 | 523 | 25 |
| 206 R | NE | 21 | 417 | 510 | 34 |
| 206 R | CZ | 21 | 405 | 505 | 32 |

TABLE 1-continued

| | | | | | |
|---|---|---|---|---|---|
| 206 R | NH1 | 19 | 394 | 513 | 41 |
| 206 R | NH2 | 22 | 403 | 492 | 31 |
| 207 V | N | −18 | 421 | 554 | 23 |
| 207 V | CA | −23 | 409 | 561 | 23 |
| 207 V | C | −38 | 410 | 562 | 20 |
| 207 V | O | −45 | 400 | 560 | 20 |
| 207 V | CB | −17 | 409 | 576 | 24 |
| 207 V | CG1 | −23 | 397 | 583 | 24 |
| 207 V | CG2 | −2 | 408 | 576 | 22 |
| 208 E | N | −43 | 421 | 564 | 19 |
| 208 E | CA | −58 | 423 | 565 | 23 |
| 208 E | C | −64 | 420 | 552 | 27 |
| 208 E | O | −74 | 413 | 551 | 28 |
| 208 E | CB | −60 | 438 | 569 | 23 |
| 208 E | CG | −75 | 442 | 569 | 30 |
| 208 E | CD | −77 | 456 | 574 | 37 |
| 208 E | OE1 | −72 | 465 | 568 | 40 |
| 208 E | OE2 | −84 | 457 | 585 | 43 |
| 209 F | N | −58 | 425 | 541 | 26 |
| 209 F | CA | −63 | 422 | 528 | 24 |
| 209 F | C | −63 | 407 | 524 | 24 |
| 209 F | O | −73 | 401 | 519 | 25 |
| 209 F | CB | −55 | 430 | 517 | 28 |
| 209 F | CG | −59 | 427 | 503 | 32 |
| 209 F | CD1 | −71 | 432 | 498 | 31 |
| 209 F | CD2 | −52 | 418 | 495 | 30 |
| 209 F | CE1 | −76 | 428 | 485 | 34 |
| 209 F | CE2 | −56 | 414 | 482 | 31 |
| 209 F | CZ | −68 | 419 | 477 | 33 |
| 210 L | N | −52 | 400 | 527 | 22 |
| 210 L | CA | −51 | 386 | 524 | 21 |
| 210 L | C | −61 | 377 | 532 | 25 |
| 210 L | O | −67 | 368 | 527 | 25 |
| 210 L | CB | −37 | 381 | 527 | 22 |
| 210 L | CG | −26 | 384 | 517 | 21 |
| 210 L | CD1 | −12 | 383 | 524 | 20 |
| 210 L | CD2 | −27 | 376 | 505 | 18 |
| 211 V | N | −62 | 381 | 545 | 27 |
| 211 V | CA | −72 | 374 | 554 | 26 |
| 211 V | C | −86 | 376 | 550 | 23 |
| 211 V | O | −94 | 366 | 548 | 21 |
| 211 V | CB | −70 | 379 | 569 | 28 |
| 211 V | CG1 | −82 | 375 | 578 | 25 |
| 211 V | CG2 | −57 | 375 | 575 | 28 |
| 212 N | N | −90 | 388 | 547 | 24 |
| 212 N | CA | −104 | 391 | 542 | 27 |
| 212 N | C | −107 | 384 | 529 | 30 |
| 212 N | O | −117 | 378 | 527 | 34 |
| 212 N | CB | −106 | 406 | 541 | 23 |
| 212 N | CG | −108 | 412 | 555 | 26 |
| 212 N | OD1 | −112 | 405 | 565 | 29 |
| 212 N | ND2 | −106 | 425 | 556 | 24 |
| 213 T | N | −97 | 384 | 520 | 25 |
| 213 T | CA | −99 | 377 | 507 | 24 |
| 213 T | C | −100 | 362 | 509 | 23 |
| 213 T | O | −109 | 356 | 503 | 28 |
| 213 T | CB | −86 | 379 | 497 | 22 |
| 213 T | OG1 | −85 | 393 | 495 | 19 |
| 213 T | CG2 | −88 | 372 | 485 | 22 |
| 214 W | N | −92 | 357 | 518 | 22 |
| 214 W | CA | −93 | 342 | 521 | 25 |
| 214 W | C | −106 | 339 | 526 | 30 |
| 214 W | O | −112 | 328 | 523 | 31 |
| 214 W | CB | −82 | 339 | 531 | 21 |
| 214 W | CG | −80 | 324 | 533 | 22 |
| 214 W | CD1 | −85 | 316 | 542 | 23 |
| 214 W | CD2 | −71 | 316 | 524 | 24 |
| 214 W | NE1 | −80 | 303 | 541 | 23 |
| 214 W | CE2 | −72 | 303 | 530 | 24 |
| 214 W | CE3 | −64 | 318 | 513 | 20 |
| 214 W | CZ2 | −65 | 292 | 524 | 23 |
| 214 W | CZ3 | −57 | 307 | 508 | 15 |
| 214 W | CH2 | −57 | 294 | 513 | 20 |
| 215 K | N | −112 | 348 | 534 | 32 |
| 215 K | CA | −125 | 346 | 541 | 36 |
| 215 K | C | −137 | 348 | 531 | 37 |
| 215 K | O | −147 | 342 | 533 | 38 |
| 215 K | CB | −127 | 356 | 552 | 33 |
| 215 K | CG | −121 | 353 | 565 | 35 |
| 215 K | CD | −125 | 364 | 575 | 39 |
| 215 K | CE | −120 | 361 | 589 | 41 |
| 215 K | NZ | −123 | 372 | 598 | 44 |
| 216 S | N | −134 | 355 | 520 | 37 |
| 216 S | CA | −145 | 357 | 510 | 36 |
| 216 S | C | −147 | 345 | 501 | 33 |
| 216 S | O | −157 | 345 | 494 | 36 |
| 216 S | CB | −142 | 370 | 502 | 34 |
| 216 S | OG | −131 | 368 | 493 | 34 |
| 217 K | N | −139 | 335 | 502 | 31 |
| 217 K | CA | −141 | 323 | 493 | 34 |
| 217 K | C | −148 | 312 | 502 | 39 |
| 217 K | O | −144 | 310 | 513 | 39 |
| 217 K | CB | −127 | 318 | 488 | 31 |
| 217 K | CG | −117 | 328 | 483 | 29 |
| 217 K | CD | −123 | 336 | 471 | 24 |
| 217 K | CE | −113 | 347 | 467 | 20 |
| 217 K | NZ | −119 | 358 | 459 | 20 |
| 218 K | N | −158 | 306 | 496 | 40 |
| 218 K | CA | −165 | 295 | 502 | 42 |
| 218 K | C | −156 | 284 | 506 | 43 |
| 218 K | O | −158 | 277 | 517 | 45 |
| 218 K | CB | −176 | 289 | 493 | 46 |
| 218 K | CG | −184 | 300 | 486 | 53 |
| 218 K | CD | −196 | 293 | 478 | 55 |
| 218 K | CE | −202 | 302 | 467 | 57 |
| 218 K | NZ | −194 | 302 | 454 | 57 |
| 219 N | N | −146 | 282 | 498 | 43 |
| 219 N | CA | −136 | 271 | 500 | 44 |
| 219 N | C | −123 | 277 | 493 | 42 |
| 219 N | O | −120 | 273 | 482 | 43 |
| 219 N | CB | −141 | 258 | 494 | 48 |
| 219 N | CG | −131 | 247 | 496 | 57 |
| 219 N | OD1 | −125 | 245 | 507 | 62 |
| 219 N | ND2 | −128 | 239 | 486 | 63 |
| 220 P | N | −116 | 286 | 500 | 39 |
| 220 P | CA | −103 | 292 | 495 | 36 |
| 220 P | C | −92 | 282 | 492 | 31 |
| 220 P | O | −90 | 271 | 498 | 32 |
| 220 P | CB | −100 | 302 | 505 | 35 |
| 220 P | CG | −104 | 296 | 518 | 37 |
| 220 P | CD | −117 | 290 | 514 | 37 |
| 221 M | N | −84 | 286 | 482 | 28 |
| 221 M | CA | −72 | 279 | 478 | 26 |
| 221 M | C | −63 | 291 | 473 | 25 |
| 221 M | O | −68 | 300 | 468 | 22 |
| 221 M | CB | −75 | 269 | 467 | 28 |
| 221 M | CG | −62 | 262 | 461 | 32 |
| 221 M | SD | −52 | 273 | 448 | 35 |
| 221 M | CE | −56 | 263 | 430 | 39 |
| 222 G | N | −50 | 290 | 477 | 22 |
| 222 G | CA | −41 | 301 | 473 | 22 |
| 222 G | C | −28 | 295 | 468 | 20 |
| 222 G | O | −25 | 283 | 471 | 21 |
| 223 F | N | −20 | 303 | 460 | 22 |
| 223 F | CA | −7 | 299 | 456 | 21 |
| 223 F | C | 0 | 311 | 452 | 22 |
| 223 F | O | −4 | 322 | 450 | 23 |
| 223 F | CB | −8 | 289 | 443 | 22 |
| 223 F | CG | −13 | 296 | 431 | 24 |
| 223 F | CD1 | −5 | 301 | 422 | 22 |
| 223 F | CD2 | −27 | 296 | 428 | 25 |
| 223 F | CE1 | −9 | 307 | 410 | 26 |
| 223 F | CE2 | −32 | 302 | 416 | 27 |
| 223 F | CZ | −23 | 308 | 407 | 23 |
| 224 S | N | 13 | 309 | 453 | 22 |
| 224 S | CA | 22 | 320 | 450 | 22 |
| 224 S | C | 29 | 316 | 437 | 19 |
| 224 S | O | 29 | 304 | 434 | 19 |
| 224 S | CB | 33 | 322 | 461 | 18 |
| 224 S | OG | 40 | 310 | 464 | 19 |
| 225 Y | N | 32 | 325 | 429 | 20 |
| 225 Y | CA | 38 | 322 | 416 | 25 |
| 225 Y | C | 52 | 329 | 416 | 23 |
| 225 Y | O | 53 | 341 | 419 | 24 |
| 225 Y | CB | 30 | 326 | 404 | 25 |
| 225 Y | CG | 35 | 320 | 390 | 25 |
| 225 Y | CD1 | 33 | 307 | 387 | 22 |
| 225 Y | CD2 | 43 | 328 | 382 | 26 |

TABLE 1-continued

| | | | | | |
|---|---|---|---|---|---|
| 225 | Y | CE1 | 38 | 301 | 375 | 23 |
| 225 | Y | CE2 | 48 | 323 | 370 | 20 |
| 225 | Y | CZ | 46 | 309 | 367 | 20 |
| 225 | Y | OH | 51 | 304 | 355 | 19 |
| 226 | D | N | 62 | 321 | 412 | 26 |
| 226 | D | CA | 76 | 327 | 411 | 28 |
| 226 | D | C | 81 | 325 | 397 | 24 |
| 226 | D | O | 82 | 314 | 392 | 22 |
| 226 | D | CB | 85 | 320 | 421 | 32 |
| 226 | D | CG | 100 | 323 | 419 | 34 |
| 226 | D | OD1 | 103 | 335 | 418 | 37 |
| 226 | D | OD2 | 108 | 314 | 418 | 38 |
| 227 | T | N | 83 | 336 | 390 | 23 |
| 227 | T | CA | 89 | 336 | 377 | 25 |
| 227 | T | C | 104 | 336 | 377 | 25 |
| 227 | T | O | 110 | 344 | 384 | 26 |
| 227 | T | CB | 84 | 349 | 369 | 29 |
| 227 | T | OG1 | 70 | 349 | 368 | 23 |
| 227 | T | CG2 | 90 | 349 | 354 | 22 |
| 228 | R | N | 110 | 327 | 370 | 27 |
| 228 | R | CA | 124 | 325 | 369 | 32 |
| 228 | R | C | 131 | 338 | 362 | 33 |
| 228 | R | O | 128 | 340 | 351 | 38 |
| 228 | R | CB | 128 | 313 | 360 | 35 |
| 228 | R | CG | 142 | 313 | 355 | 45 |
| 228 | R | CD | 143 | 303 | 343 | 54 |
| 228 | R | NE | 143 | 289 | 348 | 64 |
| 228 | R | CZ | 133 | 280 | 344 | 65 |
| 228 | R | NH1 | 123 | 284 | 336 | 65 |
| 228 | R | NH2 | 134 | 268 | 349 | 64 |
| 229 | C | N | 138 | 345 | 370 | 31 |
| 229 | C | CA | 145 | 357 | 365 | 31 |
| 229 | C | C | 135 | 366 | 357 | 29 |
| 229 | C | O | 137 | 369 | 345 | 26 |
| 229 | C | CB | 157 | 353 | 357 | 33 |
| 229 | C | SG | 167 | 366 | 351 | 47 |
| 230 | F | N | 125 | 371 | 364 | 25 |
| 230 | F | CA | 114 | 380 | 358 | 23 |
| 230 | F | C | 120 | 391 | 349 | 22 |
| 230 | F | O | 115 | 392 | 338 | 21 |
| 230 | F | CB | 105 | 386 | 369 | 21 |
| 230 | F | CG | 93 | 393 | 363 | 17 |
| 230 | F | CD1 | 93 | 406 | 359 | 13 |
| 230 | F | CD2 | 81 | 386 | 363 | 21 |
| 230 | F | CE1 | 81 | 412 | 355 | 15 |
| 230 | F | CE2 | 69 | 392 | 358 | 16 |
| 230 | F | CZ | 69 | 405 | 354 | 13 |
| 231 | D | N | 130 | 398 | 354 | 20 |
| 231 | D | CA | 136 | 409 | 346 | 20 |
| 231 | D | C | 140 | 405 | 332 | 18 |
| 231 | D | O | 138 | 412 | 322 | 17 |
| 231 | D | CB | 148 | 415 | 353 | 22 |
| 231 | D | CG | 144 | 426 | 363 | 23 |
| 231 | D | OD1 | 132 | 427 | 367 | 23 |
| 231 | D | OD2 | 153 | 434 | 367 | 20 |
| 232 | S | N | 145 | 393 | 330 | 18 |
| 232 | S | CA | 150 | 388 | 317 | 22 |
| 232 | S | C | 138 | 382 | 309 | 24 |
| 232 | S | O | 140 | 381 | 296 | 26 |
| 232 | S | CB | 160 | 377 | 319 | 24 |
| 232 | S | OG | 172 | 383 | 323 | 28 |
| 233 | T | N | 127 | 379 | 315 | 25 |
| 233 | T | CA | 115 | 374 | 307 | 21 |
| 233 | T | C | 108 | 386 | 301 | 19 |
| 233 | T | O | 99 | 384 | 292 | 18 |
| 233 | T | CB | 106 | 365 | 316 | 21 |
| 233 | T | OG1 | 99 | 374 | 326 | 19 |
| 233 | T | CG2 | 113 | 354 | 323 | 21 |
| 234 | V | N | 110 | 398 | 306 | 15 |
| 234 | V | CA | 104 | 410 | 300 | 15 |
| 234 | V | C | 109 | 414 | 286 | 19 |
| 234 | V | O | 121 | 417 | 285 | 19 |
| 234 | V | CB | 105 | 422 | 310 | 14 |
| 234 | V | CG1 | 100 | 435 | 304 | 13 |
| 234 | V | CG2 | 98 | 418 | 323 | 15 |
| 235 | T | N | 101 | 413 | 277 | 18 |
| 235 | T | CA | 103 | 415 | 262 | 17 |
| 235 | T | C | 101 | 429 | 258 | 17 |
| 235 | T | O | 95 | 437 | 265 | 15 |
| 235 | T | CB | 95 | 406 | 254 | 17 |
| 235 | T | OG1 | 81 | 410 | 255 | 19 |
| 235 | T | CG2 | 96 | 391 | 259 | 14 |
| 236 | E | N | 105 | 432 | 245 | 17 |
| 236 | E | CA | 102 | 446 | 239 | 16 |
| 236 | E | C | 87 | 448 | 238 | 9 |
| 236 | E | O | 83 | 459 | 240 | 11 |
| 236 | E | CB | 109 | 447 | 225 | 14 |
| 236 | E | CG | 106 | 461 | 219 | 21 |
| 236 | E | CD | 113 | 462 | 205 | 26 |
| 236 | E | OE1 | 125 | 458 | 204 | 29 |
| 236 | E | OE2 | 108 | 469 | 196 | 28 |
| 237 | N | N | 80 | 438 | 235 | 11 |
| 237 | N | CA | 65 | 439 | 234 | 17 |
| 237 | N | C | 60 | 444 | 248 | 17 |
| 237 | N | O | 54 | 454 | 249 | 17 |
| 237 | N | CB | 59 | 425 | 230 | 16 |
| 237 | N | CG | 44 | 425 | 233 | 23 |
| 237 | N | OD1 | 36 | 431 | 225 | 22 |
| 237 | N | ND2 | 40 | 419 | 244 | 18 |
| 238 | D | N | 64 | 437 | 258 | 19 |
| 238 | D | CA | 60 | 440 | 272 | 17 |
| 238 | D | C | 63 | 455 | 276 | 16 |
| 238 | D | O | 54 | 461 | 280 | 20 |
| 238 | D | CB | 68 | 431 | 282 | 20 |
| 238 | D | CG | 64 | 417 | 281 | 19 |
| 238 | D | OD1 | 53 | 414 | 275 | 21 |
| 238 | D | OD2 | 71 | 408 | 286 | 20 |
| 239 | I | N | 75 | 459 | 273 | 16 |
| 239 | I | CA | 79 | 473 | 275 | 14 |
| 239 | I | C | 71 | 483 | 267 | 14 |
| 239 | I | O | 67 | 494 | 272 | 16 |
| 239 | I | CB | 94 | 475 | 274 | 10 |
| 239 | I | CG1 | 102 | 468 | 285 | 16 |
| 239 | I | CG2 | 98 | 490 | 274 | 8 |
| 239 | I | CD1 | 114 | 460 | 280 | 15 |
| 240 | R | N | 67 | 480 | 255 | 19 |
| 240 | R | CA | 59 | 489 | 246 | 19 |
| 240 | R | C | 44 | 489 | 251 | 13 |
| 240 | R | O | 38 | 499 | 251 | 14 |
| 240 | R | CB | 60 | 485 | 232 | 18 |
| 240 | R | CG | 73 | 488 | 225 | 22 |
| 240 | R | CD | 73 | 485 | 210 | 24 |
| 240 | R | NE | 86 | 488 | 204 | 20 |
| 240 | R | CZ | 91 | 500 | 201 | 17 |
| 240 | R | NH1 | 85 | 511 | 204 | 17 |
| 240 | R | NH2 | 104 | 500 | 197 | 19 |
| 241 | V | N | 39 | 477 | 256 | 15 |
| 241 | V | CA | 26 | 476 | 261 | 14 |
| 241 | V | C | 25 | 485 | 274 | 15 |
| 241 | V | O | 16 | 493 | 276 | 17 |
| 241 | V | CB | 22 | 462 | 264 | 12 |
| 241 | V | CG1 | 9 | 461 | 273 | 18 |
| 241 | V | CG2 | 19 | 454 | 251 | 11 |
| 242 | E | N | 36 | 485 | 282 | 19 |
| 242 | E | CA | 37 | 494 | 293 | 15 |
| 242 | E | C | 36 | 509 | 289 | 14 |
| 242 | E | O | 29 | 517 | 296 | 13 |
| 242 | E | CB | 50 | 492 | 301 | 11 |
| 242 | E | CG | 51 | 479 | 308 | 15 |
| 242 | E | CD | 65 | 475 | 311 | 18 |
| 242 | E | OE1 | 74 | 483 | 311 | 20 |
| 242 | E | OE2 | 67 | 463 | 314 | 24 |
| 243 | E | N | 42 | 512 | 279 | 18 |
| 243 | E | CA | 42 | 526 | 275 | 17 |
| 243 | E | C | 28 | 530 | 270 | 14 |
| 243 | E | O | 23 | 541 | 272 | 14 |
| 243 | E | CB | 52 | 529 | 264 | 16 |
| 243 | E | CG | 55 | 544 | 262 | 20 |
| 243 | E | CD | 56 | 548 | 248 | 25 |
| 243 | E | OE1 | 62 | 541 | 240 | 33 |
| 243 | E | OE2 | 51 | 559 | 244 | 25 |
| 244 | S | N | 21 | 521 | 263 | 17 |
| 244 | S | CA | 7 | 524 | 258 | 19 |
| 244 | S | C | −1 | 526 | 270 | 20 |
| 244 | S | O | −10 | 535 | 269 | 20 |
| 244 | S | CB | 2 | 513 | 249 | 16 |
| 244 | S | OG | 0 | 501 | 256 | 21 |
| 245 | I | N | 0 | 519 | 281 | 21 |

TABLE 1-continued

| | | | | | |
|---|---|---|---|---|---|
| 245 I | CA | −7 | 521 | 293 | 16 |
| 245 I | C | −5 | 535 | 299 | 18 |
| 245 I | O | −14 | 542 | 301 | 19 |
| 245 I | CB | −5 | 510 | 303 | 16 |
| 245 I | CG1 | −7 | 496 | 296 | 13 |
| 245 I | CG2 | −13 | 512 | 316 | 14 |
| 245 I | CD1 | −3 | 484 | 304 | 18 |
| 246 Y | N | 7 | 538 | 300 | 19 |
| 246 Y | CA | 11 | 552 | 306 | 18 |
| 246 Y | C | 5 | 562 | 297 | 20 |
| 246 Y | O | 0 | 573 | 301 | 20 |
| 246 Y | CB | 26 | 554 | 306 | 17 |
| 246 Y | CG | 34 | 544 | 313 | 19 |
| 246 Y | CD1 | 30 | 536 | 323 | 18 |
| 246 Y | CD2 | 48 | 542 | 309 | 17 |
| 246 Y | CE1 | 38 | 527 | 330 | 20 |
| 246 Y | CE2 | 56 | 533 | 315 | 19 |
| 246 Y | CZ | 51 | 525 | 325 | 19 |
| 246 Y | OH | 59 | 515 | 331 | 19 |
| 247 Q | N | 5 | 560 | 283 | 19 |
| 247 Q | CA | 0 | 570 | 274 | 20 |
| 247 Q | C | −14 | 572 | 274 | 21 |
| 247 Q | O | −19 | 581 | 268 | 21 |
| 247 Q | CB | 5 | 567 | 260 | 20 |
| 247 Q | CG | 20 | 569 | 257 | 19 |
| 247 Q | CD | 26 | 583 | 258 | 19 |
| 247 Q | OE1 | 18 | 593 | 260 | 21 |
| 247 Q | NE2 | 39 | 585 | 257 | 22 |
| 248 C | N | −21 | 563 | 281 | 22 |
| 248 C | CA | −36 | 564 | 283 | 21 |
| 248 C | C | −39 | 576 | 292 | 21 |
| 248 C | O | −50 | 582 | 291 | 26 |
| 248 C | CB | −42 | 551 | 288 | 19 |
| 248 C | SG | −43 | 538 | 276 | 22 |
| 249 C | N | −30 | 578 | 302 | 20 |
| 249 C | CA | −32 | 589 | 311 | 19 |
| 249 C | C | −34 | 603 | 305 | 22 |
| 249 C | O | −31 | 604 | 293 | 26 |
| 249 C | CB | −20 | 590 | 321 | 17 |
| 249 C | SG | −17 | 575 | 330 | 21 |
| 250 D | N | −40 | 612 | 312 | 19 |
| 250 D | CA | −41 | 626 | 307 | 21 |
| 250 D | C | −28 | 632 | 311 | 20 |
| 250 D | O | −26 | 635 | 323 | 22 |
| 250 D | CB | −53 | 632 | 315 | 25 |
| 250 D | CG | −55 | 647 | 311 | 27 |
| 250 D | OD1 | 46 | 653 | 306 | 34 |
| 250 D | OD2 | −66 | 652 | 314 | 34 |
| 251 L | N | −19 | 634 | 301 | 23 |
| 251 L | CA | −6 | 640 | 303 | 21 |
| 251 L | C | −3 | 653 | 294 | 22 |
| 251 L | O | −9 | 655 | 284 | 23 |
| 251 L | CB | 4 | 630 | 300 | 18 |
| 251 L | CG | 3 | 616 | 306 | 20 |
| 251 L | CD1 | 9 | 606 | 296 | 20 |
| 251 L | CD2 | 11 | 616 | 319 | 22 |
| 252 A | N | 5 | 661 | 299 | 23 |
| 252 A | CA | 10 | 672 | 291 | 26 |
| 252 A | C | 17 | 667 | 279 | 29 |
| 252 A | O | 24 | 656 | 280 | 28 |
| 252 A | CB | 20 | 681 | 300 | 24 |
| 253 P | N | 16 | 673 | 267 | 31 |
| 253 P | CA | 22 | 668 | 255 | 29 |
| 253 P | C | 38 | 667 | 257 | 26 |
| 253 P | O | 44 | 658 | 251 | 23 |
| 253 P | CB | 19 | 679 | 245 | 32 |
| 253 P | CG | 5 | 683 | 249 | 31 |
| 253 P | CD | 7 | 684 | 264 | 32 |
| 254 E | N | 44 | 675 | 265 | 29 |
| 254 E | CA | 58 | 674 | 268 | 27 |
| 254 E | C | 62 | 662 | 276 | 27 |
| 254 E | O | 72 | 656 | 274 | 28 |
| 254 E | CB | 62 | 687 | 276 | 28 |
| 254 E | CG | 78 | 688 | 278 | 31 |
| 254 E | CD | 82 | 700 | 285 | 34 |
| 254 E | OE1 | 75 | 705 | 294 | 41 |
| 254 E | OE2 | 92 | 706 | 281 | 38 |
| 255 A | N | 52 | 657 | 284 | 24 |
| 255 A | CA | 55 | 645 | 292 | 22 |
| 255 A | C | 52 | 632 | 283 | 18 |
| 255 A | O | 59 | 622 | 284 | 18 |
| 255 A | CB | 45 | 644 | 304 | 20 |
| 256 R | N | 43 | 633 | 273 | 19 |
| 256 R | CA | 40 | 622 | 264 | 19 |
| 256 R | C | 53 | 620 | 256 | 17 |
| 256 R | O | 56 | 608 | 253 | 18 |
| 256 R | CB | 29 | 625 | 255 | 18 |
| 256 R | CG | 16 | 628 | 261 | 21 |
| 256 R | CD | 5 | 628 | 251 | 24 |
| 256 R | NE | −8 | 629 | 258 | 26 |
| 256 R | CZ | −14 | 619 | 263 | 24 |
| 256 R | NH1 | −8 | 607 | 264 | 23 |
| 256 R | NH2 | −26 | 621 | 269 | 23 |
| 257 Q | N | 59 | 631 | 252 | 18 |
| 257 Q | CA | 71 | 631 | 243 | 21 |
| 257 Q | C | 83 | 625 | 251 | 16 |
| 257 Q | O | 89 | 615 | 247 | 17 |
| 257 Q | CB | 75 | 645 | 238 | 19 |
| 257 Q | CG | 87 | 645 | 229 | 21 |
| 257 Q | CD | 85 | 639 | 215 | 22 |
| 257 Q | OE1 | 75 | 632 | 213 | 23 |
| 257 Q | NE2 | 94 | 642 | 206 | 28 |
| 258 A | N | 84 | 630 | 263 | 19 |
| 258 A | CA | 95 | 625 | 272 | 17 |
| 258 A | C | 93 | 610 | 275 | 17 |
| 258 A | O | 103 | 602 | 276 | 18 |
| 258 A | CB | 96 | 633 | 285 | 15 |
| 259 I | N | 81 | 605 | 277 | 16 |
| 259 I | CA | 78 | 591 | 280 | 15 |
| 259 I | C | 81 | 582 | 268 | 19 |
| 259 I | O | 86 | 571 | 269 | 19 |
| 259 I | CB | 64 | 589 | 285 | 18 |
| 259 I | CG1 | 62 | 596 | 299 | 17 |
| 259 I | CG2 | 61 | 574 | 287 | 18 |
| 259 I | CD1 | 48 | 597 | 304 | 19 |
| 260 K | N | 77 | 587 | 256 | 18 |
| 260 K | CA | 79 | 580 | 244 | 19 |
| 260 K | C | 94 | 578 | 242 | 14 |
| 260 K | O | 99 | 567 | 239 | 14 |
| 260 K | CB | 73 | 587 | 232 | 22 |
| 260 K | CG | 76 | 582 | 218 | 23 |
| 260 K | CD | 67 | 589 | 208 | 27 |
| 260 K | CE | 70 | 585 | 194 | 37 |
| 260 K | NZ | 82 | 592 | 189 | 40 |
| 261 S | N | 101 | 589 | 243 | 16 |
| 261 S | CA | 116 | 590 | 242 | 17 |
| 261 S | C | 123 | 580 | 252 | 18 |
| 261 S | O | 131 | 572 | 247 | 15 |
| 261 S | CB | 120 | 604 | 243 | 16 |
| 261 S | OG | 134 | 606 | 240 | 24 |
| 262 L | N | 120 | 581 | 265 | 17 |
| 262 L | CA | 126 | 573 | 275 | 15 |
| 262 L | C | 123 | 558 | 272 | 14 |
| 262 L | O | 132 | 550 | 274 | 15 |
| 262 L | CB | 121 | 576 | 289 | 14 |
| 262 L | CG | 127 | 589 | 296 | 16 |
| 262 L | CD1 | 119 | 593 | 308 | 14 |
| 262 L | CD2 | 142 | 587 | 299 | 16 |
| 263 T | N | 111 | 555 | 267 | 14 |
| 263 T | CA | 108 | 542 | 263 | 14 |
| 263 T | C | 117 | 536 | 252 | 14 |
| 263 T | O | 122 | 525 | 253 | 18 |
| 263 T | CB | 93 | 540 | 259 | 16 |
| 263 T | OG1 | 85 | 543 | 271 | 19 |
| 263 T | CG2 | 90 | 525 | 255 | 12 |
| 264 E | N | 118 | 544 | 241 | 16 |
| 264 E | CA | 126 | 540 | 230 | 18 |
| 264 E | C | 141 | 538 | 233 | 16 |
| 264 E | O | 147 | 528 | 232 | 20 |
| 264 E | CB | 124 | 550 | 218 | 19 |
| 264 E | CG | 111 | 551 | 211 | 29 |
| 264 E | CD | 105 | 539 | 204 | 30 |
| 264 E | OE1 | 113 | 530 | 200 | 31 |
| 264 E | OE2 | 93 | 538 | 203 | 35 |
| 265 R | N | 146 | 549 | 238 | 16 |
| 265 R | CA | 160 | 551 | 241 | 15 |
| 265 R | C | 165 | 544 | 253 | 19 |
| 265 R | O | 177 | 540 | 254 | 20 |

TABLE 1-continued

| | | | | | |
|---|---|---|---|---|---|
| 265 R | CB | 163 | 566 | 242 | 13 |
| 265 R | CG | 158 | 573 | 230 | 12 |
| 265 R | CD | 161 | 588 | 231 | 11 |
| 265 R | NE | 175 | 591 | 233 | 16 |
| 265 R | CZ | 180 | 603 | 235 | 15 |
| 265 R | NH1 | 172 | 613 | 235 | 16 |
| 265 R | NH2 | 193 | 604 | 236 | 18 |
| 266 L | N | 157 | 542 | 264 | 18 |
| 266 L | CA | 162 | 536 | 276 | 17 |
| 266 L | C | 155 | 523 | 281 | 16 |
| 266 L | O | 161 | 512 | 282 | 14 |
| 266 L | CB | 162 | 546 | 288 | 16 |
| 266 L | CG | 166 | 543 | 302 | 14 |
| 266 L | CD1 | 180 | 538 | 303 | 15 |
| 266 L | CD2 | 163 | 555 | 310 | 13 |
| 267 Y | N | 142 | 523 | 282 | 17 |
| 267 Y | CA | 134 | 512 | 287 | 16 |
| 267 Y | C | 134 | 499 | 279 | 15 |
| 267 Y | O | 136 | 488 | 285 | 15 |
| 267 Y | CB | 120 | 516 | 291 | 16 |
| 267 Y | CG | 119 | 528 | 300 | 17 |
| 267 Y | CD1 | 130 | 529 | 310 | 14 |
| 267 Y | CD2 | 109 | 537 | 300 | 13 |
| 267 Y | CE1 | 130 | 540 | 319 | 15 |
| 267 Y | CE2 | 109 | 548 | 309 | 14 |
| 267 Y | CZ | 119 | 549 | 319 | 16 |
| 267 Y | OH | 120 | 559 | 328 | 14 |
| 268 I | N | 133 | 500 | 266 | 15 |
| 268 I | CA | 133 | 488 | 258 | 15 |
| 268 I | C | 147 | 481 | 258 | 15 |
| 268 I | O | 147 | 469 | 257 | 15 |
| 268 I | CB | 128 | 492 | 243 | 20 |
| 268 I | CG1 | 114 | 496 | 243 | 20 |
| 268 I | CG2 | 131 | 481 | 233 | 24 |
| 268 I | CD1 | 109 | 502 | 230 | 25 |
| 269 G | N | 158 | 489 | 258 | 17 |
| 269 G | CA | 171 | 482 | 257 | 14 |
| 269 G | C | 182 | 493 | 256 | 12 |
| 269 G | O | 179 | 505 | 256 | 13 |
| 270 G | N | 194 | 488 | 255 | 15 |
| 270 G | CA | 205 | 497 | 255 | 16 |
| 270 G | C | 219 | 491 | 258 | 17 |
| 270 G | O | 220 | 480 | 263 | 17 |
| 271 P | N | 230 | 498 | 254 | 19 |
| 271 P | CA | 243 | 493 | 257 | 20 |
| 271 P | C | 247 | 493 | 272 | 19 |
| 271 P | O | 243 | 501 | 279 | 15 |
| 271 P | CB | 253 | 502 | 248 | 19 |
| 271 P | CG | 246 | 515 | 249 | 23 |
| 271 P | CD | 231 | 511 | 247 | 20 |
| 272 L | N | 254 | 482 | 276 | 21 |
| 272 L | CA | 259 | 480 | 289 | 20 |
| 272 L | C | 274 | 484 | 290 | 22 |
| 272 L | O | 282 | 477 | 284 | 25 |
| 272 L | CB | 256 | 465 | 293 | 18 |
| 272 L | CG | 242 | 460 | 291 | 14 |
| 272 L | CD1 | 242 | 445 | 291 | 10 |
| 272 L | CD2 | 233 | 466 | 301 | 19 |
| 273 T | N | 277 | 493 | 299 | 21 |
| 273 T | CA | 291 | 498 | 300 | 22 |
| 273 T | C | 296 | 495 | 315 | 24 |
| 273 T | O | 290 | 498 | 325 | 24 |
| 273 T | CB | 292 | 513 | 298 | 23 |
| 273 T | OG1 | 288 | 516 | 284 | 26 |
| 273 T | CG2 | 307 | 518 | 300 | 24 |
| 274 N | N | 307 | 487 | 316 | 22 |
| 274 N | CA | 313 | 484 | 329 | 19 |
| 274 N | C | 319 | 497 | 336 | 20 |
| 274 N | O | 320 | 507 | 330 | 21 |
| 274 N | CB | 323 | 472 | 329 | 19 |
| 274 N | CG | 337 | 476 | 323 | 15 |
| 274 N | OD1 | 342 | 487 | 323 | 18 |
| 274 N | ND2 | 345 | 466 | 320 | 14 |
| 275 S | N | 323 | 495 | 349 | 23 |
| 275 S | CA | 329 | 507 | 356 | 24 |
| 275 S | C | 342 | 513 | 351 | 27 |
| 275 S | O | 345 | 524 | 355 | 28 |
| 275 S | CB | 330 | 503 | 371 | 29 |
| 275 S | OG | 340 | 493 | 373 | 29 |
| 276 K | N | 349 | 505 | 342 | 28 |
| 276 K | CA | 361 | 510 | 337 | 29 |
| 276 K | C | 359 | 517 | 323 | 29 |
| 276 K | O | 368 | 523 | 317 | 27 |
| 276 K | CB | 371 | 499 | 335 | 31 |
| 276 K | CG | 376 | 493 | 348 | 37 |
| 276 K | CD | 387 | 483 | 346 | 43 |
| 276 K | CE | 384 | 472 | 337 | 48 |
| 276 K | NZ | 394 | 461 | 335 | 49 |
| 277 G | N | 346 | 518 | 319 | 30 |
| 277 G | CA | 342 | 524 | 307 | 27 |
| 277 G | C | 343 | 515 | 294 | 27 |
| 277 G | O | 342 | 520 | 283 | 30 |
| 278 Q | N | 344 | 502 | 296 | 27 |
| 278 Q | CA | 344 | 493 | 285 | 28 |
| 278 Q | C | 330 | 487 | 282 | 30 |
| 278 Q | O | 322 | 484 | 291 | 25 |
| 278 Q | CB | 353 | 481 | 287 | 35 |
| 278 Q | CG | 367 | 484 | 292 | 41 |
| 278 Q | CD | 374 | 471 | 296 | 46 |
| 278 Q | OE1 | 375 | 467 | 307 | 47 |
| 278 Q | NE2 | 380 | 465 | 286 | 49 |
| 279 N | N | 326 | 486 | 269 | 27 |
| 279 N | CA | 314 | 480 | 266 | 25 |
| 279 N | C | 313 | 465 | 268 | 25 |
| 279 N | O | 320 | 457 | 262 | 23 |
| 279 N | CB | 311 | 483 | 251 | 28 |
| 279 N | CG | 298 | 477 | 246 | 31 |
| 279 N | OD1 | 298 | 470 | 236 | 36 |
| 279 N | ND2 | 287 | 479 | 253 | 36 |
| 280 C | N | 304 | 461 | 277 | 21 |
| 280 C | CA | 302 | 447 | 281 | 22 |
| 280 C | C | 292 | 440 | 272 | 19 |
| 280 C | O | 291 | 427 | 272 | 19 |
| 280 C | CB | 297 | 445 | 295 | 24 |
| 280 C | SG | 310 | 451 | 307 | 33 |
| 281 G | N | 283 | 447 | 265 | 21 |
| 281 G | CA | 273 | 441 | 257 | 20 |
| 281 G | C | 261 | 449 | 254 | 18 |
| 281 G | O | 261 | 462 | 255 | 17 |
| 282 Y | N | 249 | 442 | 253 | 21 |
| 282 Y | CA | 237 | 449 | 250 | 18 |
| 282 Y | C | 225 | 442 | 257 | 18 |
| 282 Y | O | 224 | 430 | 257 | 20 |
| 282 Y | CB | 234 | 449 | 235 | 19 |
| 282 Y | CG | 226 | 461 | 231 | 21 |
| 282 Y | CD1 | 231 | 473 | 229 | 16 |
| 282 Y | CD2 | 212 | 460 | 228 | 23 |
| 282 Y | CE1 | 224 | 484 | 225 | 20 |
| 282 Y | CE2 | 204 | 470 | 224 | 15 |
| 282 Y | CZ | 210 | 483 | 222 | 21 |
| 282 Y | OH | 202 | 493 | 219 | 26 |
| 283 R | N | 216 | 450 | 263 | 20 |
| 283 R | CA | 204 | 446 | 270 | 19 |
| 283 R | C | 191 | 448 | 262 | 22 |
| 283 R | O | 190 | 459 | 255 | 24 |
| 283 R | CB | 204 | 453 | 283 | 22 |
| 283 R | CG | 190 | 454 | 290 | 22 |
| 283 R | CD | 191 | 466 | 299 | 21 |
| 283 R | NE | 178 | 472 | 299 | 29 |
| 283 R | CZ | 175 | 485 | 295 | 21 |
| 283 R | NH1 | 184 | 493 | 291 | 16 |
| 283 R | NH2 | 162 | 489 | 295 | 27 |
| 284 R | N | 182 | 438 | 262 | 23 |
| 284 R | CA | 170 | 439 | 255 | 24 |
| 284 R | C | 158 | 434 | 264 | 22 |
| 284 R | O | 149 | 428 | 260 | 25 |
| 284 R | CB | 170 | 431 | 242 | 21 |
| 284 R | CG | 180 | 437 | 231 | 28 |
| 284 R | CD | 179 | 429 | 218 | 35 |
| 284 R | NE | 192 | 431 | 211 | 45 |
| 284 R | CZ | 194 | 441 | 203 | 53 |
| 284 R | NH1 | 185 | 451 | 201 | 54 |
| 284 R | NH2 | 206 | 442 | 197 | 55 |
| 285 C | N | 160 | 437 | 277 | 20 |
| 285 C | CA | 150 | 432 | 287 | 17 |
| 285 C | C | 149 | 443 | 297 | 11 |
| 285 C | O | 155 | 454 | 295 | 13 |
| 285 C | CB | 154 | 419 | 293 | 20 |

TABLE 1-continued

| | | | | | |
|---|---|---|---|---|---|
| 285 C | SG | 170 | 419 | 302 | 16 |
| 286 R | N | 142 | 441 | 308 | 14 |
| 286 R | CA | 141 | 451 | 318 | 15 |
| 286 R | C | 154 | 455 | 325 | 16 |
| 286 R | O | 161 | 446 | 329 | 17 |
| 286 R | CB | 131 | 447 | 329 | 17 |
| 286 R | CG | 131 | 455 | 342 | 14 |
| 286 R | CD | 120 | 467 | 341 | 17 |
| 286 R | NE | 107 | 461 | 341 | 20 |
| 286 R | CZ | 97 | 464 | 333 | 18 |
| 286 R | NH1 | 99 | 474 | 324 | 21 |
| 286 R | NH2 | 86 | 458 | 333 | 19 |
| 287 A | N | 156 | 468 | 326 | 16 |
| 287 A | CA | 168 | 474 | 333 | 13 |
| 287 A | C | 163 | 474 | 348 | 18 |
| 287 A | O | 152 | 478 | 351 | 17 |
| 287 A | CB | 171 | 488 | 329 | 10 |
| 288 S | N | 172 | 469 | 357 | 19 |
| 288 S | CA | 169 | 469 | 371 | 21 |
| 288 S | C | 170 | 482 | 378 | 20 |
| 288 S | O | 164 | 484 | 389 | 23 |
| 288 S | CB | 177 | 458 | 378 | 23 |
| 288 S | OG | 191 | 462 | 377 | 27 |
| 289 G | N | 177 | 492 | 372 | 18 |
| 289 G | CA | 179 | 505 | 378 | 14 |
| 289 G | C | 172 | 517 | 372 | 16 |
| 289 G | O | 179 | 527 | 370 | 17 |
| 290 V | N | 159 | 516 | 369 | 17 |
| 290 V | CA | 152 | 527 | 363 | 16 |
| 290 V | C | 139 | 530 | 372 | 16 |
| 290 V | O | 135 | 521 | 379 | 15 |
| 290 V | CB | 148 | 526 | 348 | 13 |
| 290 V | CG1 | 161 | 527 | 339 | 13 |
| 290 V | CG2 | 141 | 513 | 345 | 8 |
| 291 L | N | 134 | 542 | 370 | 17 |
| 291 L | CA | 122 | 546 | 378 | 18 |
| 291 L | C | 110 | 537 | 375 | 20 |
| 291 L | O | 103 | 533 | 385 | 20 |
| 291 L | CB | 118 | 560 | 375 | 13 |
| 291 L | CG | 107 | 566 | 383 | 17 |
| 291 L | CD1 | 109 | 565 | 398 | 18 |
| 291 L | CD2 | 105 | 581 | 380 | 19 |
| 292 T | N | 109 | 532 | 363 | 20 |
| 292 T | CA | 98 | 523 | 360 | 19 |
| 292 T | C | 99 | 508 | 362 | 19 |
| 292 T | O | 90 | 501 | 359 | 19 |
| 292 T | CB | 94 | 525 | 345 | 18 |
| 292 T | OG1 | 106 | 524 | 337 | 20 |
| 292 T | CG2 | 88 | 539 | 342 | 16 |
| 293 T | N | 110 | 504 | 368 | 15 |
| 293 T | CA | 112 | 490 | 371 | 14 |
| 293 T | C | 101 | 483 | 379 | 14 |
| 293 T | O | 95 | 473 | 376 | 16 |
| 293 T | CB | 127 | 487 | 377 | 17 |
| 293 T | OG1 | 137 | 492 | 369 | 21 |
| 293 T | CG2 | 129 | 472 | 380 | 14 |
| 294 S | N | 97 | 490 | 390 | 14 |
| 294 S | CA | 86 | 485 | 399 | 15 |
| 294 S | C | 73 | 485 | 392 | 15 |
| 294 S | O | 66 | 475 | 391 | 14 |
| 294 S | CB | 86 | 493 | 412 | 14 |
| 294 S | OG | 78 | 487 | 422 | 17 |
| 295 C | N | 69 | 497 | 387 | 15 |
| 295 C | CA | 56 | 499 | 380 | 17 |
| 295 C | C | 54 | 489 | 368 | 18 |
| 295 C | O | 44 | 482 | 367 | 18 |
| 295 C | CB | 54 | 513 | 377 | 14 |
| 295 C | SG | 37 | 517 | 370 | 24 |
| 296 G | N | 64 | 489 | 359 | 18 |
| 296 G | CA | 63 | 481 | 347 | 14 |
| 296 G | C | 63 | 467 | 351 | 16 |
| 296 G | O | 55 | 459 | 345 | 16 |
| 297 N | N | 71 | 462 | 361 | 16 |
| 297 N | CA | 70 | 448 | 365 | 15 |
| 297 N | C | 57 | 445 | 371 | 12 |
| 297 N | O | 52 | 434 | 368 | 14 |
| 297 N | CB | 81 | 445 | 376 | 18 |
| 297 N | CG | 95 | 442 | 369 | 25 |
| 297 N | OD1 | 96 | 441 | 357 | 21 |
| 297 N | ND2 | 105 | 439 | 378 | 20 |
| 298 T | N | 51 | 454 | 379 | 14 |
| 298 T | CA | 37 | 451 | 385 | 16 |
| 298 T | C | 27 | 450 | 374 | 15 |
| 298 T | O | 19 | 441 | 373 | 17 |
| 298 T | CB | 34 | 461 | 396 | 21 |
| 298 T | OG1 | 45 | 463 | 405 | 23 |
| 298 T | CG2 | 22 | 456 | 404 | 18 |
| 299 L | N | 26 | 460 | 365 | 16 |
| 299 L | CA | 17 | 460 | 354 | 18 |
| 299 L | C | 18 | 448 | 345 | 20 |
| 299 L | O | 7 | 441 | 342 | 19 |
| 299 L | CB | 19 | 473 | 345 | 15 |
| 299 L | CG | 14 | 486 | 351 | 15 |
| 299 L | CD1 | 17 | 497 | 341 | 19 |
| 299 L | CD2 | 0 | 485 | 353 | 17 |
| 300 T | N | 30 | 444 | 342 | 19 |
| 300 T | CA | 32 | 432 | 333 | 16 |
| 300 T | C | 29 | 419 | 340 | 15 |
| 300 T | O | 24 | 410 | 335 | 15 |
| 300 T | CB | 47 | 433 | 327 | 21 |
| 300 T | OG1 | 48 | 443 | 318 | 25 |
| 300 T | CG2 | 50 | 420 | 320 | 21 |
| 301 C | N | 33 | 418 | 353 | 16 |
| 301 C | CA | 30 | 406 | 361 | 15 |
| 301 C | C | 14 | 405 | 362 | 11 |
| 301 C | O | 9 | 394 | 359 | 15 |
| 301 C | CB | 36 | 407 | 375 | 15 |
| 301 C | SG | 34 | 391 | 384 | 21 |
| 302 Y | N | 8 | 416 | 365 | 12 |
| 302 Y | CA | −6 | 416 | 366 | 18 |
| 302 Y | C | −13 | 412 | 353 | 17 |
| 302 Y | O | −23 | 405 | 352 | 17 |
| 302 Y | CB | −11 | 429 | 371 | 18 |
| 302 Y | CG | −26 | 431 | 372 | 20 |
| 302 Y | CD1 | −33 | 427 | 384 | 23 |
| 302 Y | CD2 | −33 | 437 | 362 | 23 |
| 302 Y | CE1 | −46 | 429 | 385 | 25 |
| 302 Y | CE2 | −47 | 439 | 363 | 24 |
| 302 Y | CZ | −54 | 435 | 375 | 25 |
| 302 Y | OH | −67 | 437 | 376 | 25 |
| 303 L | N | −8 | 418 | 342 | 17 |
| 303 L | CA | −14 | 416 | 328 | 17 |
| 303 L | C | −13 | 401 | 325 | 18 |
| 303 L | O | −23 | 395 | 323 | 18 |
| 303 L | CB | −6 | 424 | 318 | 15 |
| 303 L | CG | −9 | 422 | 303 | 18 |
| 303 L | CD1 | −24 | 422 | 300 | 11 |
| 303 L | CD2 | −2 | 433 | 295 | 13 |
| 304 K | N | −1 | 395 | 325 | 17 |
| 304 K | CA | 0 | 381 | 322 | 15 |
| 304 K | C | −6 | 372 | 332 | 18 |
| 304 K | O | −11 | 361 | 328 | 18 |
| 304 K | CB | 15 | 378 | 322 | 15 |
| 304 K | CG | 23 | 386 | 311 | 13 |
| 304 K | CD | 38 | 381 | 310 | 11 |
| 304 K | CE | 46 | 390 | 301 | 13 |
| 304 K | NZ | 60 | 385 | 299 | 15 |
| 305 A | N | −6 | 376 | 345 | 16 |
| 305 A | CA | −12 | 367 | 355 | 18 |
| 305 A | C | −27 | 367 | 354 | 15 |
| 305 A | O | −34 | 356 | 354 | 18 |
| 305 A | CB | −8 | 371 | 369 | 22 |
| 306 S | N | −33 | 379 | 352 | 17 |
| 306 S | CA | −48 | 380 | 350 | 19 |
| 306 S | C | −53 | 372 | 338 | 20 |
| 306 S | O | −62 | 364 | 339 | 15 |
| 306 S | CB | −52 | 394 | 348 | 18 |
| 306 S | OG | −49 | 403 | 359 | 22 |
| 307 A | N | −46 | 373 | 327 | 18 |
| 307 A | CA | −49 | 366 | 315 | 15 |
| 307 A | C | −47 | 351 | 316 | 17 |
| 307 A | O | −55 | 343 | 311 | 21 |
| 307 A | CB | −40 | 371 | 303 | 13 |
| 308 A | N | −37 | 346 | 324 | 16 |
| 308 A | CA | −34 | 332 | 326 | 14 |
| 308 A | C | −45 | 326 | 335 | 14 |
| 308 A | O | −48 | 314 | 334 | 16 |
| 308 A | CB | −21 | 330 | 332 | 15 |

TABLE 1-continued

| | | | | | |
|---|---|---|---|---|---|
| 309 C | N | −51 | 334 | 344 | 19 |
| 309 C | CA | −61 | 329 | 353 | 22 |
| 309 C | C | −74 | 326 | 344 | 20 |
| 309 C | O | −80 | 315 | 346 | 23 |
| 309 C | CB | −65 | 340 | 363 | 21 |
| 309 C | SG | −54 | 342 | 377 | 27 |
| 310 R | N | −77 | 335 | 335 | 24 |
| 310 R | CA | −88 | 332 | 326 | 22 |
| 310 R | C | −85 | 320 | 317 | 23 |
| 310 R | O | −93 | 311 | 316 | 24 |
| 310 R | CB | −90 | 345 | 317 | 17 |
| 310 R | CG | −93 | 357 | 325 | 16 |
| 310 R | CD | −97 | 368 | 316 | 14 |
| 310 R | NE | −99 | 380 | 324 | 18 |
| 310 R | CZ | −105 | 391 | 320 | 19 |
| 310 R | NH1 | −109 | 393 | 307 | 25 |
| 310 R | NH2 | −106 | 402 | 328 | 22 |
| 311 A | N | −72 | 319 | 312 | 25 |
| 311 A | CA | −68 | 307 | 305 | 25 |
| 311 A | C | −69 | 294 | 313 | 27 |
| 311 A | O | −73 | 284 | 307 | 27 |
| 311 A | CB | −54 | 309 | 300 | 24 |
| 312 A | N | −66 | 294 | 325 | 26 |
| 312 A | CA | −66 | 282 | 334 | 27 |
| 312 A | C | −80 | 280 | 339 | 27 |
| 312 A | O | −83 | 269 | 346 | 26 |
| 312 A | CB | −56 | 284 | 345 | 29 |
| 313 K | N | −89 | 289 | 337 | 29 |
| 313 K | CA | −103 | 289 | 342 | 30 |
| 313 K | C | −104 | 288 | 357 | 30 |
| 313 K | O | −112 | 280 | 362 | 29 |
| 313 K | CB | −111 | 277 | 335 | 33 |
| 313 K | CG | −111 | 278 | 320 | 36 |
| 313 K | CD | −116 | 264 | 314 | 39 |
| 313 K | CE | −106 | 254 | 315 | 48 |
| 313 K | NZ | −110 | 241 | 309 | 53 |
| 314 L | N | −96 | 296 | 363 | 29 |
| 314 L | CA | −96 | 297 | 378 | 29 |
| 314 L | C | −109 | 304 | 383 | 29 |
| 314 L | O | −113 | 314 | 376 | 33 |
| 314 L | CB | −83 | 304 | 383 | 28 |
| 314 L | CG | −71 | 296 | 387 | 29 |
| 314 L | CD1 | −69 | 285 | 377 | 32 |
| 314 L | CD2 | −58 | 304 | 388 | 26 |
| 315 Q | N | −115 | 299 | 393 | 31 |
| 315 Q | CA | −128 | 305 | 398 | 35 |
| 315 Q | C | −126 | 317 | 408 | 33 |
| 315 Q | O | −119 | 315 | 419 | 33 |
| 315 Q | CB | −136 | 294 | 405 | 42 |
| 315 Q | CG | −144 | 285 | 395 | 50 |
| 315 Q | CD | −155 | 293 | 388 | 56 |
| 315 Q | OE1 | −154 | 297 | 377 | 58 |
| 315 Q | NE2 | −166 | 295 | 395 | 57 |
| 316 D | N | −133 | 328 | 406 | 35 |
| 316 D | CA | −133 | 340 | 415 | 37 |
| 316 D | C | −119 | 342 | 420 | 37 |
| 316 D | O | −116 | 340 | 432 | 37 |
| 316 D | CB | −143 | 338 | 427 | 39 |
| 316 D | CG | −145 | 351 | 435 | 46 |
| 316 D | OD1 | −139 | 362 | 431 | 52 |
| 316 D | OD2 | −152 | 351 | 445 | 50 |
| 317 C | N | −110 | 347 | 411 | 35 |
| 317 C | CA | −96 | 350 | 415 | 30 |
| 317 C | C | −94 | 364 | 420 | 28 |
| 317 C | O | −100 | 373 | 415 | 27 |
| 317 C | CB | −87 | 348 | 403 | 28 |
| 317 C | SG | −87 | 332 | 397 | 30 |
| 318 T | N | −86 | 364 | 431 | 26 |
| 318 T | CA | −82 | 377 | 436 | 26 |
| 318 T | C | −67 | 376 | 437 | 25 |
| 318 T | O | −61 | 366 | 442 | 26 |
| 318 T | CB | −87 | 379 | 451 | 27 |
| 318 T | OG1 | −101 | 376 | 451 | 30 |
| 318 T | CG2 | −85 | 393 | 455 | 21 |
| 319 M | N | −60 | 386 | 431 | 24 |
| 319 M | CA | −45 | 386 | 431 | 26 |
| 319 M | C | −39 | 397 | 439 | 22 |
| 319 M | O | −46 | 407 | 442 | 20 |
| 319 M | CB | −40 | 386 | 417 | 28 |
| 319 M | CG | −45 | 374 | 409 | 36 |
| 319 M | SD | −40 | 377 | 389 | 41 |
| 319 M | CE | −31 | 395 | 390 | 34 |
| 320 L | N | −27 | 395 | 443 | 23 |
| 320 L | CA | −19 | 405 | 450 | 21 |
| 320 L | C | −6 | 406 | 443 | 18 |
| 320 L | O | 0 | 395 | 442 | 18 |
| 320 L | CB | −18 | 401 | 465 | 20 |
| 320 L | CG | −12 | 412 | 474 | 19 |
| 320 L | CD1 | −20 | 425 | 472 | 18 |
| 320 L | CD2 | −11 | 407 | 488 | 23 |
| 321 V | N | −2 | 417 | 437 | 20 |
| 321 V | CA | 9 | 418 | 430 | 19 |
| 321 V | C | 18 | 429 | 435 | 16 |
| 321 V | O | 14 | 441 | 438 | 16 |
| 321 V | CB | 6 | 421 | 414 | 18 |
| 321 V | CG1 | 18 | 419 | 406 | 17 |
| 321 V | CG2 | −5 | 412 | 410 | 18 |
| 322 N | N | 31 | 426 | 436 | 17 |
| 322 N | CA | 42 | 436 | 441 | 19 |
| 322 N | C | 53 | 433 | 431 | 19 |
| 322 N | O | 61 | 425 | 433 | 19 |
| 322 N | CB | 47 | 432 | 455 | 21 |
| 322 N | CG | 37 | 435 | 465 | 22 |
| 322 N | OD1 | 27 | 427 | 467 | 26 |
| 322 N | ND2 | 39 | 446 | 473 | 23 |
| 323 G | N | 53 | 441 | 420 | 20 |
| 323 G | CA | 64 | 439 | 410 | 19 |
| 323 G | C | 62 | 425 | 404 | 20 |
| 323 G | O | 52 | 421 | 400 | 20 |
| 324 D | N | 73 | 417 | 405 | 21 |
| 324 D | CA | 74 | 404 | 400 | 19 |
| 324 D | C | 68 | 393 | 409 | 22 |
| 324 D | O | 69 | 381 | 407 | 23 |
| 324 D | CB | 88 | 400 | 396 | 25 |
| 324 D | CG | 97 | 398 | 409 | 29 |
| 324 D | OD1 | 98 | 407 | 417 | 28 |
| 324 D | OD2 | 103 | 387 | 410 | 36 |
| 325 D | N | 64 | 398 | 421 | 22 |
| 325 D | CA | 59 | 388 | 431 | 23 |
| 325 D | C | 43 | 388 | 430 | 19 |
| 325 D | O | 36 | 398 | 430 | 15 |
| 325 D | CB | 63 | 393 | 445 | 27 |
| 325 D | CG | 64 | 381 | 455 | 35 |
| 325 D | OD1 | 54 | 375 | 458 | 39 |
| 325 D | OD2 | 76 | 378 | 458 | 38 |
| 326 L | N | 39 | 375 | 429 | 17 |
| 326 L | CA | 24 | 373 | 427 | 21 |
| 326 L | C | 18 | 363 | 436 | 18 |
| 326 L | O | 24 | 352 | 439 | 19 |
| 326 L | CB | 22 | 367 | 412 | 22 |
| 326 L | CG | 8 | 362 | 409 | 23 |
| 326 L | CD1 | −1 | 374 | 409 | 22 |
| 326 L | CD2 | 8 | 356 | 395 | 24 |
| 327 V | N | 6 | 365 | 441 | 21 |
| 327 V | CA | −1 | 356 | 449 | 22 |
| 327 V | C | −15 | 357 | 444 | 21 |
| 327 V | O | −21 | 367 | 441 | 18 |
| 327 V | CB | 0 | 360 | 464 | 20 |
| 327 V | CG1 | −12 | 365 | 470 | 27 |
| 327 V | CG2 | 5 | 348 | 472 | 21 |
| 328 V | N | −21 | 345 | 443 | 23 |
| 328 V | CA | −35 | 343 | 438 | 25 |
| 328 V | C | −43 | 335 | 448 | 24 |
| 328 V | O | −39 | 324 | 452 | 27 |
| 328 V | CB | −35 | 335 | 424 | 24 |
| 328 V | CG1 | −50 | 334 | 420 | 23 |
| 328 V | CG2 | −28 | 343 | 413 | 26 |
| 329 I | N | −55 | 341 | 451 | 27 |
| 329 I | CA | −65 | 334 | 460 | 26 |
| 329 I | C | −77 | 333 | 452 | 28 |
| 329 I | O | −82 | 342 | 445 | 26 |
| 329 I | CB | −67 | 342 | 473 | 27 |
| 329 I | CG1 | −54 | 343 | 482 | 25 |
| 329 I | CG2 | −79 | 336 | 481 | 21 |
| 329 I | CD1 | −55 | 352 | 493 | 24 |
| 330 C | N | −83 | 321 | 452 | 30 |
| 330 C | CA | −95 | 318 | 444 | 32 |
| 330 C | C | −104 | 308 | 451 | 34 |

TABLE 1-continued

| | | | | | |
|---|---|---|---|---|---|
| 330 | C | O | −101 | 303 | 462 | 33 |
| 330 | C | CB | −90 | 312 | 430 | 29 |
| 330 | C | SG | −81 | 296 | 432 | 31 |
| 331 | E | N | −114 | 304 | 444 | 34 |
| 331 | E | CA | −124 | 294 | 449 | 33 |
| 331 | E | C | −120 | 281 | 445 | 32 |
| 331 | E | O | −117 | 278 | 433 | 36 |
| 331 | E | CB | −138 | 298 | 443 | 31 |
| 331 | E | CG | −150 | 292 | 449 | 33 |
| 331 | E | CD | −152 | 297 | 463 | 31 |
| 331 | E | OE1 | −156 | 309 | 465 | 28 |
| 331 | E | OE2 | −151 | 289 | 472 | 31 |
| 332 | S | N | −118 | 272 | 454 | 32 |
| 332 | S | CA | −113 | 258 | 452 | 33 |
| 332 | S | C | −123 | 249 | 444 | 38 |
| 332 | S | O | −136 | 251 | 446 | 40 |
| 332 | S | CB | −109 | 251 | 464 | 33 |
| 332 | S | OG | −105 | 238 | 462 | 30 |
| 333 | A | N | −119 | 240 | 436 | 38 |
| 333 | A | CA | −127 | 231 | 429 | 39 |
| 333 | A | C | −122 | 216 | 431 | 40 |
| 333 | A | O | −124 | 208 | 423 | 46 |
| 333 | A | CB | −126 | 234 | 414 | 35 |
| 334 | G | N | −116 | 214 | 443 | 37 |
| 334 | G | CA | −111 | 201 | 446 | 36 |
| 334 | G | C | −96 | 200 | 444 | 37 |
| 334 | G | O | −91 | 206 | 434 | 39 |
| 335 | V | N | −89 | 193 | 453 | 37 |
| 335 | V | CA | −75 | 191 | 452 | 41 |
| 335 | V | C | −69 | 187 | 438 | 42 |
| 335 | V | O | −60 | 193 | 433 | 42 |
| 335 | V | CB | −69 | 182 | 464 | 41 |
| 335 | V | CG1 | −77 | 169 | 464 | 44 |
| 335 | V | CG2 | −54 | 180 | 462 | 44 |
| 336 | Q | N | −76 | 177 | 432 | 45 |
| 336 | Q | CA | −71 | 171 | 419 | 45 |
| 336 | Q | C | −74 | 181 | 408 | 44 |
| 336 | Q | O | −66 | 182 | 398 | 41 |
| 336 | Q | CB | −78 | 158 | 416 | 49 |
| 336 | Q | CG | −74 | 147 | 426 | 53 |
| 336 | Q | CD | −58 | 146 | 428 | 59 |
| 336 | Q | OE1 | −51 | 147 | 418 | 63 |
| 336 | Q | NE2 | −54 | 143 | 440 | 63 |
| 337 | E | N | −85 | 188 | 409 | 40 |
| 337 | E | CA | −88 | 198 | 399 | 39 |
| 337 | E | C | −79 | 210 | 401 | 41 |
| 337 | E | O | −74 | 216 | 391 | 40 |
| 337 | E | CB | −103 | 202 | 400 | 38 |
| 337 | E | CG | −108 | 211 | 388 | 43 |
| 337 | E | CD | −105 | 206 | 374 | 46 |
| 337 | E | OE1 | −106 | 194 | 371 | 41 |
| 337 | E | OE2 | −101 | 214 | 365 | 49 |
| 338 | D | N | −76 | 214 | 413 | 40 |
| 338 | D | CA | −67 | 225 | 417 | 34 |
| 338 | D | C | −53 | 223 | 411 | 31 |
| 338 | D | O | −47 | 233 | 407 | 31 |
| 338 | D | CB | −67 | 228 | 432 | 30 |
| 338 | D | CG | −80 | 234 | 437 | 31 |
| 338 | D | OD1 | −89 | 238 | 429 | 34 |
| 338 | D | OD2 | −82 | 236 | 449 | 31 |
| 339 | A | N | −48 | 211 | 411 | 29 |
| 339 | A | CA | −35 | 208 | 406 | 30 |
| 339 | A | C | −35 | 209 | 391 | 33 |
| 339 | A | O | −26 | 214 | 384 | 35 |
| 339 | A | CB | −31 | 194 | 410 | 30 |
| 340 | A | N | −47 | 206 | 385 | 32 |
| 340 | A | CA | −48 | 207 | 370 | 31 |
| 340 | A | C | −49 | 221 | 366 | 29 |
| 340 | A | O | −42 | 225 | 356 | 27 |
| 340 | A | CB | −61 | 199 | 366 | 28 |
| 341 | S | N | −56 | 230 | 373 | 28 |
| 341 | S | CA | −58 | 244 | 370 | 29 |
| 341 | S | C | −44 | 251 | 371 | 30 |
| 341 | S | O | −42 | 261 | 363 | 29 |
| 341 | S | CB | −68 | 250 | 379 | 28 |
| 341 | S | OG | −80 | 244 | 377 | 34 |
| 342 | L | N | −36 | 247 | 380 | 31 |
| 342 | L | CA | −22 | 253 | 382 | 29 |
| 342 | L | C | −13 | 250 | 371 | 27 |
| 342 | L | O | −5 | 259 | 367 | 28 |
| 342 | L | CB | −16 | 249 | 395 | 28 |
| 342 | L | CG | −17 | 259 | 407 | 25 |
| 342 | L | CD1 | −7 | 255 | 418 | 22 |
| 342 | L | CD2 | −14 | 272 | 402 | 28 |
| 343 | R | N | −14 | 238 | 366 | 26 |
| 343 | R | CA | −5 | 234 | 354 | 29 |
| 343 | R | C | −10 | 242 | 342 | 27 |
| 343 | R | O | −1 | 246 | 334 | 26 |
| 343 | R | CB | −7 | 219 | 351 | 31 |
| 343 | R | CG | 5 | 210 | 355 | 41 |
| 343 | R | CD | 2 | 195 | 353 | 47 |
| 343 | R | NE | −5 | 193 | 341 | 58 |
| 343 | R | CZ | −16 | 187 | 340 | 64 |
| 343 | R | NH1 | −22 | 182 | 351 | 67 |
| 343 | R | NH2 | −23 | 186 | 328 | 66 |
| 344 | A | N | −23 | 245 | 341 | 27 |
| 344 | A | CA | −28 | 253 | 330 | 24 |
| 344 | A | C | −24 | 267 | 331 | 24 |
| 344 | A | O | −20 | 274 | 321 | 24 |
| 344 | A | CB | −43 | 252 | 329 | 23 |
| 345 | F | N | −24 | 272 | 344 | 24 |
| 345 | F | CA | −20 | 286 | 346 | 22 |
| 345 | F | C | −5 | 288 | 343 | 20 |
| 345 | F | O | −1 | 297 | 336 | 23 |
| 345 | F | CB | −22 | 289 | 361 | 16 |
| 345 | F | CG | −17 | 303 | 365 | 17 |
| 345 | F | CD1 | −4 | 305 | 370 | 17 |
| 345 | F | CD2 | −26 | 314 | 365 | 16 |
| 345 | F | CE1 | 0 | 318 | 373 | 19 |
| 345 | F | CE2 | −22 | 327 | 368 | 15 |
| 345 | F | CZ | −9 | 329 | 373 | 17 |
| 346 | T | N | 3 | 278 | 347 | 20 |
| 346 | T | CA | 17 | 279 | 345 | 23 |
| 346 | T | C | 20 | 278 | 330 | 23 |
| 346 | T | O | 28 | 286 | 325 | 24 |
| 346 | T | CB | 24 | 267 | 352 | 22 |
| 346 | T | OG1 | 21 | 268 | 366 | 24 |
| 346 | T | CG2 | 39 | 268 | 349 | 21 |
| 347 | E | N | 13 | 270 | 323 | 23 |
| 347 | E | CA | 14 | 268 | 308 | 21 |
| 347 | E | C | 11 | 281 | 301 | 20 |
| 347 | E | O | 17 | 285 | 292 | 22 |
| 347 | E | CB | 5 | 257 | 303 | 21 |
| 347 | E | CG | 11 | 243 | 307 | 26 |
| 347 | E | CD | 1 | 232 | 305 | 35 |
| 347 | E | OE1 | −10 | 234 | 301 | 38 |
| 347 | E | OE2 | 5 | 220 | 308 | 40 |
| 348 | A | N | 1 | 288 | 307 | 17 |
| 348 | A | CA | −2 | 301 | 301 | 17 |
| 348 | A | C | 7 | 311 | 303 | 18 |
| 348 | A | O | 11 | 318 | 294 | 21 |
| 348 | A | CB | −16 | 305 | 306 | 17 |
| 349 | M | N | 12 | 311 | 316 | 21 |
| 349 | M | CA | 23 | 321 | 319 | 17 |
| 349 | M | C | 35 | 318 | 311 | 16 |
| 349 | M | O | 42 | 328 | 307 | 16 |
| 349 | M | CB | 27 | 319 | 334 | 20 |
| 349 | M | CG | 17 | 324 | 344 | 12 |
| 349 | M | SD | 14 | 344 | 343 | 22 |
| 349 | M | CE | 31 | 352 | 352 | 21 |
| 350 | T | N | 38 | 306 | 308 | 14 |
| 350 | T | CA | 50 | 302 | 300 | 21 |
| 350 | T | C | 48 | 308 | 285 | 24 |
| 350 | T | O | 58 | 314 | 280 | 21 |
| 350 | T | CB | 52 | 287 | 299 | 21 |
| 350 | T | OG1 | 53 | 282 | 313 | 25 |
| 350 | T | CG2 | 64 | 284 | 291 | 22 |
| 351 | R | N | 36 | 307 | 279 | 22 |
| 351 | R | CA | 34 | 312 | 266 | 20 |
| 351 | R | C | 36 | 327 | 265 | 18 |
| 351 | R | O | 39 | 332 | 255 | 20 |
| 351 | R | CB | 20 | 309 | 261 | 19 |
| 351 | R | CG | 17 | 295 | 257 | 19 |
| 351 | R | CD | 3 | 294 | 252 | 22 |
| 351 | R | NE | −2 | 282 | 258 | 34 |
| 351 | R | CZ | −12 | 281 | 267 | 30 |
| 351 | R | NH1 | −17 | 292 | 272 | 30 |
| 351 | R | NH2 | −15 | 269 | 272 | 33 |

TABLE 1-continued

| | | | | | | |
|---|---|---|---|---|---|---|
| 352 | Y | N | 33 | 333 | 276 | 19 |
| 352 | Y | CA | 34 | 348 | 277 | 16 |
| 352 | Y | C | 48 | 352 | 281 | 16 |
| 352 | Y | O | 51 | 363 | 284 | 20 |
| 352 | Y | CB | 25 | 353 | 288 | 18 |
| 352 | Y | CG | 10 | 351 | 286 | 22 |
| 352 | Y | CD1 | 5 | 351 | 273 | 21 |
| 352 | Y | CD2 | 1 | 349 | 297 | 21 |
| 352 | Y | CE1 | −8 | 349 | 271 | 22 |
| 352 | Y | CE2 | −11 | 347 | 295 | 23 |
| 352 | Y | CZ | −17 | 348 | 282 | 23 |
| 352 | Y | OH | −30 | 347 | 281 | 24 |
| 353 | S | N | 57 | 342 | 281 | 21 |
| 353 | S | CA | 71 | 344 | 284 | 26 |
| 353 | S | C | 75 | 345 | 299 | 28 |
| 353 | S | O | 85 | 351 | 302 | 35 |
| 353 | S | CB | 78 | 354 | 276 | 21 |
| 353 | S | OG | 79 | 367 | 282 | 28 |
| 354 | A | N | 66 | 340 | 308 | 26 |
| 354 | A | CA | 69 | 341 | 322 | 26 |
| 354 | A | C | 70 | 327 | 328 | 27 |
| 354 | A | O | 62 | 323 | 337 | 26 |
| 354 | A | CB | 59 | 349 | 329 | 23 |
| 355 | P | N | 80 | 319 | 324 | 28 |
| 355 | P | CA | 81 | 305 | 330 | 27 |
| 355 | P | C | 84 | 306 | 344 | 29 |
| 355 | P | O | 89 | 316 | 350 | 27 |
| 355 | P | CB | 93 | 300 | 321 | 23 |
| 355 | P | CG | 101 | 312 | 320 | 26 |
| 355 | P | CD | 92 | 322 | 316 | 29 |
| 356 | P | N | 81 | 295 | 352 | 32 |
| 356 | P | CA | 83 | 294 | 366 | 32 |
| 356 | P | C | 97 | 289 | 370 | 33 |
| 356 | P | O | 104 | 283 | 363 | 35 |
| 356 | P | CB | 73 | 284 | 370 | 34 |
| 356 | P | CG | 73 | 274 | 359 | 31 |
| 356 | P | CD | 73 | 284 | 347 | 34 |
| 357 | G | N | 101 | 294 | 382 | 33 |
| 357 | G | CA | 114 | 289 | 388 | 36 |
| 357 | G | C | 110 | 277 | 395 | 40 |
| 357 | G | O | 114 | 266 | 392 | 41 |
| 358 | D | N | 102 | 279 | 406 | 43 |
| 358 | D | CA | 97 | 268 | 414 | 45 |
| 358 | D | C | 83 | 265 | 409 | 42 |
| 358 | D | O | 75 | 274 | 407 | 41 |
| 358 | D | CB | 97 | 271 | 429 | 49 |
| 358 | D | CG | 110 | 274 | 435 | 52 |
| 358 | D | OD1 | 119 | 264 | 434 | 56 |
| 358 | D | OD2 | 113 | 285 | 440 | 55 |
| 359 | P | N | 80 | 252 | 408 | 41 |
| 359 | P | CA | 66 | 248 | 403 | 41 |
| 359 | P | C | 56 | 253 | 413 | 38 |
| 359 | P | O | 57 | 251 | 425 | 40 |
| 359 | P | CB | 66 | 233 | 403 | 43 |
| 359 | P | CG | 81 | 230 | 400 | 42 |
| 359 | P | CD | 88 | 240 | 409 | 41 |
| 360 | P | N | 46 | 261 | 409 | 36 |
| 360 | P | CA | 35 | 266 | 418 | 33 |
| 360 | P | C | 29 | 254 | 426 | 34 |
| 360 | P | O | 29 | 243 | 421 | 35 |
| 360 | P | CB | 25 | 272 | 409 | 35 |
| 360 | P | CG | 33 | 276 | 396 | 35 |
| 360 | P | CD | 42 | 264 | 395 | 33 |
| 361 | Q | N | 24 | 257 | 438 | 37 |
| 361 | Q | CA | 18 | 247 | 446 | 36 |
| 361 | Q | C | 5 | 252 | 452 | 30 |
| 361 | Q | O | 5 | 262 | 459 | 27 |
| 361 | Q | CB | 28 | 242 | 457 | 43 |
| 361 | Q | CG | 25 | 230 | 464 | 57 |
| 361 | Q | CD | 35 | 226 | 474 | 64 |
| 361 | Q | OE1 | 33 | 227 | 486 | 67 |
| 361 | Q | NE2 | 47 | 222 | 469 | 67 |
| 362 | P | N | −5 | 244 | 451 | 29 |
| 362 | P | CA | −18 | 248 | 457 | 27 |
| 362 | P | C | −17 | 247 | 472 | 25 |
| 362 | P | O | −13 | 237 | 478 | 26 |
| 362 | P | CB | −28 | 238 | 451 | 26 |
| 362 | P | CG | −21 | 231 | 440 | 25 |
| 362 | P | CD | −7 | 231 | 444 | 28 |
| 363 | E | N | −22 | 258 | 479 | 25 |
| 363 | E | CA | −21 | 258 | 493 | 27 |
| 363 | E | C | −35 | 260 | 499 | 28 |
| 363 | E | O | −43 | 268 | 494 | 25 |
| 363 | E | CB | −11 | 269 | 499 | 28 |
| 363 | E | CG | 2 | 266 | 496 | 29 |
| 363 | E | CD | 8 | 254 | 505 | 33 |
| 363 | E | OE1 | 1 | 249 | 514 | 33 |
| 363 | E | OE2 | 20 | 250 | 503 | 33 |
| 364 | Y | N | −38 | 253 | 510 | 31 |
| 364 | Y | CA | −51 | 254 | 516 | 34 |
| 364 | Y | C | −51 | 260 | 530 | 34 |
| 364 | Y | O | −61 | 260 | 538 | 34 |
| 364 | Y | CB | −59 | 240 | 516 | 35 |
| 364 | Y | CG | −60 | 235 | 502 | 37 |
| 364 | Y | CD1 | −71 | 238 | 494 | 36 |
| 364 | Y | CD2 | −50 | 226 | 497 | 35 |
| 364 | Y | CE1 | −72 | 234 | 481 | 34 |
| 364 | Y | CE2 | −51 | 222 | 483 | 34 |
| 364 | Y | CZ | −62 | 226 | 476 | 34 |
| 364 | Y | OH | −62 | 222 | 462 | 38 |
| 365 | D | N | −39 | 264 | 534 | 35 |
| 365 | D | CA | −36 | 271 | 547 | 35 |
| 365 | D | C | −30 | 284 | 544 | 33 |
| 365 | D | O | −19 | 284 | 538 | 34 |
| 365 | D | CB | −27 | 262 | 555 | 40 |
| 365 | D | CG | −25 | 267 | 570 | 48 |
| 365 | D | OD1 | −28 | 279 | 573 | 50 |
| 365 | D | OD2 | −19 | 259 | 578 | 53 |
| 366 | L | N | −37 | 295 | 547 | 32 |
| 366 | L | CA | −32 | 308 | 544 | 34 |
| 366 | L | C | −18 | 311 | 549 | 34 |
| 366 | L | O | −9 | 316 | 542 | 34 |
| 366 | L | CB | −41 | 319 | 549 | 32 |
| 366 | L | CG | −37 | 333 | 547 | 34 |
| 366 | L | CD1 | −34 | 336 | 532 | 35 |
| 366 | L | CD2 | −48 | 343 | 552 | 33 |
| 367 | E | N | −15 | 307 | 562 | 34 |
| 367 | E | CA | −2 | 308 | 568 | 35 |
| 367 | E | C | 8 | 301 | 561 | 34 |
| 367 | E | O | 20 | 304 | 563 | 30 |
| 367 | E | CB | −3 | 303 | 583 | 40 |
| 367 | E | CG | −13 | 310 | 592 | 45 |
| 367 | E | CD | −13 | 305 | 606 | 49 |
| 367 | E | OE1 | −2 | 302 | 611 | 51 |
| 367 | E | OE2 | −23 | 304 | 612 | 52 |
| 368 | L | N | 5 | 292 | 552 | 34 |
| 368 | L | CA | 15 | 284 | 545 | 33 |
| 368 | L | C | 19 | 290 | 531 | 32 |
| 368 | L | O | 26 | 284 | 524 | 32 |
| 368 | L | CB | 10 | 270 | 543 | 36 |
| 368 | L | CG | 9 | 263 | 556 | 36 |
| 368 | L | CD1 | 5 | 248 | 554 | 37 |
| 368 | L | CD2 | 22 | 263 | 563 | 37 |
| 369 | I | N | 13 | 302 | 528 | 31 |
| 369 | I | CA | 16 | 308 | 516 | 28 |
| 369 | I | C | 27 | 319 | 518 | 29 |
| 369 | I | O | 25 | 329 | 526 | 29 |
| 369 | I | CB | 4 | 314 | 509 | 26 |
| 369 | I | CG1 | −5 | 303 | 505 | 22 |
| 369 | I | CG2 | 8 | 323 | 497 | 21 |
| 369 | I | CD1 | −18 | 308 | 499 | 21 |
| 370 | T | N | 38 | 318 | 511 | 27 |
| 370 | T | CA | 49 | 328 | 511 | 28 |
| 370 | T | C | 48 | 337 | 499 | 27 |
| 370 | T | O | 50 | 332 | 488 | 30 |
| 370 | T | CB | 63 | 322 | 512 | 29 |
| 370 | T | OG1 | 64 | 314 | 525 | 27 |
| 370 | T | CG2 | 74 | 332 | 512 | 24 |
| 371 | S | N | 45 | 350 | 501 | 31 |
| 371 | S | CA | 45 | 360 | 490 | 32 |
| 371 | S | C | 52 | 372 | 496 | 34 |
| 371 | S | O | 50 | 376 | 507 | 30 |
| 371 | S | CB | 30 | 364 | 487 | 34 |
| 371 | S | OG | 23 | 369 | 499 | 33 |
| 372 | C | N | 62 | 377 | 488 | 34 |
| 372 | C | CA | 70 | 388 | 491 | 35 |
| 372 | C | C | 80 | 384 | 503 | 33 |
| 372 | C | O | 84 | 392 | 511 | 31 |

TABLE 1-continued

| | | | | | |
|---|---|---|---|---|---|
| 372 | C | CB | 62 | 400 | 496 | 35 |
| 372 | C | SG | 55 | 410 | 482 | 34 |
| 373 | S | N | 84 | 371 | 502 | 33 |
| 373 | S | CA | 93 | 365 | 512 | 35 |
| 373 | S | C | 86 | 364 | 527 | 35 |
| 373 | S | O | 93 | 361 | 536 | 35 |
| 373 | S | CB | 106 | 372 | 513 | 34 |
| 373 | S | OG | 114 | 370 | 501 | 33 |
| 374 | S | N | 73 | 367 | 527 | 30 |
| 374 | S | CA | 66 | 368 | 540 | 27 |
| 374 | S | C | 55 | 358 | 540 | 27 |
| 374 | S | O | 53 | 350 | 530 | 26 |
| 374 | S | CB | 61 | 382 | 541 | 28 |
| 374 | S | OG | 71 | 392 | 539 | 36 |
| 375 | N | N | 47 | 358 | 551 | 26 |
| 375 | N | CA | 36 | 349 | 553 | 24 |
| 375 | N | C | 28 | 355 | 565 | 26 |
| 375 | N | O | 33 | 363 | 573 | 25 |
| 375 | N | CB | 40 | 334 | 556 | 25 |
| 375 | N | CG | 46 | 332 | 569 | 28 |
| 375 | N | OD1 | 59 | 333 | 571 | 24 |
| 375 | N | ND2 | 39 | 328 | 579 | 27 |
| 376 | V | N | 15 | 351 | 566 | 26 |
| 376 | V | CA | 6 | 355 | 576 | 24 |
| 376 | V | C | 8 | 345 | 588 | 23 |
| 376 | V | O | 10 | 334 | 585 | 22 |
| 376 | V | CB | −8 | 356 | 571 | 27 |
| 376 | V | CG1 | −18 | 356 | 583 | 22 |
| 376 | V | CG2 | −11 | 368 | 562 | 23 |
| 377 | S | N | 7 | 351 | 600 | 23 |
| 377 | S | CA | 8 | 342 | 612 | 21 |
| 377 | S | C | 0 | 348 | 623 | 21 |
| 377 | S | O | −5 | 359 | 621 | 21 |
| 377 | S | CB | 23 | 341 | 617 | 15 |
| 377 | S | OG | 25 | 328 | 624 | 17 |
| 378 | V | N | −2 | 341 | 634 | 25 |
| 378 | V | CA | −11 | 345 | 645 | 27 |
| 378 | V | C | −4 | 346 | 659 | 24 |
| 378 | V | O | 4 | 338 | 662 | 23 |
| 378 | V | CB | −23 | 335 | 646 | 25 |
| 378 | V | CG1 | −35 | 341 | 654 | 26 |
| 378 | V | CG2 | −27 | 330 | 633 | 28 |
| 379 | A | N | −8 | 356 | 666 | 25 |
| 379 | A | CA | −3 | 359 | 680 | 26 |
| 379 | A | C | −16 | 363 | 687 | 29 |
| 379 | A | O | −27 | 361 | 682 | 29 |
| 379 | A | CB | 6 | 370 | 680 | 22 |
| 380 | H | N | −14 | 369 | 699 | 29 |
| 380 | H | CA | −26 | 373 | 707 | 27 |
| 380 | H | C | −22 | 386 | 714 | 28 |
| 380 | H | O | −11 | 387 | 720 | 31 |
| 380 | H | CB | −29 | 363 | 718 | 28 |
| 380 | H | CG | −33 | 350 | 712 | 30 |
| 380 | H | ND1 | −46 | 345 | 711 | 30 |
| 380 | H | CD2 | −25 | 339 | 708 | 30 |
| 380 | H | CE1 | −46 | 333 | 706 | 31 |
| 380 | H | NE2 | −33 | 329 | 704 | 34 |
| 381 | D | N | −30 | 396 | 713 | 27 |
| 381 | D | CA | −27 | 409 | 720 | 29 |
| 381 | D | C | −29 | 409 | 735 | 31 |
| 381 | D | O | −32 | 398 | 740 | 32 |
| 381 | D | CB | −36 | 420 | 714 | 32 |
| 381 | D | CG | −51 | 419 | 717 | 37 |
| 381 | D | OD1 | −55 | 409 | 722 | 31 |
| 381 | D | OD2 | −58 | 429 | 714 | 43 |
| 382 | A | N | −28 | 420 | 742 | 34 |
| 382 | A | CA | −30 | 421 | 756 | 37 |
| 382 | A | C | −43 | 413 | 760 | 38 |
| 382 | A | O | −42 | 404 | 768 | 40 |
| 382 | A | CB | −31 | 435 | 760 | 35 |
| 383 | S | N | −54 | 417 | 754 | 38 |
| 383 | S | CA | −67 | 411 | 757 | 39 |
| 383 | S | C | −69 | 396 | 753 | 39 |
| 383 | S | O | −80 | 391 | 755 | 44 |
| 383 | S | CB | −78 | 419 | 750 | 36 |
| 383 | S | OG | −77 | 327 | 53 | 40 |
| 384 | G | N | −59 | 389 | 748 | 37 |
| 384 | G | CA | −61 | 375 | 745 | 32 |
| 384 | G | C | −66 | 373 | 731 | 32 |
| 384 | G | O | −66 | 361 | 726 | 34 |
| 385 | K | N | −71 | 383 | 724 | 33 |
| 385 | K | CA | −77 | 382 | 711 | 35 |
| 385 | K | C | −67 | 377 | 701 | 36 |
| 385 | K | O | −55 | 381 | 701 | 36 |
| 385 | K | CB | −83 | 395 | 706 | 34 |
| 385 | K | CG | −88 | 395 | 692 | 38 |
| 385 | K | CD | −95 | 409 | 687 | 37 |
| 385 | K | CE | −85 | 421 | 689 | 38 |
| 385 | K | NZ | −92 | 433 | 685 | 36 |
| 386 | R | N | −71 | 369 | 692 | 37 |
| 386 | R | CA | −62 | 364 | 681 | 39 |
| 386 | R | C | −60 | 375 | 671 | 39 |
| 386 | R | O | −69 | 381 | 666 | 40 |
| 386 | R | CB | −68 | 352 | 674 | 38 |
| 386 | R | CG | −67 | 339 | 682 | 43 |
| 386 | R | CD | −75 | 327 | 676 | 45 |
| 386 | R | NE | −73 | 326 | 661 | 47 |
| 386 | R | CZ | −64 | 318 | 655 | 46 |
| 386 | R | NH1 | −56 | 310 | 663 | 44 |
| 386 | R | NH2 | −63 | 318 | 642 | 46 |
| 387 | V | N | −47 | 377 | 668 | 38 |
| 387 | V | CA | −43 | 388 | 658 | 37 |
| 387 | V | C | −34 | 383 | 647 | 35 |
| 387 | V | O | −25 | 375 | 650 | 36 |
| 387 | V | CB | −38 | 401 | 666 | 36 |
| 387 | V | CG1 | −28 | 397 | 676 | 37 |
| 387 | V | CG2 | −32 | 411 | 656 | 38 |
| 388 | Y | N | −36 | 386 | 635 | 34 |
| 388 | Y | CA | −28 | 382 | 624 | 30 |
| 388 | Y | C | −18 | 393 | 621 | 29 |
| 388 | Y | O | −21 | 405 | 622 | 31 |
| 388 | Y | CB | −36 | 380 | 611 | 29 |
| 388 | Y | CG | −47 | 369 | 612 | 23 |
| 388 | Y | CD1 | −44 | 356 | 611 | 23 |
| 388 | Y | CD2 | −60 | 372 | 617 | 26 |
| 388 | Y | CE1 | −53 | 346 | 613 | 32 |
| 388 | Y | CE2 | −69 | 362 | 619 | 30 |
| 388 | Y | CZ | −66 | 349 | 617 | 32 |
| 388 | Y | OH | −75 | 339 | 620 | 39 |
| 389 | Y | N | −6 | 389 | 617 | 28 |
| 389 | Y | CA | 4 | 398 | 615 | 23 |
| 389 | Y | C | 14 | 392 | 604 | 20 |
| 389 | Y | O | 14 | 380 | 601 | 18 |
| 389 | Y | CB | 12 | 401 | 628 | 20 |
| 389 | Y | CG | 20 | 390 | 633 | 19 |
| 389 | Y | CD1 | 14 | 379 | 640 | 18 |
| 389 | Y | CD2 | 34 | 389 | 631 | 20 |
| 389 | Y | CE1 | 21 | 368 | 644 | 15 |
| 389 | Y | CE2 | 41 | 378 | 635 | 14 |
| 389 | Y | CZ | 34 | 367 | 641 | 14 |
| 389 | Y | OH | 41 | 356 | 644 | 18 |
| 390 | L | N | 22 | 400 | 598 | 22 |
| 390 | L | CA | 32 | 396 | 588 | 20 |
| 390 | L | C | 46 | 392 | 594 | 21 |
| 390 | L | O | 52 | 400 | 601 | 19 |
| 390 | L | CB | 33 | 407 | 578 | 21 |
| 390 | L | CG | 39 | 404 | 564 | 21 |
| 390 | L | CD1 | 29 | 394 | 557 | 20 |
| 390 | L | CD2 | 40 | 416 | 556 | 23 |
| 391 | T | N | 51 | 381 | 589 | 18 |
| 391 | T | CA | 64 | 376 | 594 | 19 |
| 391 | T | C | 71 | 370 | 582 | 21 |
| 391 | T | O | 66 | 371 | 571 | 23 |
| 391 | T | CB | 62 | 366 | 606 | 18 |
| 391 | T | OG1 | 76 | 363 | 610 | 20 |
| 391 | T | CG2 | 55 | 353 | 601 | 15 |
| 392 | R | N | 83 | 365 | 584 | 20 |
| 392 | R | CA | 91 | 358 | 574 | 20 |
| 392 | R | C | 102 | 350 | 581 | 22 |
| 392 | R | O | 105 | 352 | 593 | 24 |
| 392 | R | CB | 98 | 369 | 565 | 21 |
| 392 | R | CG | 107 | 379 | 573 | 18 |
| 392 | R | CD | 117 | 385 | 563 | 18 |
| 392 | R | NE | 126 | 375 | 557 | 19 |
| 392 | R | CZ | 131 | 377 | 545 | 16 |
| 392 | R | NH1 | 130 | 388 | 539 | 20 |
| 392 | R | NH2 | 138 | 367 | 540 | 13 |
| 393 | D | N | 109 | 342 | 574 | 20 |

TABLE 1-continued

| | | | | | |
|---|---|---|---|---|---|
| 393 D | CA | 120 | 334 | 579 | 24 |
| 393 D | C | 131 | 345 | 582 | 25 |
| 393 D | O | 134 | 353 | 574 | 26 |
| 393 D | CB | 125 | 325 | 568 | 25 |
| 393 D | CG | 136 | 315 | 573 | 25 |
| 393 D | OD1 | 147 | 320 | 574 | 28 |
| 393 D | OD2 | 134 | 303 | 574 | 27 |
| 394 P | N | 137 | 344 | 594 | 25 |
| 394 P | CA | 147 | 355 | 597 | 24 |
| 394 P | C | 162 | 353 | 593 | 21 |
| 394 P | O | 170 | 360 | 597 | 19 |
| 394 P | CB | 145 | 356 | 613 | 21 |
| 394 P | CG | 143 | 342 | 617 | 22 |
| 394 P | CD | 135 | 335 | 606 | 21 |
| 395 T | N | 164 | 342 | 585 | 22 |
| 395 T | CA | 178 | 339 | 581 | 20 |
| 395 T | C | 185 | 351 | 574 | 21 |
| 395 T | O | 196 | 354 | 578 | 22 |
| 395 T | CB | 179 | 327 | 572 | 20 |
| 395 T | OG1 | 173 | 315 | 580 | 24 |
| 395 T | CG2 | 193 | 323 | 568 | 19 |
| 396 T | N | 179 | 356 | 563 | 18 |
| 396 T | CA | 185 | 367 | 556 | 20 |
| 396 T | C | 186 | 380 | 565 | 19 |
| 396 T | O | 196 | 386 | 565 | 17 |
| 396 T | CB | 179 | 369 | 542 | 20 |
| 396 T | OG1 | 180 | 358 | 534 | 20 |
| 396 T | CG2 | 186 | 381 | 535 | 16 |
| 397 P | N | 175 | 383 | 572 | 18 |
| 397 P | CA | 176 | 395 | 581 | 17 |
| 397 P | C | 187 | 394 | 591 | 16 |
| 397 P | O | 194 | 404 | 594 | 18 |
| 397 P | CB | 162 | 395 | 587 | 19 |
| 397 P | CG | 153 | 391 | 576 | 14 |
| 397 P | CD | 161 | 379 | 571 | 17 |
| 398 L | N | 189 | 382 | 597 | 18 |
| 398 L | CA | 199 | 380 | 607 | 20 |
| 398 L | C | 213 | 380 | 601 | 20 |
| 398 L | O | 223 | 385 | 607 | 20 |
| 398 L | CB | 196 | 367 | 615 | 20 |
| 398 L | CG | 184 | 368 | 625 | 19 |
| 398 L | CD1 | 182 | 354 | 631 | 19 |
| 398 L | CD2 | 186 | 378 | 635 | 20 |
| 399 A | N | 215 | 373 | 589 | 19 |
| 399 A | CA | 228 | 373 | 583 | 16 |
| 399 A | C | 233 | 387 | 580 | 15 |
| 399 A | O | 244 | 390 | 581 | 14 |
| 399 A | CB | 227 | 365 | 570 | 16 |
| 400 R | N | 223 | 396 | 575 | 15 |
| 400 R | CA | 227 | 410 | 572 | 15 |
| 400 R | C | 229 | 418 | 585 | 16 |
| 400 R | O | 237 | 428 | 584 | 14 |
| 400 R | CB | 215 | 417 | 564 | 14 |
| 400 R | CG | 212 | 408 | 552 | 17 |
| 400 R | CD | 203 | 415 | 541 | 19 |
| 400 R | NE | 205 | 407 | 529 | 22 |
| 400 R | CZ | 199 | 410 | 517 | 22 |
| 400 R | NH1 | 190 | 420 | 516 | 26 |
| 400 R | NH2 | 201 | 402 | 507 | 21 |
| 401 A | N | 222 | 415 | 596 | 19 |
| 401 A | CA | 224 | 422 | 608 | 19 |
| 401 A | C | 239 | 419 | 613 | 18 |
| 401 A | O | 246 | 428 | 618 | 19 |
| 401 A | CB | 215 | 417 | 619 | 17 |
| 402 A | N | 243 | 406 | 611 | 18 |
| 402 A | CA | 257 | 403 | 615 | 18 |
| 402 A | C | 267 | 411 | 607 | 20 |
| 402 A | O | 276 | 417 | 613 | 20 |
| 402 A | CB | 260 | 388 | 612 | 15 |
| 403 W | N | 264 | 413 | 594 | 15 |
| 403 W | CA | 273 | 421 | 586 | 19 |
| 403 W | C | 274 | 435 | 590 | 19 |
| 403 W | O | 284 | 441 | 591 | 17 |
| 403 W | CB | 269 | 420 | 571 | 19 |
| 403 W | CG | 280 | 425 | 561 | 20 |
| 403 W | CD1 | 283 | 438 | 559 | 19 |
| 403 W | CD2 | 289 | 417 | 553 | 19 |
| 403 W | NE1 | 294 | 439 | 550 | 19 |
| 403 W | CE2 | 297 | 426 | 546 | 19 |
| 403 W | CE3 | 290 | 403 | 551 | 19 |
| 403 W | CZ2 | 307 | 421 | 537 | 21 |
| 403 W | CZ3 | 300 | 398 | 543 | 23 |
| 403 W | CH2 | 308 | 407 | 536 | 17 |
| 404 E | N | 262 | 441 | 593 | 20 |
| 404 E | CA | 260 | 455 | 597 | 18 |
| 404 E | C | 265 | 458 | 611 | 17 |
| 404 E | O | 268 | 469 | 615 | 20 |
| 404 E | CB | 246 | 460 | 595 | 19 |
| 404 E | CG | 242 | 461 | 581 | 18 |
| 404 E | CD | 227 | 460 | 578 | 26 |
| 404 E | OE1 | 219 | 459 | 587 | 25 |
| 404 E | OE2 | 223 | 461 | 566 | 23 |
| 405 T | N | 267 | 447 | 619 | 19 |
| 405 T | CA | 273 | 448 | 633 | 22 |
| 405 T | C | 287 | 453 | 632 | 23 |
| 405 T | O | 291 | 462 | 639 | 27 |
| 405 T | CB | 272 | 435 | 640 | 21 |
| 405 T | OG1 | 258 | 432 | 643 | 20 |
| 405 T | CG2 | 279 | 435 | 654 | 17 |
| 406 A | N | 295 | 448 | 622 | 22 |
| 406 A | CA | 309 | 451 | 621 | 23 |
| 406 A | C | 313 | 461 | 609 | 25 |
| 406 A | O | 324 | 465 | 608 | 25 |
| 406 A | CB | 317 | 438 | 619 | 22 |
| 407 R | N | 303 | 464 | 601 | 26 |
| 407 R | CA | 306 | 473 | 589 | 25 |
| 407 R | C | 294 | 483 | 587 | 25 |
| 407 R | O | 283 | 479 | 588 | 30 |
| 407 R | CB | 306 | 465 | 576 | 26 |
| 407 R | CG | 319 | 458 | 573 | 27 |
| 407 R | CD | 329 | 469 | 568 | 32 |
| 407 R | NE | 342 | 463 | 565 | 34 |
| 407 R | CZ | 351 | 458 | 573 | 38 |
| 407 R | NH1 | 349 | 459 | 586 | 36 |
| 407 R | NH2 | 361 | 451 | 568 | 36 |
| 408 H | N | 298 | 495 | 584 | 29 |
| 408 H | CA | 287 | 505 | 582 | 34 |
| 408 H | C | 283 | 503 | 567 | 34 |
| 408 H | O | 292 | 502 | 559 | 37 |
| 408 H | CB | 293 | 519 | 585 | 38 |
| 408 H | CG | 295 | 522 | 599 | 46 |
| 408 H | ND1 | 307 | 527 | 604 | 49 |
| 408 H | CD2 | 287 | 520 | 610 | 48 |
| 408 H | CE1 | 306 | 528 | 617 | 51 |
| 408 H | NE2 | 294 | 524 | 621 | 50 |
| 409 T | N | 270 | 502 | 565 | 33 |
| 409 T | CA | 265 | 501 | 551 | 29 |
| 409 T | C | 257 | 513 | 547 | 26 |
| 409 T | O | 253 | 521 | 555 | 24 |
| 409 T | CB | 257 | 487 | 550 | 25 |
| 409 T | OG1 | 247 | 487 | 560 | 27 |
| 409 T | CG2 | 267 | 475 | 550 | 24 |
| 410 P | N | 255 | 514 | 533 | 29 |
| 410 P | CA | 247 | 525 | 528 | 27 |
| 410 P | C | 232 | 523 | 531 | 25 |
| 410 P | O | 224 | 533 | 532 | 27 |
| 410 P | CB | 250 | 525 | 513 | 28 |
| 410 P | CG | 262 | 517 | 512 | 30 |
| 410 P | CD | 261 | 506 | 522 | 32 |
| 411 V | N | 228 | 511 | 533 | 26 |
| 411 V | CA | 214 | 508 | 536 | 29 |
| 411 V | C | 214 | 498 | 548 | 27 |
| 411 V | O | 220 | 487 | 548 | 30 |
| 411 V | CB | 207 | 501 | 525 | 31 |
| 411 V | CG1 | 192 | 498 | 529 | 28 |
| 411 V | CG2 | 207 | 510 | 512 | 31 |
| 412 N | N | 208 | 503 | 559 | 26 |
| 412 N | CA | 207 | 495 | 572 | 21 |
| 412 N | C | 195 | 487 | 572 | 18 |
| 412 N | O | 184 | 491 | 575 | 22 |
| 412 N | CB | 206 | 505 | 584 | 18 |
| 412 N | CG | 219 | 513 | 585 | 18 |
| 412 N | OD1 | 228 | 509 | 591 | 24 |
| 412 N | ND2 | 219 | 525 | 578 | 21 |
| 413 S | N | 197 | 474 | 568 | 18 |
| 413 S | CA | 186 | 465 | 567 | 22 |
| 413 S | C | 179 | 462 | 581 | 23 |
| 413 S | O | 167 | 459 | 581 | 22 |

TABLE 1-continued

| | | | | | |
|---|---|---|---|---|---|
| 413 S | CB | 189 | 451 | 560 | 20 |
| 413 S | OG | 198 | 443 | 568 | 23 |
| 414 W | N | 187 | 462 | 592 | 21 |
| 414 W | CA | 182 | 459 | 605 | 18 |
| 414 W | C | 171 | 470 | 609 | 18 |
| 414 W | O | 161 | 466 | 615 | 20 |
| 414 W | CB | 193 | 459 | 615 | 16 |
| 414 W | CG | 200 | 473 | 618 | 16 |
| 414 W | CD1 | 212 | 477 | 612 | 15 |
| 414 W | CD2 | 196 | 483 | 627 | 18 |
| 414 W | NE1 | 215 | 490 | 617 | 17 |
| 414 W | CE2 | 205 | 494 | 626 | 19 |
| 414 W | CE3 | 185 | 485 | 635 | 20 |
| 414 W | CZ2 | 204 | 506 | 633 | 17 |
| 414 W | CZ3 | 183 | 497 | 642 | 19 |
| 414 W | CH2 | 193 | 507 | 641 | 21 |
| 415 L | N | 173 | 482 | 605 | 15 |
| 415 L | CA | 163 | 492 | 608 | 18 |
| 415 L | C | 151 | 491 | 599 | 21 |
| 415 L | O | 140 | 493 | 604 | 22 |
| 415 L | CB | 169 | 506 | 606 | 16 |
| 415 L | CG | 161 | 519 | 608 | 18 |
| 415 L | CD1 | 154 | 519 | 621 | 18 |
| 415 L | CD2 | 170 | 531 | 607 | 16 |
| 416 G | N | 153 | 487 | 586 | 21 |
| 416 G | CA | 141 | 485 | 577 | 16 |
| 416 G | C | 133 | 473 | 583 | 18 |
| 416 G | O | 121 | 473 | 583 | 18 |
| 417 N | N | 140 | 463 | 587 | 16 |
| 417 N | CA | 134 | 451 | 592 | 19 |
| 417 N | C | 127 | 453 | 606 | 21 |
| 417 N | O | 116 | 447 | 608 | 21 |
| 417 N | CB | 144 | 440 | 594 | 17 |
| 417 N | CG | 146 | 432 | 580 | 23 |
| 417 N | OD1 | 137 | 432 | 572 | 23 |
| 417 N | ND2 | 158 | 427 | 578 | 20 |
| 418 I | N | 132 | 462 | 614 | 18 |
| 418 I | CA | 125 | 464 | 627 | 21 |
| 418 I | C | 112 | 472 | 623 | 23 |
| 418 I | O | 101 | 468 | 628 | 23 |
| 418 I | CB | 133 | 473 | 636 | 23 |
| 418 I | CG1 | 144 | 465 | 643 | 20 |
| 418 I | CG2 | 125 | 480 | 647 | 22 |
| 418 I | CD1 | 154 | 474 | 652 | 19 |
| 419 I | N | 112 | 481 | 614 | 20 |
| 419 I | CA | 100 | 489 | 610 | 23 |
| 419 I | C | 90 | 480 | 604 | 23 |
| 419 I | O | 78 | 480 | 608 | 23 |
| 419 I | CB | 104 | 501 | 600 | 20 |
| 419 I | CG1 | 112 | 511 | 608 | 17 |
| 419 I | CG2 | 91 | 507 | 595 | 18 |
| 419 I | CD1 | 118 | 522 | 599 | 19 |
| 420 M | N | 94 | 472 | 594 | 21 |
| 420 M | CA | 84 | 464 | 587 | 21 |
| 420 M | C | 79 | 452 | 595 | 21 |
| 420 M | O | 68 | 448 | 593 | 18 |
| 420 M | CB | 91 | 459 | 574 | 22 |
| 420 M | CG | 94 | 471 | 564 | 25 |
| 420 M | SD | 77 | 481 | 559 | 35 |
| 420 M | CE | 70 | 467 | 545 | 28 |
| 421 Y | N | 88 | 446 | 603 | 21 |
| 421 Y | CA | 84 | 434 | 610 | 17 |
| 421 Y | C | 84 | 436 | 626 | 17 |
| 421 Y | O | 86 | 427 | 633 | 19 |
| 421 Y | CB | 94 | 422 | 607 | 16 |
| 421 Y | CG | 93 | 418 | 592 | 19 |
| 421 Y | CD1 | 83 | 410 | 588 | 17 |
| 421 Y | CD2 | 102 | 422 | 583 | 20 |
| 421 Y | CE1 | 82 | 406 | 575 | 24 |
| 421 Y | CE2 | 102 | 419 | 570 | 20 |
| 421 Y | CZ | 91 | 410 | 566 | 26 |
| 421 Y | OH | 90 | 407 | 552 | 24 |
| 422 A | N | 81 | 448 | 630 | 17 |
| 422 A | CA | 80 | 451 | 644 | 20 |
| 422 A | C | 72 | 441 | 653 | 24 |
| 422 A | O | 76 | 438 | 664 | 29 |
| 422 A | CB | 75 | 465 | 646 | 14 |
| 423 P | N | 61 | 436 | 648 | 25 |
| 423 P | CA | 53 | 426 | 656 | 23 |
| 423 P | C | 59 | 412 | 657 | 22 |
| 423 P | O | 54 | 404 | 666 | 22 |
| 423 P | CB | 39 | 426 | 648 | 24 |
| 423 P | CG | 38 | 439 | 642 | 23 |
| 423 P | CD | 52 | 441 | 636 | 21 |
| 424 T | N | 69 | 409 | 649 | 20 |
| 424 T | CA | 75 | 396 | 650 | 20 |
| 424 T | C | 83 | 392 | 662 | 21 |
| 424 T | O | 89 | 401 | 668 | 23 |
| 424 T | CB | 83 | 392 | 637 | 22 |
| 424 T | OG1 | 95 | 401 | 637 | 22 |
| 424 T | CG2 | 75 | 394 | 624 | 16 |
| 425 L | N | 83 | 380 | 665 | 21 |
| 425 L | CA | 91 | 374 | 677 | 22 |
| 425 L | C | 106 | 377 | 675 | 22 |
| 425 L | O | 112 | 384 | 684 | 18 |
| 425 L | CB | 88 | 359 | 677 | 22 |
| 425 L | CG | 93 | 349 | 687 | 30 |
| 425 L | CD1 | 87 | 352 | 701 | 31 |
| 425 L | CD2 | 88 | 335 | 683 | 28 |
| 426 W | N | 111 | 375 | 663 | 22 |
| 426 W | CA | 125 | 377 | 660 | 19 |
| 426 W | C | 130 | 391 | 659 | 20 |
| 426 W | O | 141 | 395 | 664 | 20 |
| 426 W | CB | 129 | 368 | 647 | 22 |
| 426 W | CG | 120 | 372 | 635 | 25 |
| 426 W | CD1 | 108 | 366 | 631 | 25 |
| 426 W | CD2 | 123 | 382 | 625 | 23 |
| 426 W | NE1 | 103 | 372 | 620 | 20 |
| 426 W | CE2 | 112 | 382 | 616 | 24 |
| 426 W | CE3 | 133 | 392 | 624 | 19 |
| 426 W | CZ2 | 111 | 391 | 605 | 21 |
| 426 W | CZ3 | 133 | 400 | 613 | 19 |
| 426 W | CH2 | 122 | 400 | 604 | 24 |
| 427 A | N | 122 | 400 | 654 | 16 |
| 427 A | CA | 126 | 414 | 653 | 16 |
| 427 A | C | 125 | 421 | 667 | 18 |
| 427 A | O | 133 | 430 | 669 | 18 |
| 427 A | CB | 117 | 422 | 643 | 19 |
| 428 R | N | 116 | 417 | 675 | 19 |
| 428 R | CA | 115 | 422 | 689 | 19 |
| 428 R | C | 126 | 418 | 698 | 15 |
| 428 R | O | 133 | 426 | 704 | 17 |
| 428 R | CB | 101 | 419 | 694 | 13 |
| 428 R | CG | 90 | 427 | 688 | 17 |
| 428 R | CD | 76 | 422 | 692 | 21 |
| 428 R | NE | 71 | 428 | 704 | 24 |
| 428 R | CZ | 63 | 423 | 713 | 26 |
| 428 R | NH1 | 58 | 411 | 710 | 20 |
| 428 R | NH2 | 59 | 429 | 724 | 20 |
| 429 M | N | 128 | 405 | 699 | 18 |
| 429 M | CA | 138 | 399 | 708 | 20 |
| 429 M | C | 152 | 400 | 704 | 20 |
| 429 M | O | 161 | 401 | 712 | 23 |
| 429 M | CB | 134 | 385 | 711 | 17 |
| 429 M | CG | 120 | 383 | 717 | 23 |
| 429 M | SD | 115 | 365 | 723 | 29 |
| 429 M | CE | 99 | 369 | 734 | 39 |
| 430 I | N | 155 | 398 | 691 | 19 |
| 430 I | CA | 169 | 399 | 686 | 18 |
| 430 I | C | 173 | 412 | 680 | 18 |
| 430 I | O | 182 | 419 | 685 | 16 |
| 430 I | CB | 172 | 387 | 677 | 18 |
| 430 I | CG1 | 168 | 374 | 684 | 17 |
| 430 I | CG2 | 187 | 387 | 673 | 15 |
| 430 I | CD1 | 169 | 362 | 675 | 20 |
| 431 L | N | 167 | 416 | 669 | 18 |
| 431 L | CA | 170 | 429 | 663 | 16 |
| 431 L | C | 170 | 441 | 672 | 18 |
| 431 L | O | 181 | 448 | 673 | 16 |
| 431 L | CB | 162 | 431 | 650 | 16 |
| 431 L | CG | 164 | 422 | 638 | 17 |
| 431 L | CD1 | 156 | 427 | 626 | 12 |
| 431 L | CD2 | 179 | 420 | 635 | 16 |
| 432 M | N | 159 | 444 | 678 | 16 |
| 432 M | CA | 158 | 455 | 687 | 17 |
| 432 M | C | 168 | 455 | 699 | 14 |
| 432 M | O | 174 | 465 | 702 | 17 |
| 432 M | CB | 144 | 457 | 692 | 19 |

TABLE 1-continued

| | | | | | |
|---|---|---|---|---|---|
| 432 M | CG | 133 | 459 | 682 | 24 |
| 432 M | SD | 115 | 462 | 690 | 25 |
| 432 M | CE | 116 | 451 | 707 | 40 |
| 433 T | N | 168 | 443 | 705 | 16 |
| 433 T | CA | 178 | 442 | 717 | 16 |
| 433 T | C | 192 | 444 | 712 | 17 |
| 433 T | O | 199 | 453 | 718 | 19 |
| 433 T | CB | 176 | 428 | 722 | 19 |
| 433 T | OG1 | 162 | 425 | 725 | 22 |
| 433 T | CG2 | 184 | 426 | 735 | 17 |
| 434 H | N | 197 | 437 | 702 | 16 |
| 434 H | CA | 210 | 438 | 698 | 18 |
| 434 H | C | 214 | 453 | 694 | 17 |
| 434 H | O | 223 | 459 | 699 | 18 |
| 434 H | CB | 213 | 429 | 686 | 20 |
| 434 H | CG | 227 | 429 | 680 | 24 |
| 434 H | ND1 | 237 | 423 | 687 | 24 |
| 434 H | CD2 | 232 | 433 | 669 | 20 |
| 434 H | CE1 | 248 | 424 | 680 | 26 |
| 434 H | NE2 | 245 | 430 | 668 | 22 |
| 435 F | N | 207 | 458 | 684 | 19 |
| 435 F | CA | 211 | 471 | 679 | 14 |
| 435 F | C | 208 | 483 | 689 | 17 |
| 435 F | O | 216 | 492 | 688 | 14 |
| 435 F | CB | 204 | 474 | 665 | 16 |
| 435 F | CG | 210 | 466 | 654 | 16 |
| 435 F | CD1 | 223 | 469 | 649 | 14 |
| 435 F | CD2 | 204 | 454 | 649 | 15 |
| 435 F | CE1 | 229 | 461 | 640 | 16 |
| 435 F | CE2 | 210 | 446 | 640 | 15 |
| 435 F | CZ | 223 | 449 | 635 | 12 |
| 436 F | N | 198 | 482 | 697 | 19 |
| 436 F | CA | 196 | 493 | 707 | 18 |
| 436 F | C | 208 | 492 | 717 | 16 |
| 436 F | O | 212 | 502 | 722 | 17 |
| 436 F | CB | 182 | 493 | 713 | 16 |
| 436 F | CG | 173 | 502 | 706 | 15 |
| 436 F | CD1 | 165 | 497 | 696 | 16 |
| 436 F | CD2 | 171 | 515 | 710 | 15 |
| 436 F | CE1 | 156 | 506 | 689 | 11 |
| 436 F | CE2 | 163 | 524 | 704 | 16 |
| 436 F | CZ | 155 | 519 | 693 | 10 |
| 437 S | N | 214 | 480 | 719 | 18 |
| 437 S | CA | 225 | 478 | 728 | 21 |
| 437 S | C | 237 | 486 | 722 | 20 |
| 437 S | O | 243 | 495 | 729 | 20 |
| 437 S | CB | 229 | 464 | 729 | 17 |
| 437 S | OG | 239 | 461 | 739 | 22 |
| 438 I | N | 240 | 484 | 709 | 23 |
| 438 I | CA | 251 | 491 | 702 | 23 |
| 438 I | C | 249 | 506 | 701 | 23 |
| 438 I | O | 258 | 514 | 703 | 27 |
| 438 I | CB | 253 | 486 | 688 | 22 |
| 438 I | CG1 | 257 | 471 | 687 | 19 |
| 438 I | CG2 | 264 | 494 | 681 | 29 |
| 438 I | CD1 | 255 | 465 | 674 | 17 |
| 439 L | N | 237 | 510 | 698 | 23 |
| 439 L | CA | 234 | 525 | 697 | 24 |
| 439 L | C | 236 | 532 | 710 | 24 |
| 439 L | O | 240 | 544 | 710 | 23 |
| 439 L | CB | 220 | 527 | 692 | 28 |
| 439 L | CG | 215 | 522 | 679 | 31 |
| 439 L | CD1 | 200 | 524 | 677 | 27 |
| 439 L | CD2 | 223 | 529 | 667 | 25 |
| 440 L | N | 233 | 526 | 722 | 23 |
| 440 L | CA | 234 | 531 | 735 | 23 |
| 440 L | C | 249 | 534 | 738 | 21 |
| 440 L | O | 252 | 545 | 742 | 21 |
| 440 L | CB | 229 | 521 | 745 | 23 |
| 440 L | CG | 214 | 522 | 750 | 20 |
| 440 L | CD1 | 210 | 510 | 756 | 23 |
| 440 L | CD2 | 213 | 534 | 758 | 21 |
| 441 A | N | 257 | 524 | 736 | 23 |
| 441 A | CA | 271 | 524 | 739 | 25 |
| 441 A | C | 279 | 535 | 731 | 27 |
| 441 A | O | 288 | 541 | 737 | 31 |
| 441 A | CB | 278 | 510 | 735 | 23 |
| 442 Q | N | 274 | 538 | 719 | 26 |
| 442 Q | CA | 280 | 549 | 711 | 27 |
| 442 Q | C | 273 | 562 | 712 | 30 |
| 442 Q | O | 277 | 572 | 705 | 30 |
| 442 Q | CB | 281 | 544 | 696 | 27 |
| 442 Q | CG | 286 | 530 | 694 | 22 |
| 442 Q | CD | 300 | 529 | 700 | 26 |
| 442 Q | OE1 | 308 | 539 | 701 | 28 |
| 442 Q | NE2 | 304 | 517 | 703 | 23 |
| 443 E | N | 262 | 562 | 720 | 35 |
| 443 E | CA | 254 | 574 | 721 | 37 |
| 443 E | C | 249 | 579 | 708 | 35 |
| 443 E | O | 250 | 591 | 705 | 35 |
| 443 E | CB | 261 | 585 | 729 | 42 |
| 443 E | CG | 259 | 583 | 745 | 52 |
| 443 E | CD | 269 | 591 | 753 | 58 |
| 443 E | OE1 | 269 | 604 | 751 | 62 |
| 443 E | OE2 | 276 | 586 | 762 | 60 |
| 444 Q | N | 244 | 570 | 699 | 33 |
| 444 Q | CA | 239 | 573 | 686 | 33 |
| 444 Q | C | 224 | 570 | 684 | 35 |
| 444 Q | O | 220 | 567 | 672 | 38 |
| 444 Q | CB | 248 | 566 | 676 | 35 |
| 444 Q | CG | 262 | 573 | 674 | 33 |
| 444 Q | CD | 271 | 565 | 665 | 38 |
| 444 Q | OE1 | 268 | 553 | 661 | 35 |
| 444 Q | NE2 | 283 | 570 | 663 | 34 |
| 445 L | N | 216 | 571 | 694 | 31 |
| 445 L | CA | 202 | 569 | 693 | 31 |
| 445 L | C | 195 | 580 | 684 | 30 |
| 445 L | O | 185 | 577 | 678 | 31 |
| 445 L | CB | 196 | 569 | 706 | 32 |
| 445 L | CG | 189 | 556 | 711 | 33 |
| 445 L | CD1 | 197 | 543 | 708 | 28 |
| 445 L | CD2 | 187 | 557 | 726 | 36 |
| 446 E | N | 201 | 592 | 684 | 28 |
| 446 E | CA | 195 | 603 | 676 | 31 |
| 446 E | C | 202 | 605 | 663 | 29 |
| 446 E | O | 199 | 615 | 656 | 28 |
| 446 E | CB | 195 | 616 | 684 | 39 |
| 446 E | CG | 203 | 615 | 698 | 51 |
| 446 E | CD | 218 | 616 | 696 | 56 |
| 446 E | OE1 | 224 | 606 | 692 | 53 |
| 446 E | OE2 | 224 | 626 | 700 | 60 |
| 447 K | N | 210 | 596 | 659 | 28 |
| 447 K | CA | 217 | 597 | 646 | 29 |
| 447 K | C | 208 | 591 | 635 | 26 |
| 447 K | O | 205 | 579 | 635 | 25 |
| 447 K | CB | 230 | 589 | 647 | 28 |
| 447 K | CG | 240 | 592 | 635 | 32 |
| 447 K | CD | 250 | 581 | 635 | 34 |
| 447 K | CE | 259 | 583 | 623 | 36 |
| 447 K | NZ | 268 | 571 | 622 | 42 |
| 448 A | N | 204 | 599 | 625 | 24 |
| 448 A | CA | 195 | 594 | 614 | 24 |
| 448 A | C | 203 | 584 | 606 | 23 |
| 448 A | O | 215 | 586 | 603 | 25 |
| 448 A | CB | 191 | 606 | 606 | 22 |
| 449 L | N | 197 | 573 | 603 | 24 |
| 449 L | CA | 203 | 562 | 595 | 26 |
| 449 L | C | 194 | 560 | 583 | 27 |
| 449 L | O | 182 | 561 | 583 | 28 |
| 449 L | CB | 204 | 549 | 603 | 24 |
| 449 L | CG | 214 | 548 | 614 | 21 |
| 449 L | CD1 | 213 | 534 | 620 | 17 |
| 449 L | CD2 | 228 | 550 | 609 | 21 |
| 450 D | N | 201 | 556 | 571 | 26 |
| 450 D | CA | 193 | 553 | 559 | 25 |
| 450 D | C | 189 | 539 | 559 | 23 |
| 450 D | O | 196 | 530 | 561 | 22 |
| 450 D | CB | 202 | 556 | 546 | 29 |
| 450 D | CG | 205 | 570 | 544 | 30 |
| 450 D | OD1 | 196 | 579 | 547 | 32 |
| 450 D | OD2 | 216 | 573 | 539 | 34 |
| 451 C | N | 176 | 537 | 555 | 23 |
| 451 C | CA | 170 | 524 | 554 | 24 |
| 451 C | C | 161 | 524 | 542 | 22 |
| 451 C | O | 159 | 535 | 536 | 21 |
| 451 C | CB | 162 | 520 | 566 | 28 |
| 451 C | SG | 149 | 531 | 571 | 30 |
| 452 Q | N | 156 | 513 | 538 | 22 |

TABLE 1-continued

| | | | | | |
|---|---|---|---|---|---|
| 452 | Q | CA | 147 | 513 | 526 | 24 |
| 452 | Q | C | 133 | 506 | 529 | 22 |
| 452 | Q | O | 133 | 496 | 536 | 20 |
| 452 | Q | CB | 154 | 506 | 514 | 22 |
| 452 | Q | CG | 165 | 515 | 509 | 30 |
| 452 | Q | CD | 170 | 511 | 496 | 36 |
| 452 | Q | OE1 | 169 | 499 | 492 | 35 |
| 452 | Q | NE2 | 176 | 521 | 488 | 34 |
| 453 | I | N | 123 | 512 | 524 | 22 |
| 453 | I | CA | 109 | 506 | 525 | 21 |
| 453 | I | C | 103 | 506 | 511 | 19 |
| 453 | I | O | 101 | 517 | 505 | 19 |
| 453 | I | CB | 101 | 516 | 534 | 21 |
| 453 | I | CG1 | 107 | 515 | 549 | 20 |
| 453 | I | CG2 | 86 | 512 | 534 | 22 |
| 453 | I | CD1 | 103 | 527 | 557 | 22 |
| 454 | Y | N | 100 | 494 | 506 | 22 |
| 454 | Y | CA | 95 | 492 | 492 | 25 |
| 454 | Y | C | 103 | 499 | 482 | 26 |
| 454 | Y | O | 99 | 505 | 472 | 24 |
| 454 | Y | CB | 80 | 497 | 491 | 24 |
| 454 | Y | CG | 69 | 489 | 498 | 21 |
| 454 | Y | CD1 | 72 | 476 | 502 | 20 |
| 454 | Y | CD2 | 57 | 494 | 501 | 22 |
| 454 | Y | CE1 | 62 | 468 | 509 | 28 |
| 454 | Y | CE2 | 47 | 487 | 508 | 23 |
| 454 | Y | CZ | 50 | 474 | 512 | 27 |
| 454 | Y | OH | 40 | 467 | 519 | 25 |
| 455 | G | N | 117 | 497 | 484 | 26 |
| 455 | G | CA | 126 | 503 | 474 | 20 |
| 455 | G | C | 130 | 517 | 476 | 18 |
| 455 | G | O | 140 | 522 | 470 | 24 |
| 456 | A | N | 122 | 525 | 483 | 19 |
| 456 | A | CA | 125 | 539 | 485 | 18 |
| 456 | A | C | 134 | 541 | 497 | 20 |
| 456 | A | O | 133 | 534 | 507 | 16 |
| 456 | A | CB | 112 | 548 | 486 | 17 |
| 457 | C | N | 143 | 551 | 497 | 19 |
| 457 | C | CA | 152 | 554 | 507 | 23 |
| 457 | C | C | 147 | 564 | 517 | 20 |
| 457 | C | O | 143 | 576 | 513 | 20 |
| 457 | C | CB | 166 | 557 | 502 | 26 |
| 457 | C | SG | 178 | 560 | 516 | 39 |
| 458 | Y | N | 148 | 561 | 530 | 22 |
| 458 | Y | CA | 144 | 570 | 541 | 19 |
| 458 | Y | C | 155 | 571 | 551 | 20 |
| 458 | Y | O | 162 | 562 | 554 | 21 |
| 458 | Y | CB | 131 | 564 | 548 | 20 |
| 458 | Y | CG | 119 | 563 | 539 | 20 |
| 458 | Y | CD1 | 117 | 552 | 532 | 21 |
| 458 | Y | CD2 | 110 | 574 | 539 | 20 |
| 458 | Y | CE1 | 105 | 550 | 524 | 24 |
| 458 | Y | CE2 | 99 | 573 | 531 | 25 |
| 458 | Y | CZ | 96 | 561 | 523 | 27 |
| 458 | Y | OH | 85 | 560 | 515 | 34 |
| 459 | S | N | 156 | 583 | 556 | 20 |
| 459 | S | CA | 166 | 586 | 567 | 22 |
| 459 | S | C | 157 | 587 | 579 | 23 |
| 459 | S | O | 149 | 595 | 580 | 24 |
| 459 | S | CB | 173 | 600 | 564 | 20 |
| 459 | S | OG | 182 | 603 | 574 | 30 |
| 460 | I | N | 160 | 578 | 589 | 21 |
| 460 | I | CA | 152 | 577 | 601 | 23 |
| 460 | I | C | 161 | 576 | 614 | 24 |
| 460 | I | O | 171 | 569 | 614 | 24 |
| 460 | I | CB | 143 | 564 | 600 | 21 |
| 460 | I | CG1 | 132 | 567 | 590 | 19 |
| 460 | I | CG2 | 137 | 561 | 614 | 18 |
| 460 | I | CD1 | 124 | 555 | 586 | 16 |
| 461 | E | N | 157 | 584 | 624 | 24 |
| 461 | E | CA | 163 | 584 | 637 | 26 |
| 461 | E | C | 158 | 572 | 645 | 25 |
| 461 | E | O | 146 | 571 | 647 | 23 |
| 461 | E | CB | 161 | 596 | 645 | 27 |
| 461 | E | CG | 164 | 609 | 638 | 32 |
| 461 | E | CD | 166 | 621 | 648 | 35 |
| 461 | E | OE1 | 162 | 620 | 660 | 38 |
| 461 | E | OE2 | 173 | 631 | 644 | 39 |
| 462 | P | N | 167 | 563 | 651 | 24 |
| 462 | P | CA | 162 | 552 | 659 | 24 |
| 462 | P | C | 153 | 555 | 671 | 25 |
| 462 | P | O | 144 | 547 | 674 | 22 |
| 462 | P | CB | 175 | 545 | 663 | 20 |
| 462 | P | CG | 184 | 547 | 651 | 17 |
| 462 | P | CD | 181 | 562 | 648 | 19 |
| 463 | L | N | 154 | 567 | 676 | 25 |
| 463 | L | CA | 146 | 572 | 687 | 28 |
| 463 | L | C | 131 | 573 | 683 | 30 |
| 463 | L | O | 122 | 573 | 692 | 30 |
| 463 | L | CB | 151 | 585 | 693 | 27 |
| 463 | L | CG | 163 | 586 | 702 | 31 |
| 463 | L | CD1 | 166 | 600 | 707 | 31 |
| 463 | L | CD2 | 162 | 577 | 714 | 27 |
| 464 | D | N | 129 | 574 | 670 | 30 |
| 464 | D | CA | 115 | 576 | 665 | 26 |
| 464 | D | C | 107 | 563 | 663 | 25 |
| 464 | D | O | 95 | 563 | 660 | 24 |
| 464 | D | CB | 115 | 583 | 652 | 27 |
| 464 | D | CG | 117 | 598 | 653 | 27 |
| 464 | D | OD1 | 111 | 604 | 662 | 29 |
| 464 | D | OD2 | 125 | 604 | 645 | 35 |
| 465 | L | N | 114 | 551 | 665 | 21 |
| 465 | L | CA | 108 | 538 | 663 | 21 |
| 465 | L | C | 95 | 536 | 670 | 24 |
| 465 | L | O | 86 | 530 | 665 | 25 |
| 465 | L | CB | 118 | 527 | 665 | 20 |
| 465 | L | CG | 129 | 525 | 654 | 25 |
| 465 | L | CD1 | 140 | 516 | 659 | 18 |
| 465 | L | CD2 | 122 | 520 | 642 | 22 |
| 466 | P | N | 94 | 540 | 683 | 26 |
| 466 | P | CA | 81 | 538 | 691 | 25 |
| 466 | P | C | 69 | 544 | 683 | 23 |
| 466 | P | O | 59 | 537 | 681 | 23 |
| 466 | P | CB | 84 | 545 | 704 | 24 |
| 466 | P | CG | 98 | 543 | 706 | 25 |
| 466 | P | CD | 104 | 546 | 692 | 26 |
| 467 | Q | N | 70 | 556 | 679 | 22 |
| 467 | Q | CA | 60 | 563 | 672 | 26 |
| 467 | Q | C | 57 | 557 | 658 | 29 |
| 467 | Q | O | 46 | 554 | 654 | 29 |
| 467 | Q | CB | 63 | 578 | 670 | 26 |
| 467 | Q | CG | 64 | 585 | 683 | 39 |
| 467 | Q | CD | 79 | 590 | 685 | 45 |
| 467 | Q | OE1 | 81 | 602 | 682 | 51 |
| 467 | Q | NE2 | 88 | 581 | 689 | 44 |
| 468 | I | N | 68 | 554 | 650 | 27 |
| 468 | I | CA | 67 | 548 | 637 | 25 |
| 468 | I | C | 59 | 535 | 638 | 26 |
| 468 | I | O | 50 | 532 | 630 | 29 |
| 468 | I | CB | 81 | 546 | 630 | 22 |
| 468 | I | CG1 | 88 | 559 | 628 | 21 |
| 468 | I | CG2 | 79 | 539 | 617 | 18 |
| 468 | I | CD1 | 102 | 558 | 624 | 20 |
| 469 | I | N | 63 | 527 | 648 | 23 |
| 469 | I | CA | 57 | 514 | 650 | 21 |
| 469 | I | C | 42 | 515 | 653 | 23 |
| 469 | I | O | 34 | 508 | 648 | 22 |
| 469 | I | CB | 64 | 505 | 660 | 22 |
| 469 | I | CG1 | 78 | 502 | 655 | 20 |
| 469 | I | CG2 | 57 | 492 | 662 | 21 |
| 469 | I | CD1 | 87 | 494 | 664 | 18 |
| 470 | E | N | 38 | 524 | 662 | 25 |
| 470 | E | CA | 25 | 526 | 666 | 28 |
| 470 | E | C | 16 | 530 | 654 | 26 |
| 470 | E | O | 5 | 525 | 652 | 28 |
| 470 | E | CB | 23 | 537 | 677 | 29 |
| 470 | E | CG | 9 | 538 | 683 | 31 |
| 470 | E | CD | 6 | 551 | 691 | 32 |
| 470 | E | OE1 | 15 | 556 | 698 | 28 |
| 470 | E | OE2 | −5 | 555 | 691 | 31 |
| 471 | R | N | 21 | 540 | 647 | 27 |
| 471 | R | CA | 14 | 545 | 635 | 27 |
| 471 | R | C | 11 | 534 | 624 | 28 |
| 471 | R | O | 1 | 535 | 617 | 30 |
| 471 | R | CB | 21 | 557 | 629 | 25 |
| 471 | R | CG | 21 | 570 | 637 | 30 |
| 471 | R | CD | 8 | 577 | 635 | 32 |
| 471 | R | NE | 4 | 579 | 621 | 33 |

TABLE 1-continued

| | | | | | |
|---|---|---|---|---|---|
| 471 R | CZ | 7 | 589 | 614 | 34 |
| 471 R | NH1 | 14 | 600 | 619 | 32 |
| 471 R | NH2 | 4 | 590 | 601 | 36 |
| 472 L | N | 21 | 525 | 622 | 28 |
| 472 L | CA | 19 | 515 | 612 | 26 |
| 472 L | C | 13 | 501 | 617 | 27 |
| 472 L | O | 7 | 494 | 609 | 28 |
| 472 L | CB | 33 | 510 | 607 | 25 |
| 472 L | CG | 44 | 520 | 603 | 26 |
| 472 L | CD1 | 54 | 512 | 595 | 25 |
| 472 L | CD2 | 39 | 532 | 595 | 26 |
| 473 H | N | 16 | 498 | 629 | 27 |
| 473 H | CA | 11 | 485 | 635 | 25 |
| 473 H | C | 2 | 486 | 646 | 25 |
| 473 H | O | −4 | 477 | 650 | 24 |
| 473 H | CB | 23 | 476 | 639 | 23 |
| 473 H | CG | 33 | 474 | 628 | 22 |
| 473 H | ND1 | 32 | 464 | 619 | 21 |
| 473 H | CD2 | 45 | 480 | 626 | 21 |
| 473 H | CE1 | 43 | 464 | 611 | 20 |
| 473 H | NE2 | 51 | 474 | 615 | 19 |
| 474 G | N | 1 | 498 | 652 | 25 |
| 474 G | CA | −7 | 501 | 663 | 29 |
| 474 G | C | 0 | 497 | 676 | 32 |
| 474 G | O | 10 | 491 | 676 | 32 |
| 475 L | N | −7 | 499 | 687 | 32 |
| 475 L | CA | −1 | 496 | 700 | 27 |
| 475 L | C | 0 | 481 | 703 | 25 |
| 475 L | O | 9 | 477 | 711 | 26 |
| 475 L | CB | −9 | 502 | 712 | 26 |
| 475 L | CG | −8 | 517 | 713 | 25 |
| 475 L | CD1 | −18 | 522 | 723 | 28 |
| 475 L | CD2 | 6 | 520 | 717 | 27 |
| 476 S | N | −7 | 472 | 696 | 24 |
| 476 S | CA | −6 | 458 | 698 | 25 |
| 476 S | C | 7 | 452 | 694 | 28 |
| 476 S | O | 11 | 442 | 699 | 29 |
| 476 S | CB | −17 | 450 | 690 | 25 |
| 476 S | OG | −15 | 453 | 676 | 30 |
| 477 A | N | 14 | 460 | 686 | 28 |
| 477 A | CA | 28 | 456 | 682 | 26 |
| 477 A | C | 37 | 455 | 694 | 25 |
| 477 A | O | 47 | 447 | 694 | 28 |
| 477 A | CB | 33 | 465 | 672 | 24 |
| 478 F | N | 34 | 463 | 705 | 23 |
| 478 F | CA | 42 | 463 | 717 | 25 |
| 478 F | C | 37 | 452 | 727 | 27 |
| 478 F | O | 43 | 450 | 737 | 30 |
| 478 F | CB | 41 | 476 | 723 | 20 |
| 478 F | CG | 45 | 488 | 714 | 23 |
| 478 F | CD1 | 57 | 486 | 706 | 20 |
| 478 F | CD2 | 38 | 499 | 713 | 19 |
| 478 F | CE1 | 61 | 496 | 698 | 15 |
| 478 F | CE2 | 42 | 510 | 705 | 19 |
| 478 F | CZ | 54 | 508 | 697 | 14 |
| 479 S | N | 26 | 445 | 724 | 28 |
| 479 S | CA | 20 | 435 | 733 | 28 |
| 479 S | C | 17 | 421 | 729 | 26 |
| 479 S | O | 11 | 413 | 736 | 25 |
| 479 S | CB | 7 | 441 | 740 | 29 |
| 479 S | OG | 3 | 453 | 734 | 35 |
| 480 L | N | 21 | 418 | 717 | 26 |
| 480 L | CA | 18 | 405 | 712 | 26 |
| 480 L | C | 25 | 394 | 719 | 26 |
| 480 L | O | 36 | 395 | 724 | 28 |
| 480 L | CB | 20 | 403 | 697 | 27 |
| 480 L | CG | 13 | 413 | 688 | 28 |
| 480 L | CD1 | 16 | 410 | 673 | 26 |
| 480 L | CD2 | −1 | 412 | 690 | 28 |
| 481 H | N | 18 | 382 | 721 | 24 |
| 481 H | CA | 23 | 371 | 728 | 27 |
| 481 H | C | 17 | 358 | 723 | 27 |
| 481 H | O | 8 | 359 | 714 | 27 |
| 481 H | CB | 21 | 372 | 743 | 27 |
| 481 H | CG | 7 | 372 | 747 | 26 |
| 481 H | ND1 | 0 | 361 | 751 | 25 |
| 481 H | CD2 | −1 | 383 | 749 | 27 |
| 481 H | CE1 | −12 | 364 | 754 | 21 |
| 481 H | NE2 | −13 | 377 | 753 | 22 |
| 482 S | N | 21 | 347 | 728 | 30 |
| 482 S | CA | 15 | 334 | 724 | 31 |
| 482 S | C | 16 | 333 | 709 | 33 |
| 482 S | O | 5 | 333 | 702 | 33 |
| 482 S | CB | 1 | 332 | 730 | 33 |
| 482 S | OG | 1 | 331 | 744 | 34 |
| 483 Y | N | 28 | 332 | 704 | 31 |
| 483 Y | CA | 30 | 331 | 690 | 26 |
| 483 Y | C | 28 | 316 | 686 | 27 |
| 483 Y | O | 29 | 308 | 695 | 28 |
| 483 Y | CB | 45 | 335 | 687 | 24 |
| 483 Y | CG | 47 | 350 | 687 | 20 |
| 483 Y | CD1 | 45 | 358 | 676 | 18 |
| 483 Y | CD2 | 52 | 356 | 699 | 16 |
| 483 Y | CE1 | 47 | 371 | 676 | 15 |
| 483 Y | CE2 | 54 | 370 | 699 | 16 |
| 483 Y | CZ | 51 | 377 | 688 | 15 |
| 483 Y | OH | 54 | 390 | 688 | 16 |
| 484 S | N | 25 | 314 | 674 | 26 |
| 484 S | CA | 22 | 300 | 669 | 28 |
| 484 S | C | 34 | 291 | 670 | 29 |
| 484 S | O | 45 | 296 | 668 | 32 |
| 484 S | CB | 16 | 300 | 655 | 29 |
| 484 S | OG | 26 | 302 | 645 | 28 |
| 485 P | N | 33 | 278 | 673 | 29 |
| 485 P | CA | 43 | 268 | 674 | 29 |
| 485 P | C | 52 | 268 | 661 | 29 |
| 485 P | O | 64 | 267 | 662 | 28 |
| 485 P | CB | 36 | 255 | 676 | 28 |
| 485 P | CG | 24 | 259 | 684 | 32 |
| 485 P | CD | 20 | 272 | 677 | 31 |
| 486 G | N | 45 | 270 | 650 | 29 |
| 486 G | CA | 52 | 270 | 637 | 26 |
| 486 G | C | 61 | 281 | 636 | 25 |
| 486 G | O | 73 | 279 | 632 | 28 |
| 487 E | N | 57 | 293 | 640 | 22 |
| 487 E | CA | 66 | 305 | 640 | 23 |
| 487 E | C | 78 | 303 | 650 | 26 |
| 487 E | O | 89 | 305 | 646 | 25 |
| 487 E | CB | 57 | 317 | 644 | 20 |
| 487 E | CG | 64 | 331 | 643 | 25 |
| 487 E | CD | 72 | 334 | 629 | 23 |
| 487 E | OE1 | 70 | 326 | 619 | 23 |
| 487 E | OE2 | 79 | 343 | 628 | 22 |
| 488 I | N | 75 | 299 | 662 | 26 |
| 488 I | CA | 85 | 297 | 672 | 25 |
| 488 I | C | 95 | 287 | 667 | 26 |
| 488 I | O | 108 | 289 | 668 | 25 |
| 488 I | CB | 79 | 292 | 686 | 25 |
| 488 I | CG1 | 70 | 303 | 691 | 26 |
| 488 I | CG2 | 90 | 289 | 696 | 26 |
| 488 I | CD1 | 62 | 299 | 703 | 26 |
| 489 N | N | 91 | 276 | 662 | 26 |
| 489 N | CA | 100 | 265 | 657 | 29 |
| 489 N | C | 109 | 270 | 645 | 31 |
| 489 N | O | 120 | 265 | 644 | 33 |
| 489 N | CB | 92 | 253 | 653 | 34 |
| 489 N | CG | 88 | 245 | 666 | 40 |
| 489 N | OD1 | 95 | 243 | 675 | 43 |
| 489 N | ND2 | 75 | 240 | 665 | 42 |
| 490 R | N | 104 | 279 | 637 | 30 |
| 490 R | CA | 111 | 284 | 626 | 28 |
| 490 R | C | 122 | 293 | 631 | 26 |
| 490 R | O | 134 | 292 | 626 | 23 |
| 490 R | CB | 103 | 291 | 615 | 24 |
| 490 R | CG | 111 | 297 | 603 | 25 |
| 490 R | CD | 103 | 301 | 591 | 20 |
| 490 R | NE | 94 | 312 | 595 | 22 |
| 490 R | CZ | 85 | 317 | 586 | 21 |
| 490 R | NH1 | 83 | 312 | 574 | 26 |
| 490 R | NH2 | 76 | 327 | 590 | 19 |
| 491 V | N | 119 | 302 | 640 | 26 |
| 491 V | CA | 129 | 312 | 645 | 25 |
| 491 V | C | 139 | 303 | 653 | 25 |
| 491 V | O | 151 | 304 | 649 | 24 |
| 491 V | CB | 122 | 322 | 655 | 25 |
| 491 V | CG1 | 133 | 331 | 661 | 25 |
| 491 V | CG2 | 112 | 331 | 647 | 23 |
| 492 A | N | 135 | 294 | 661 | 25 |

TABLE 1-continued

| | | | | | | |
|---|---|---|---|---|---|---|
| 492 | A | CA | 144 | 286 | 669 | 26 |
| 492 | A | C | 154 | 278 | 660 | 28 |
| 492 | A | O | 166 | 277 | 664 | 25 |
| 492 | A | CB | 137 | 276 | 678 | 26 |
| 493 | S | N | 149 | 272 | 649 | 28 |
| 493 | S | CA | 158 | 264 | 640 | 28 |
| 493 | S | C | 168 | 273 | 633 | 27 |
| 493 | S | O | 180 | 270 | 631 | 27 |
| 493 | S | CB | 150 | 256 | 630 | 30 |
| 493 | S | OG | 142 | 246 | 637 | 44 |
| 494 | C | N | 164 | 285 | 630 | 26 |
| 494 | C | CA | 172 | 295 | 623 | 27 |
| 494 | C | C | 184 | 299 | 632 | 27 |
| 494 | C | O | 195 | 301 | 628 | 24 |
| 494 | C | CB | 164 | 307 | 619 | 25 |
| 494 | C | SG | 173 | 321 | 612 | 32 |
| 495 | L | N | 181 | 301 | 645 | 26 |
| 495 | L | CA | 192 | 305 | 655 | 25 |
| 495 | L | C | 202 | 294 | 656 | 28 |
| 495 | L | O | 214 | 297 | 656 | 30 |
| 495 | L | CB | 186 | 309 | 668 | 23 |
| 495 | L | CG | 175 | 319 | 669 | 23 |
| 495 | L | CD1 | 173 | 324 | 683 | 23 |
| 495 | L | CD2 | 178 | 331 | 659 | 21 |
| 496 | R | N | 198 | 282 | 657 | 26 |
| 496 | R | CA | 207 | 270 | 658 | 28 |
| 496 | R | C | 216 | 269 | 645 | 27 |
| 496 | R | O | 228 | 267 | 646 | 26 |
| 496 | R | CB | 200 | 257 | 661 | 28 |
| 496 | R | CG | 194 | 257 | 675 | 33 |
| 496 | R | CD | 187 | 244 | 678 | 31 |
| 496 | R | NE | 175 | 241 | 670 | 38 |
| 496 | R | CZ | 163 | 242 | 674 | 41 |
| 496 | R | NH1 | 160 | 246 | 686 | 46 |
| 496 | R | NH2 | 153 | 240 | 665 | 40 |
| 497 | K | N | 210 | 271 | 634 | 30 |
| 497 | K | CA | 217 | 271 | 621 | 27 |
| 497 | K | C | 228 | 281 | 619 | 26 |
| 497 | K | O | 239 | 278 | 616 | 25 |
| 497 | K | CB | 206 | 273 | 610 | 27 |
| 497 | K | CG | 212 | 274 | 596 | 26 |
| 497 | K | CD | 201 | 275 | 585 | 27 |
| 497 | K | CE | 194 | 288 | 586 | 26 |
| 497 | K | NZ | 184 | 290 | 575 | 27 |
| 498 | L | N | 224 | 294 | 623 | 26 |
| 498 | L | CA | 233 | 305 | 622 | 25 |
| 498 | L | C | 243 | 306 | 634 | 25 |
| 498 | L | O | 253 | 312 | 634 | 22 |
| 498 | L | CB | 225 | 318 | 621 | 27 |
| 498 | L | CG | 221 | 323 | 607 | 28 |
| 498 | L | CD1 | 217 | 313 | 597 | 29 |
| 498 | L | CD2 | 209 | 333 | 609 | 24 |
| 499 | G | N | 239 | 299 | 645 | 25 |
| 499 | G | CA | 247 | 300 | 657 | 23 |
| 499 | G | C | 245 | 313 | 665 | 23 |
| 499 | G | O | 254 | 320 | 670 | 22 |
| 500 | V | N | 232 | 317 | 666 | 23 |
| 500 | V | CA | 227 | 329 | 673 | 25 |
| 500 | V | C | 223 | 324 | 686 | 25 |
| 500 | V | O | 216 | 313 | 687 | 27 |
| 500 | V | CB | 215 | 335 | 665 | 23 |
| 500 | V | CG1 | 210 | 347 | 673 | 20 |
| 500 | V | CG2 | 219 | 339 | 651 | 22 |
| 501 | P | N | 226 | 331 | 697 | 26 |
| 501 | P | CA | 221 | 327 | 711 | 28 |
| 501 | P | C | 206 | 325 | 711 | 28 |
| 501 | P | O | 198 | 332 | 705 | 30 |
| 501 | P | CB | 226 | 339 | 719 | 24 |
| 501 | P | CG | 238 | 344 | 712 | 23 |
| 501 | P | CD | 233 | 344 | 698 | 25 |
| 502 | P | N | 201 | 315 | 719 | 27 |
| 502 | P | CA | 187 | 312 | 720 | 27 |
| 502 | P | C | 179 | 323 | 725 | 26 |
| 502 | P | O | 184 | 332 | 732 | 26 |
| 502 | P | CB | 187 | 299 | 729 | 27 |
| 502 | P | CG | 200 | 301 | 737 | 28 |
| 502 | P | CD | 209 | 305 | 727 | 26 |
| 503 | L | N | 166 | 324 | 722 | 26 |
| 503 | L | CA | 157 | 334 | 727 | 25 |
| 503 | L | C | 158 | 338 | 742 | 27 |
| 503 | L | O | 156 | 350 | 745 | 27 |
| 503 | L | CB | 143 | 332 | 722 | 25 |
| 503 | L | CG | 140 | 332 | 707 | 22 |
| 503 | L | CD1 | 126 | 327 | 705 | 24 |
| 503 | L | CD2 | 141 | 347 | 702 | 17 |
| 504 | R | N | 160 | 328 | 751 | 28 |
| 504 | R | CA | 160 | 331 | 765 | 28 |
| 504 | R | C | 172 | 341 | 768 | 27 |
| 504 | R | O | 171 | 349 | 777 | 27 |
| 504 | R | CB | 161 | 318 | 773 | 30 |
| 504 | R | CG | 172 | 309 | 768 | 36 |
| 504 | R | CD | 172 | 296 | 777 | 39 |
| 504 | R | NE | 180 | 286 | 771 | 45 |
| 504 | R | CZ | 193 | 286 | 771 | 47 |
| 504 | R | NH1 | 200 | 296 | 776 | 50 |
| 504 | R | NH2 | 200 | 276 | 765 | 48 |
| 505 | V | N | 183 | 340 | 761 | 26 |
| 505 | V | CA | 195 | 348 | 763 | 24 |
| 505 | V | C | 191 | 363 | 759 | 24 |
| 505 | V | O | 194 | 372 | 766 | 25 |
| 505 | V | CB | 207 | 344 | 754 | 21 |
| 505 | V | CG1 | 218 | 354 | 755 | 14 |
| 505 | V | CG2 | 212 | 330 | 760 | 17 |
| 506 | W | N | 183 | 364 | 748 | 22 |
| 506 | W | CA | 179 | 377 | 743 | 20 |
| 506 | W | C | 169 | 384 | 753 | 20 |
| 506 | W | O | 170 | 396 | 755 | 20 |
| 506 | W | CB | 173 | 376 | 729 | 20 |
| 506 | W | CG | 183 | 373 | 719 | 14 |
| 506 | W | CD1 | 184 | 361 | 713 | 13 |
| 506 | W | CD2 | 193 | 381 | 714 | 13 |
| 506 | W | NE1 | 195 | 361 | 704 | 13 |
| 506 | W | CE2 | 201 | 374 | 705 | 14 |
| 506 | W | CE3 | 197 | 394 | 717 | 14 |
| 506 | W | CZ2 | 212 | 379 | 699 | 14 |
| 506 | W | CZ3 | 208 | 400 | 710 | 17 |
| 506 | W | CH2 | 216 | 392 | 701 | 10 |
| 507 | R | N | 161 | 376 | 760 | 22 |
| 507 | R | CA | 151 | 381 | 770 | 22 |
| 507 | R | C | 159 | 387 | 782 | 21 |
| 507 | R | O | 156 | 397 | 787 | 20 |
| 507 | R | CB | 141 | 370 | 775 | 27 |
| 507 | R | CG | 133 | 374 | 787 | 28 |
| 507 | R | CD | 122 | 365 | 790 | 33 |
| 507 | R | NE | 110 | 369 | 782 | 38 |
| 507 | R | CZ | 105 | 362 | 772 | 35 |
| 507 | R | NH1 | 110 | 350 | 769 | 37 |
| 507 | R | NH2 | 94 | 367 | 766 | 35 |
| 508 | H | N | 170 | 380 | 785 | 23 |
| 508 | H | CA | 179 | 384 | 796 | 26 |
| 508 | H | C | 185 | 397 | 792 | 24 |
| 508 | H | O | 185 | 407 | 800 | 23 |
| 508 | H | CB | 189 | 374 | 800 | 32 |
| 508 | H | CG | 197 | 376 | 812 | 38 |
| 508 | H | ND1 | 196 | 368 | 823 | 44 |
| 508 | H | CD2 | 204 | 387 | 817 | 40 |
| 508 | H | CE1 | 202 | 373 | 834 | 44 |
| 508 | H | NE2 | 208 | 385 | 830 | 41 |
| 509 | R | N | 191 | 398 | 780 | 22 |
| 509 | R | CA | 197 | 410 | 775 | 19 |
| 509 | R | C | 187 | 422 | 774 | 18 |
| 509 | R | O | 191 | 433 | 776 | 16 |
| 509 | R | CB | 204 | 408 | 762 | 21 |
| 509 | R | CG | 215 | 397 | 762 | 20 |
| 509 | R | CD | 222 | 397 | 749 | 22 |
| 509 | R | NE | 234 | 387 | 749 | 22 |
| 509 | R | CZ | 239 | 382 | 739 | 22 |
| 509 | R | NH1 | 235 | 385 | 727 | 26 |
| 509 | R | NH2 | 249 | 373 | 741 | 21 |
| 510 | A | N | 175 | 419 | 770 | 19 |
| 510 | A | CA | 165 | 429 | 768 | 18 |
| 510 | A | C | 162 | 437 | 780 | 19 |
| 510 | A | O | 159 | 449 | 780 | 22 |
| 510 | A | CB | 152 | 423 | 762 | 17 |
| 511 | R | N | 162 | 430 | 792 | 25 |
| 511 | R | CA | 159 | 437 | 805 | 26 |
| 511 | R | C | 170 | 447 | 808 | 24 |
| 511 | R | O | 167 | 458 | 812 | 26 |

TABLE 1-continued

| | | | | | |
|---|---|---|---|---|---|
| 511 R | CB | 158 | 426 | 816 | 27 |
| 511 R | CG | 146 | 418 | 816 | 30 |
| 511 R | CD | 147 | 407 | 826 | 38 |
| 511 R | NE | 134 | 401 | 828 | 45 |
| 511 R | CZ | 132 | 388 | 830 | 51 |
| 511 R | NH1 | 142 | 379 | 830 | 54 |
| 511 R | NH2 | 119 | 383 | 831 | 49 |
| 512 S | N | 183 | 443 | 805 | 23 |
| 512 S | CA | 194 | 452 | 807 | 22 |
| 512 S | C | 193 | 464 | 797 | 20 |
| 512 S | O | 193 | 476 | 801 | 19 |
| 512 S | CB | 207 | 445 | 804 | 21 |
| 512 S | OG | 218 | 453 | 801 | 26 |
| 513 V | N | 191 | 461 | 784 | 21 |
| 513 V | CA | 190 | 472 | 774 | 20 |
| 513 V | C | 178 | 481 | 778 | 16 |
| 513 V | O | 179 | 493 | 776 | 21 |
| 513 V | CB | 187 | 466 | 759 | 22 |
| 513 V | CG1 | 184 | 477 | 749 | 17 |
| 513 V | CG2 | 199 | 458 | 754 | 23 |
| 514 R | N | 167 | 475 | 783 | 18 |
| 514 R | CA | 156 | 483 | 787 | 20 |
| 514 R | C | 158 | 492 | 798 | 18 |
| 514 R | O | 155 | 504 | 797 | 20 |
| 514 R | CB | 145 | 473 | 791 | 21 |
| 514 R | CG | 131 | 479 | 795 | 21 |
| 514 R | CD | 121 | 469 | 798 | 28 |
| 514 R | NE | 114 | 472 | 811 | 36 |
| 514 R | CZ | 107 | 483 | 813 | 37 |
| 514 R | NH1 | 105 | 492 | 804 | 42 |
| 514 R | NH2 | 102 | 485 | 825 | 41 |
| 515 A | N | 165 | 488 | 809 | 24 |
| 515 A | CA | 168 | 496 | 820 | 22 |
| 515 A | C | 178 | 507 | 816 | 22 |
| 515 A | O | 177 | 518 | 821 | 24 |
| 515 A | CB | 175 | 487 | 831 | 22 |
| 516 R | N | 187 | 504 | 807 | 24 |
| 516 R | CA | 196 | 514 | 802 | 27 |
| 516 R | C | 190 | 526 | 795 | 29 |
| 516 R | O | 194 | 537 | 797 | 30 |
| 516 R | CB | 206 | 507 | 793 | 28 |
| 516 R | CG | 220 | 505 | 799 | 29 |
| 516 R | CD | 224 | 490 | 799 | 24 |
| 516 R | NE | 229 | 485 | 786 | 29 |
| 516 R | CZ | 237 | 492 | 778 | 30 |
| 516 R | NH1 | 242 | 504 | 781 | 32 |
| 516 R | NH2 | 241 | 486 | 767 | 30 |
| 517 L | N | 179 | 522 | 787 | 30 |
| 517 L | CA | 172 | 532 | 780 | 27 |
| 517 L | C | 164 | 541 | 789 | 26 |
| 517 L | O | 164 | 554 | 788 | 24 |
| 517 L | CB | 162 | 526 | 770 | 26 |
| 517 L | CG | 169 | 519 | 758 | 23 |
| 517 L | CD1 | 159 | 511 | 750 | 21 |
| 517 L | CD2 | 175 | 530 | 749 | 23 |
| 518 L | N | 157 | 535 | 799 | 30 |
| 518 L | CA | 149 | 542 | 809 | 31 |
| 518 L | C | 158 | 552 | 817 | 32 |
| 518 L | O | 154 | 563 | 820 | 34 |
| 518 L | CB | 142 | 533 | 818 | 32 |
| 518 L | CG | 131 | 524 | 812 | 29 |
| 518 L | CD1 | 127 | 513 | 820 | 30 |
| 518 L | CD2 | 119 | 533 | 809 | 30 |
| 519 S | N | 171 | 549 | 819 | 35 |
| 519 S | CA | 181 | 557 | 826 | 36 |
| 519 S | C | 184 | 570 | 819 | 38 |
| 519 S | O | 189 | 579 | 825 | 38 |
| 519 S | CB | 193 | 549 | 829 | 36 |
| 519 S | OG | 191 | 537 | 837 | 41 |
| 520 Q | N | 182 | 570 | 806 | 39 |
| 520 Q | CA | 186 | 582 | 798 | 40 |
| 520 Q | C | 174 | 592 | 798 | 40 |
| 520 Q | O | 176 | 604 | 795 | 39 |
| 520 Q | CB | 188 | 578 | 783 | 42 |
| 520 Q | CG | 196 | 566 | 780 | 47 |
| 520 Q | CD | 211 | 568 | 783 | 52 |
| 520 Q | OE1 | 217 | 578 | 778 | 52 |
| 520 Q | NE2 | 217 | 558 | 790 | 52 |
| 521 G | N | 162 | 588 | 802 | 41 |
| 521 G | CA | 151 | 596 | 803 | 40 |
| 521 G | C | 147 | 600 | 789 | 43 |
| 521 G | O | 151 | 594 | 779 | 44 |
| 522 G | N | 139 | 611 | 788 | 44 |
| 522 G | CA | 134 | 616 | 775 | 42 |
| 522 G | C | 129 | 605 | 765 | 42 |
| 522 G | O | 122 | 596 | 769 | 43 |
| 523 R | N | 132 | 607 | 752 | 42 |
| 523 R | CA | 128 | 597 | 742 | 38 |
| 523 R | C | 135 | 584 | 743 | 36 |
| 523 R | O | 129 | 574 | 738 | 36 |
| 523 R | CB | 128 | 603 | 728 | 39 |
| 523 R | CG | 119 | 615 | 727 | 42 |
| 523 R | CD | 114 | 617 | 713 | 47 |
| 523 R | NE | 125 | 621 | 704 | 51 |
| 523 R | CZ | 127 | 616 | 692 | 51 |
| 523 R | NH1 | 119 | 607 | 688 | 50 |
| 523 R | NH2 | 137 | 620 | 685 | 48 |
| 524 A | N | 146 | 583 | 749 | 30 |
| 524 A | CA | 154 | 571 | 750 | 26 |
| 524 A | C | 145 | 562 | 760 | 24 |
| 524 A | O | 144 | 550 | 758 | 23 |
| 524 A | CB | 167 | 573 | 756 | 25 |
| 525 A | N | 139 | 568 | 770 | 26 |
| 525 A | CA | 131 | 561 | 780 | 27 |
| 525 A | C | 119 | 555 | 773 | 25 |
| 525 A | O | 115 | 544 | 776 | 25 |
| 525 A | CB | 127 | 570 | 791 | 28 |
| 526 T | N | 112 | 563 | 765 | 27 |
| 526 T | CA | 100 | 558 | 758 | 26 |
| 526 T | C | 103 | 546 | 749 | 23 |
| 526 T | O | 96 | 536 | 749 | 22 |
| 526 T | CB | 94 | 569 | 749 | 27 |
| 526 T | OG1 | 94 | 581 | 756 | 32 |
| 526 T | CG2 | 80 | 566 | 744 | 30 |
| 527 C | N | 115 | 545 | 743 | 23 |
| 527 C | CA | 120 | 534 | 735 | 22 |
| 527 C | C | 121 | 522 | 745 | 22 |
| 527 C | O | 117 | 511 | 741 | 22 |
| 527 C | CB | 133 | 536 | 729 | 24 |
| 527 C | SG | 134 | 546 | 714 | 25 |
| 528 G | N | 126 | 524 | 757 | 23 |
| 528 G | CA | 128 | 513 | 766 | 21 |
| 528 G | C | 114 | 508 | 771 | 21 |
| 528 G | O | 111 | 496 | 771 | 21 |
| 529 K | N | 105 | 518 | 774 | 25 |
| 529 K | CA | 92 | 515 | 779 | 28 |
| 529 K | C | 83 | 507 | 769 | 29 |
| 529 K | O | 76 | 497 | 772 | 29 |
| 529 K | CB | 85 | 527 | 784 | 28 |
| 529 K | CG | 70 | 525 | 788 | 33 |
| 529 K | CD | 64 | 539 | 792 | 37 |
| 529 K | CE | 49 | 537 | 794 | 40 |
| 529 K | NZ | 43 | 551 | 797 | 40 |
| 530 Y | N | 82 | 512 | 756 | 27 |
| 530 Y | CA | 74 | 506 | 746 | 25 |
| 530 Y | C | 80 | 494 | 738 | 21 |
| 530 Y | O | 73 | 484 | 737 | 20 |
| 530 Y | CB | 69 | 516 | 736 | 25 |
| 530 Y | CG | 59 | 526 | 741 | 25 |
| 530 Y | CD1 | 62 | 536 | 749 | 30 |
| 530 Y | CD2 | 45 | 524 | 738 | 26 |
| 530 Y | CE1 | 53 | 545 | 755 | 29 |
| 530 Y | CE2 | 36 | 533 | 743 | 29 |
| 530 Y | CZ | 40 | 543 | 752 | 31 |
| 530 Y | OH | 31 | 552 | 757 | 34 |
| 531 L | N | 92 | 496 | 734 | 23 |
| 531 L | CA | 99 | 485 | 726 | 21 |
| 531 L | C | 102 | 472 | 734 | 20 |
| 531 L | O | 102 | 462 | 729 | 19 |
| 531 L | CB | 111 | 490 | 719 | 17 |
| 531 L | CG | 110 | 503 | 711 | 20 |
| 531 L | CD1 | 123 | 506 | 704 | 21 |
| 531 L | CD2 | 99 | 502 | 701 | 19 |
| 532 F | N | 105 | 474 | 747 | 21 |
| 532 F | CA | 109 | 462 | 755 | 21 |
| 532 F | C | 99 | 459 | 767 | 26 |
| 532 F | O | 103 | 452 | 776 | 22 |
| 532 F | CB | 123 | 464 | 760 | 23 |

TABLE 1-continued

| | | | | | |
|---|---|---|---|---|---|
| 532 F | CG | 133 | 466 | 749 | 20 |
| 532 F | CD1 | 139 | 455 | 743 | 18 |
| 532 F | CD2 | 137 | 478 | 745 | 19 |
| 532 F | CE1 | 147 | 456 | 732 | 17 |
| 532 F | CE2 | 146 | 480 | 734 | 16 |
| 532 F | CZ | 151 | 469 | 728 | 8 |
| 533 N | N | 87 | 462 | 765 | 28 |
| 533 N | CA | 77 | 459 | 776 | 30 |
| 533 N | C | 75 | 444 | 777 | 28 |
| 533 N | O | 72 | 439 | 787 | 29 |
| 533 N | CB | 63 | 466 | 773 | 33 |
| 533 N | CG | 55 | 469 | 786 | 38 |
| 533 N | OD1 | 46 | 462 | 789 | 40 |
| 533 N | ND2 | 59 | 480 | 792 | 40 |
| 534 W | N | 78 | 437 | 765 | 26 |
| 534 W | CA | 77 | 422 | 765 | 23 |
| 534 W | C | 87 | 415 | 774 | 27 |
| 534 W | O | 85 | 403 | 777 | 27 |
| 534 W | CB | 79 | 417 | 750 | 24 |
| 534 W | CG | 92 | 421 | 744 | 23 |
| 534 W | CD1 | 96 | 432 | 737 | 24 |
| 534 W | CD2 | 105 | 414 | 745 | 20 |
| 534 W | NE1 | 109 | 432 | 734 | 20 |
| 534 W | CE2 | 115 | 421 | 739 | 21 |
| 534 W | CE3 | 108 | 402 | 752 | 19 |
| 534 W | CZ2 | 128 | 417 | 738 | 19 |
| 534 W | CZ3 | 122 | 397 | 751 | 20 |
| 534 W | CH2 | 131 | 405 | 744 | 17 |
| 535 A | N | 98 | 422 | 777 | 28 |
| 535 A | CA | 108 | 417 | 785 | 30 |
| 535 A | C | 106 | 415 | 800 | 32 |
| 535 A | O | 111 | 406 | 806 | 32 |
| 535 A | CB | 122 | 424 | 782 | 29 |
| 536 V | N | 99 | 425 | 806 | 35 |
| 536 V | CA | 96 | 425 | 820 | 39 |
| 536 V | C | 83 | 416 | 824 | 44 |
| 536 V | O | 75 | 414 | 815 | 43 |
| 536 V | CB | 94 | 439 | 826 | 40 |
| 536 V | CG1 | 107 | 446 | 828 | 40 |
| 536 V | CG2 | 85 | 447 | 817 | 33 |
| 537 K | N | 83 | 411 | 836 | 49 |
| 537 K | CA | 71 | 403 | 840 | 51 |
| 537 K | C | 59 | 411 | 843 | 53 |
| 537 K | O | 48 | 409 | 839 | 54 |
| 537 K | CB | 75 | 393 | 851 | 53 |
| 537 K | CG | 81 | 399 | 864 | 59 |
| 537 K | CD | 87 | 389 | 873 | 61 |
| 537 K | CE | 98 | 394 | 882 | 62 |
| 537 K | NZ | 106 | 384 | 888 | 61 |
| 538 T | N | 61 | 422 | 851 | 55 |
| 538 T | CA | 50 | 431 | 854 | 55 |
| 538 T | C | 51 | 442 | 844 | 54 |
| 538 T | O | 60 | 451 | 844 | 52 |
| 538 T | CB | 52 | 437 | 869 | 55 |
| 538 T | OG1 | 53 | 427 | 878 | 51 |
| 538 T | CG2 | 40 | 446 | 872 | 53 |
| 539 K | N | 43 | 441 | 834 | 53 |
| 539 K | CA | 42 | 450 | 822 | 53 |
| 539 K | C | 36 | 464 | 825 | 53 |
| 539 K | O | 27 | 465 | 834 | 54 |
| 539 K | CB | 33 | 443 | 811 | 53 |
| 539 K | CG | 34 | 428 | 810 | 51 |
| 539 K | CD | 46 | 424 | 801 | 50 |
| 539 K | CE | 47 | 409 | 799 | 52 |
| 539 K | NZ | 57 | 404 | 790 | 52 |
| 540 L | N | 41 | 474 | 818 | 50 |
| 540 L | CA | 36 | 487 | 820 | 49 |
| 540 L | C | 24 | 491 | 812 | 49 |
| 540 L | O | 19 | 483 | 804 | 49 |
| 540 L | CB | 47 | 498 | 817 | 46 |
| 540 L | CG | 59 | 501 | 827 | 47 |
| 540 L | CD1 | 62 | 516 | 825 | 45 |
| 540 L | CD2 | 55 | 498 | 841 | 48 |
| 541 K | N | 20 | 504 | 814 | 51 |
| 541 K | CA | 8 | 510 | 808 | 49 |
| 541 K | C | 6 | 509 | 793 | 48 |
| 541 K | O | −1 | 500 | 788 | 47 |
| 541 K | CB | 8 | 525 | 811 | 50 |
| 541 K | CG | 17 | 529 | 823 | 51 |
| 541 K | CD | 18 | 544 | 825 | 53 |
| 541 K | CE | 21 | 549 | 840 | 54 |
| 541 K | NZ | 9 | 548 | 849 | 48 |
| 542 L | N | 14 | 516 | 785 | 48 |
| 542 L | CA | 15 | 517 | 771 | 45 |
| 542 L | C | 2 | 523 | 765 | 43 |
| 542 L | O | −7 | 516 | 761 | 43 |
| 542 L | CB | 18 | 503 | 765 | 40 |
| 542 L | CG | 33 | 501 | 763 | 34 |
| 542 L | CD1 | 41 | 506 | 775 | 31 |
| 542 L | CD2 | 35 | 486 | 761 | 32 |
| 543 T | N | 2 | 536 | 765 | 42 |
| 543 T | CA | −8 | 544 | 760 | 43 |
| 543 T | C | −3 | 551 | 748 | 43 |
| 543 T | O | 8 | 550 | 744 | 42 |
| 543 T | CB | −12 | 554 | 771 | 42 |
| 543 T | OG1 | 0 | 562 | 774 | 40 |
| 543 T | CG2 | −17 | 548 | 784 | 41 |
| 544 P | N | −13 | 556 | 740 | 43 |
| 544 P | CA | −8 | 563 | 728 | 44 |
| 544 P | C | 1 | 574 | 730 | 45 |
| 544 P | O | 0 | 583 | 739 | 45 |
| 544 P | CB | −22 | 568 | 722 | 44 |
| 544 P | CG | −31 | 557 | 726 | 43 |
| 544 P | CD | −27 | 554 | 740 | 42 |
| 545 I | N | 12 | 574 | 723 | 44 |
| 545 I | CA | 23 | 584 | 724 | 42 |
| 545 I | C | 18 | 596 | 716 | 45 |
| 545 I | O | 15 | 596 | 704 | 45 |
| 545 I | CB | 36 | 579 | 717 | 40 |
| 545 I | CG1 | 40 | 565 | 723 | 35 |
| 545 I | CG2 | 47 | 589 | 720 | 39 |
| 545 I | CD1 | 51 | 559 | 715 | 36 |
| 546 P | N | 17 | 608 | 723 | 47 |
| 546 P | CA | 12 | 621 | 717 | 48 |
| 546 P | C | 19 | 626 | 705 | 51 |
| 546 P | O | 13 | 631 | 695 | 51 |
| 546 P | CB | 13 | 630 | 729 | 49 |
| 546 P | CG | 24 | 624 | 737 | 51 |
| 546 P | CD | 20 | 610 | 737 | 47 |
| 547 A | N | 33 | 625 | 704 | 52 |
| 547 A | CA | 40 | 629 | 693 | 51 |
| 547 A | C | 40 | 620 | 680 | 49 |
| 547 A | O | 47 | 623 | 670 | 49 |
| 547 A | CB | 55 | 632 | 697 | 52 |
| 548 A | N | 32 | 610 | 681 | 49 |
| 548 A | CA | 31 | 600 | 670 | 49 |
| 548 A | C | 23 | 606 | 658 | 51 |
| 548 A | O | 26 | 603 | 646 | 51 |
| 548 A | CB | 25 | 587 | 674 | 45 |
| 549 S | N | 12 | 613 | 661 | 54 |
| 549 S | CA | 4 | 619 | 651 | 55 |
| 549 S | C | 10 | 630 | 643 | 56 |
| 549 S | O | 6 | 633 | 632 | 59 |
| 549 S | CB | −8 | 624 | 657 | 52 |
| 549 S | OG | −6 | 634 | 667 | 52 |
| 550 Q | N | 21 | 636 | 648 | 55 |
| 550 Q | CA | 29 | 646 | 641 | 56 |
| 550 Q | C | 36 | 641 | 628 | 53 |
| 550 Q | O | 37 | 649 | 618 | 50 |
| 550 Q | CB | 39 | 653 | 650 | 60 |
| 550 Q | CG | 35 | 661 | 662 | 66 |
| 550 Q | CD | 46 | 667 | 670 | 70 |
| 550 Q | OE1 | 56 | 659 | 673 | 69 |
| 550 Q | NE2 | 45 | 679 | 674 | 72 |
| 551 L | N | 41 | 629 | 629 | 51 |
| 551 L | CA | 48 | 623 | 618 | 50 |
| 551 L | C | 41 | 623 | 605 | 50 |
| 551 L | O | 30 | 618 | 604 | 50 |
| 551 L | CB | 52 | 608 | 622 | 49 |
| 551 L | CG | 61 | 606 | 634 | 48 |
| 551 L | CD1 | 62 | 591 | 637 | 43 |
| 551 L | CD2 | 75 | 612 | 632 | 46 |
| 552 D | N | 48 | 628 | 594 | 48 |
| 552 D | CA | 42 | 628 | 581 | 49 |
| 552 D | C | 44 | 614 | 574 | 47 |
| 552 D | O | 54 | 612 | 567 | 48 |
| 552 D | CB | 48 | 639 | 573 | 50 |
| 552 D | CG | 41 | 642 | 560 | 52 |

TABLE 1-continued

| | | | | | |
|---|---|---|---|---|---|
| 552 D | OD1 | 33 | 633 | 555 | 52 |
| 552 D | OD2 | 44 | 652 | 554 | 54 |
| 553 L | N | 36 | 604 | 577 | 46 |
| 553 L | CA | 37 | 591 | 572 | 45 |
| 553 L | C | 31 | 589 | 558 | 46 |
| 553 L | O | 30 | 577 | 554 | 44 |
| 553 L | CB | 33 | 580 | 582 | 43 |
| 553 L | CG | 44 | 573 | 590 | 45 |
| 553 L | CD1 | 53 | 583 | 596 | 40 |
| 553 L | CD2 | 37 | 564 | 600 | 40 |
| 554 S | N | 26 | 599 | 552 | 47 |
| 554 S | CA | 19 | 598 | 539 | 50 |
| 554 S | C | 30 | 597 | 529 | 50 |
| 554 S | O | 41 | 603 | 530 | 54 |
| 554 S | CB | 10 | 610 | 536 | 50 |
| 554 S | OG | 18 | 622 | 535 | 49 |
| 555 G | N | 28 | 588 | 519 | 48 |
| 555 G | CA | 38 | 586 | 509 | 42 |
| 555 G | C | 46 | 574 | 512 | 39 |
| 555 G | O | 54 | 569 | 504 | 39 |
| 556 W | N | 44 | 568 | 524 | 35 |
| 556 W | CA | 52 | 557 | 529 | 37 |
| 556 W | C | 48 | 544 | 522 | 38 |
| 556 W | O | 56 | 536 | 517 | 39 |
| 556 W | CB | 51 | 555 | 544 | 35 |
| 556 W | CG | 62 | 561 | 551 | 35 |
| 556 W | CD1 | 66 | 574 | 549 | 32 |
| 556 W | CD2 | 70 | 556 | 561 | 33 |
| 556 W | NE1 | 77 | 577 | 558 | 33 |
| 556 W | CE2 | 79 | 566 | 566 | 34 |
| 556 W | CE3 | 70 | 543 | 568 | 30 |
| 556 W | CZ2 | 88 | 564 | 576 | 33 |
| 556 W | CZ3 | 79 | 541 | 578 | 34 |
| 556 W | CH2 | 88 | 551 | 582 | 35 |
| 557 F | N | 35 | 541 | 521 | 33 |
| 557 F | CA | 29 | 529 | 515 | 31 |
| 557 F | C | 20 | 533 | 504 | 30 |
| 557 F | O | 8 | 533 | 505 | 30 |
| 557 F | CB | 22 | 521 | 525 | 27 |
| 557 F | CG | 31 | 517 | 537 | 28 |
| 557 F | CD1 | 42 | 508 | 535 | 25 |
| 557 F | CD2 | 29 | 523 | 549 | 29 |
| 557 F | CE1 | 50 | 505 | 545 | 25 |
| 557 F | CE2 | 38 | 520 | 560 | 30 |
| 557 F | CZ | 48 | 511 | 558 | 28 |
| 558 V | N | 25 | 538 | 493 | 26 |
| 558 V | CA | 17 | 543 | 481 | 26 |
| 558 V | C | 22 | 535 | 469 | 26 |
| 558 V | O | 13 | 529 | 462 | 24 |
| 558 V | CB | 19 | 558 | 479 | 24 |
| 558 V | CG1 | 11 | 562 | 467 | 29 |
| 558 V | CG2 | 15 | 565 | 491 | 27 |
| 559 A | N | 35 | 535 | 467 | 24 |
| 559 A | CA | 40 | 528 | 455 | 24 |
| 559 A | C | 54 | 522 | 457 | 21 |
| 559 A | O | 60 | 525 | 467 | 24 |
| 559 A | CB | 40 | 537 | 443 | 26 |
| 560 G | N | 57 | 513 | 448 | 22 |
| 560 G | CA | 71 | 506 | 449 | 23 |
| 560 G | C | 80 | 514 | 441 | 24 |
| 560 G | O | 77 | 519 | 430 | 18 |
| 561 Y | N | 93 | 515 | 445 | 22 |
| 561 Y | CA | 103 | 522 | 438 | 18 |
| 561 Y | C | 117 | 514 | 437 | 20 |
| 561 Y | O | 127 | 521 | 435 | 22 |
| 561 Y | CB | 106 | 536 | 444 | 16 |
| 561 Y | CG | 94 | 545 | 445 | 20 |
| 561 Y | CD1 | 89 | 551 | 433 | 19 |
| 561 Y | CD2 | 86 | 546 | 457 | 20 |
| 561 Y | CE1 | 78 | 559 | 434 | 17 |
| 561 Y | CE2 | 75 | 554 | 457 | 23 |
| 561 Y | CZ | 71 | 561 | 446 | 23 |
| 561 Y | OH | 59 | 568 | 447 | 20 |
| 562 S | N | 116 | 501 | 438 | 22 |
| 562 S | CA | 128 | 493 | 438 | 23 |
| 562 S | C | 137 | 496 | 426 | 25 |
| 562 S | O | 132 | 495 | 414 | 25 |
| 562 S | CB | 125 | 478 | 438 | 23 |
| 562 S | OG | 136 | 470 | 440 | 31 |
| 563 G | N | 149 | 501 | 428 | 26 |
| 563 G | CA | 158 | 505 | 417 | 21 |
| 563 G | C | 155 | 519 | 411 | 22 |
| 563 G | O | 163 | 524 | 403 | 25 |
| 564 G | N | 145 | 525 | 416 | 16 |
| 564 G | CA | 141 | 538 | 411 | 15 |
| 564 G | C | 148 | 551 | 416 | 14 |
| 564 G | O | 143 | 562 | 413 | 16 |
| 565 D | N | 159 | 550 | 423 | 19 |
| 565 D | CA | 166 | 561 | 428 | 17 |
| 565 D | C | 158 | 572 | 435 | 18 |
| 565 D | O | 159 | 584 | 433 | 17 |
| 565 D | CB | 173 | 568 | 416 | 19 |
| 565 D | CG | 185 | 577 | 420 | 25 |
| 565 D | OD1 | 192 | 574 | 430 | 26 |
| 565 D | OD2 | 187 | 587 | 413 | 23 |
| 566 I | N | 149 | 567 | 444 | 21 |
| 566 I | CA | 140 | 576 | 452 | 21 |
| 566 I | C | 144 | 578 | 467 | 22 |
| 566 I | O | 148 | 568 | 474 | 20 |
| 566 I | CB | 125 | 571 | 451 | 18 |
| 566 I | CG1 | 121 | 571 | 436 | 17 |
| 566 I | CG2 | 116 | 579 | 460 | 15 |
| 566 I | CD1 | 121 | 585 | 429 | 16 |
| 567 Y | N | 142 | 590 | 472 | 23 |
| 567 Y | CA | 146 | 593 | 486 | 27 |
| 567 Y | C | 135 | 602 | 493 | 35 |
| 567 Y | O | 129 | 611 | 486 | 34 |
| 567 Y | CB | 159 | 600 | 486 | 27 |
| 567 Y | CG | 163 | 606 | 500 | 28 |
| 567 Y | CD1 | 170 | 598 | 510 | 32 |
| 567 Y | CD2 | 161 | 620 | 503 | 27 |
| 567 Y | CE1 | 173 | 604 | 522 | 33 |
| 567 Y | CE2 | 165 | 625 | 515 | 31 |
| 567 Y | CZ | 171 | 617 | 525 | 35 |
| 567 Y | OH | 175 | 622 | 537 | 39 |
| 568 H | N | 134 | 601 | 506 | 40 |
| 568 H | CA | 124 | 609 | 514 | 43 |
| 568 H | C | 130 | 613 | 527 | 46 |
| 568 H | O | 138 | 605 | 533 | 44 |
| 568 H | CB | 111 | 602 | 515 | 40 |
| 568 H | CG | 103 | 601 | 503 | 42 |
| 568 H | ND1 | 99 | 590 | 497 | 44 |
| 568 H | CD2 | 98 | 611 | 495 | 40 |
| 568 H | CE1 | 91 | 592 | 486 | 41 |
| 568 H | NE2 | 90 | 605 | 485 | 41 |
| 569 S | N | 126 | 624 | 533 | 52 |
| 569 S | CA | 130 | 629 | 546 | 57 |
| 569 S | C | 145 | 632 | 546 | 60 |
| 569 S | O | 149 | 642 | 540 | 64 |
| 569 S | CB | 127 | 619 | 557 | 57 |
| 569 S | OG | 115 | 622 | 564 | 56 |
| 1001 X | OW | 165 | 413 | 548 | 8 |
| 1002 X | OW | 112 | 514 | 403 | 14 |
| 1003 X | OW | 136 | 486 | 313 | 13 |
| 1004 X | OW | 91 | 459 | 426 | 16 |
| 1005 X | OW | 57 | 632 | 371 | 17 |
| 1006 X | OW | 75 | 386 | 325 | 14 |
| 1007 X | OW | 23 | 397 | 463 | 18 |
| 1008 X | OW | 52 | 499 | 414 | 15 |
| 1009 X | OW | 252 | 550 | 342 | 17 |
| 1010 X | OW | 229 | 624 | 323 | 18 |
| 1011 X | OW | 160 | 565 | 378 | 18 |
| 1012 X | OW | 196 | 521 | 276 | 18 |
| 1013 X | OW | 33 | 447 | 296 | 18 |
| 1014 X | OW | 79 | 518 | 287 | 18 |
| 1015 X | OW | 212 | 489 | 291 | 17 |
| 1016 X | OW | 252 | 584 | 376 | 16 |
| 1017 X | OW | 113 | 500 | 325 | 24 |
| 1018 X | OW | 312 | 471 | 360 | 18 |
| 1019 X | OW | 81 | 456 | 711 | 16 |
| 1020 X | OW | 231 | 575 | 307 | 15 |
| 1021 X | OW | 97 | 482 | 449 | 19 |
| 1022 X | OW | −38 | 559 | 427 | 24 |
| 1023 X | OW | −95 | 504 | 265 | 19 |
| 1024 X | OW | 239 | 583 | 267 | 21 |
| 1025 X | OW | 81 | 523 | 391 | 17 |
| 1026 X | OW | 19 | 654 | 323 | 25 |
| 1027 X | OW | 180 | 612 | 403 | 29 |

TABLE 1-continued

| | | | | | |
|---|---|---|---|---|---|
| 1028 X | OW | 4 | 340 | 540 | 18 |
| 1029 X | OW | 91 | 415 | 219 | 24 |
| 1030 X | OW | 19 | 283 | 472 | 24 |
| 1031 X | OW | 307 | 451 | 398 | 19 |
| 1032 X | OW | 30 | 421 | 287 | 19 |
| 1033 X | OW | 270 | 617 | 443 | 22 |
| 1034 X | OW | 6 | 434 | 219 | 20 |
| 1035 X | OW | −7 | 537 | 426 | 18 |
| 1036 X | OW | 70 | 361 | 648 | 23 |
| 1037 X | OW | 7 | 451 | 616 | 31 |
| 1038 X | OW | 71 | 460 | 683 | 26 |
| 1039 X | OW | 14 | 474 | 596 | 24 |
| 1040 X | OW | 298 | 406 | 622 | 13 |
| 1041 X | OW | 58 | 525 | 411 | 19 |
| 1042 X | OW | 172 | 516 | 231 | 20 |
| 1043 X | OW | 48 | 425 | 603 | 17 |
| 1044 X | OW | 100 | 333 | 615 | 27 |
| 1045 X | OW | 145 | 396 | 380 | 26 |
| 1046 X | OW | 234 | 400 | 448 | 27 |
| 1047 X | OW | 135 | 450 | 244 | 25 |
| 1048 X | OW | 220 | 557 | 646 | 19 |
| 1049 X | OW | 377 | 446 | 646 | 18 |
| 1050 X | OW | 189 | 447 | 332 | 25 |
| 1051 X | OW | −18 | 648 | 396 | 35 |
| 1052 X | OW | 22 | 688 | 336 | 21 |
| 1053 X | OW | 71 | 455 | 740 | 21 |
| 1054 X | OW | 120 | 411 | 227 | 24 |
| 1055 X | OW | −69 | 335 | 215 | 24 |
| 1056 X | OW | 328 | 503 | 585 | 27 |
| 1057 X | OW | 101 | 337 | 546 | 23 |
| 1058 X | OW | −108 | 372 | 285 | 26 |
| 1059 X | OW | 228 | 432 | 519 | 27 |
| 1060 X | OW | −69 | 575 | 268 | 33 |
| 1061 X | OW | 257 | 562 | 318 | 25 |
| 1062 X | OW | 142 | 540 | 450 | 27 |
| 1063 X | OW | −84 | 536 | 269 | 31 |
| 1064 X | OW | 304 | 361 | 446 | 27 |
| 1065 X | OW | 11 | 258 | 262 | 28 |
| 1066 X | OW | 36 | 267 | 276 | 27 |
| 1067 X | OW | 284 | 341 | 452 | 26 |
| 1068 X | OW | 202 | 399 | 380 | 20 |
| 1069 X | OW | 135 | 415 | 550 | 20 |
| 1070 X | OW | −13 | 536 | 457 | 22 |
| 1071 X | OW | 85 | 508 | 314 | 23 |
| 1072 X | OW | −91 | 574 | 386 | 23 |
| 1073 X | OW | 11 | 405 | 192 | 21 |
| 1074 X | OW | 292 | 576 | 392 | 28 |
| 1075 X | OW | 141 | 614 | 166 | 31 |
| 1076 X | OW | 123 | 370 | 394 | 24 |
| 1077 X | OW | 271 | 573 | 350 | 36 |
| 1078 X | OW | −14 | 319 | 244 | 36 |
| 1079 X | OW | −62 | 463 | 539 | 25 |
| 1080 X | OW | −166 | 406 | −146 | 6 |
| 1081 X | OW | −112 | 511 | −1 | 14 |
| 1082 X | OW | −136 | 488 | 90 | 14 |
| 1083 X | OW | −92 | 455 | −21 | 11 |
| 1084 X | OW | −55 | 629 | 27 | 14 |
| 1085 X | OW | −76 | 386 | 80 | 24 |
| 1086 X | OW | −28 | 381 | −56 | 23 |
| 1087 X | OW | −52 | 494 | −12 | 18 |
| 1088 X | OW | −252 | 552 | 58 | 19 |
| 1089 X | OW | −226 | 623 | 75 | 23 |
| 1090 X | OW | −158 | 564 | 21 | 12 |
| 1091 X | OW | −196 | 525 | 127 | 15 |
| 1092 X | OW | −35 | 445 | 109 | 19 |
| 1093 X | OW | −80 | 517 | 116 | 13 |
| 1094 X | OW | −214 | 491 | 112 | 18 |
| 1095 X | OW | −250 | 581 | 24 | 20 |
| 1096 X | OW | −111 | 498 | 78 | 16 |
| 1097 X | OW | −311 | 475 | 40 | 20 |
| 1098 X | OW | −80 | 446 | −308 | 23 |
| 1099 X | OW | −232 | 576 | 92 | 16 |
| 1100 X | OW | −97 | 477 | −47 | 20 |
| 1101 X | OW | 37 | 552 | −24 | 15 |
| 1102 X | OW | 92 | 502 | 135 | 19 |
| 1103 X | OW | −237 | 586 | 135 | 29 |
| 1104 X | OW | −81 | 519 | 10 | 20 |
| 1105 X | OW | −19 | 651 | 73 | 19 |
| 1106 X | OW | −178 | 608 | −7 | 17 |
| 1107 X | OW | −7 | 332 | −135 | 16 |
| 1108 X | OW | −96 | 415 | 185 | 19 |
| 1109 X | OW | −23 | 278 | −70 | 32 |
| 1110 X | OW | −307 | 457 | 3 | 21 |
| 1111 X | OW | −33 | 420 | 120 | 21 |
| 1112 X | OW | −273 | 611 | −48 | 22 |
| 1113 X | OW | −12 | 431 | 186 | 19 |
| 1114 X | OW | 6 | 532 | −25 | 18 |
| 1115 X | OW | −72 | 355 | −244 | 16 |
| 1116 X | OW | −9 | 442 | −213 | 24 |
| 1117 X | OW | −74 | 451 | −280 | 28 |
| 1118 X | OW | −17 | 468 | −193 | 27 |
| 1119 X | OW | −300 | 400 | −222 | 17 |
| 1120 X | OW | −58 | 520 | −10 | 24 |
| 1121 X | OW | −173 | 520 | 172 | 18 |
| 1122 X | OW | −50 | 419 | −199 | 23 |
| 1123 X | OW | −103 | 327 | −211 | 17 |
| 1124 X | OW | −148 | 396 | 23 | 25 |
| 1125 X | OW | −237 | 397 | −46 | 22 |
| 1126 X | OW | −138 | 452 | 161 | 21 |
| 1127 X | OW | −220 | 553 | −247 | 26 |
| 1128 X | OW | −376 | 445 | −245 | 17 |
| 1129 X | OW | −189 | 450 | 71 | 19 |
| 1130 X | OW | 15 | 645 | −1 | 24 |
| 1131 X | OW | −19 | 688 | 56 | 24 |
| 1132 X | OW | −71 | 444 | −336 | 21 |
| 1133 X | OW | −125 | 414 | 175 | 23 |
| 1134 X | OW | 66 | 330 | 187 | 32 |
| 1135 X | OW | −315 | 495 | −144 | 45 |
| 1136 X | OW | −106 | 330 | −140 | 26 |
| 1137 X | OW | 103 | 369 | 122 | 30 |
| 1138 X | OW | −226 | 427 | −118 | 23 |
| 1139 X | OW | 50 | 604 | 151 | 51 |
| 1140 X | OW | −255 | 563 | 83 | 23 |
| 1141 X | OW | −140 | 536 | −50 | 20 |
| 1142 X | OW | 68 | 571 | 134 | 39 |
| 1143 X | OW | −303 | 365 | −42 | 35 |
| 1144 X | OW | −17 | 253 | 146 | 36 |
| 1145 X | OW | −42 | 265 | 131 | 23 |
| 1146 X | OW | −290 | 344 | −54 | 27 |
| 1147 X | OW | −206 | 397 | 21 | 19 |
| 1148 X | OW | −135 | 409 | −145 | 22 |
| 1149 X | OW | 13 | 526 | −54 | 27 |
| 1150 X | OW | −82 | 508 | 86 | 32 |
| 1151 X | OW | 89 | 570 | 14 | 23 |
| 1152 X | OW | −14 | 405 | 210 | 24 |
| 1153 X | OW | −289 | 572 | 12 | 33 |
| 1154 X | OW | −143 | 621 | 230 | 29 |
| 1155 X | OW | −129 | 368 | 11 | 34 |
| 1156 X | OW | −266 | 574 | 47 | 28 |
| 1157 X | OW | 3 | 319 | 162 | 36 |
| 1158 X | OW | 60 | 453 | −137 | 21 |
| 1159 X | OW | −29 | 324 | −245 | 26 |
| 1160 X | OW | 186 | 430 | 590 | 22 |
| 1161 X | OW | −186 | 423 | −190 | 24 |
| 1162 X | OW | −51 | 306 | −201 | 22 |
| 1163 X | OW | −27 | 295 | −209 | 26 |
| 1164 X | OW | 74 | 331 | 547 | 25 |
| 1165 X | OW | 105 | 465 | 471 | 20 |
| 1166 X | OW | −157 | 291 | −305 | 23 |
| 1167 X | OW | 21 | 429 | 604 | 25 |
| 1168 X | OW | −30 | 273 | 296 | 25 |
| 1169 X | OW | 155 | 296 | 708 | 20 |
| 1170 X | OW | 222 | 580 | 723 | 21 |
| 1171 X | OW | 200 | 291 | 693 | 25 |
| 1172 X | OW | −62 | 355 | 13 | 27 |
| 1173 X | OW | 133 | 479 | 502 | 21 |
| 1174 X | OW | −40 | 518 | 173 | 21 |
| 1175 X | OW | −215 | 573 | −99 | 28 |
| 1176 X | OW | −111 | 165 | 440 | 49 |
| 1177 X | OW | −158 | 336 | −146 | 28 |
| 1178 X | OW | 232 | 621 | 295 | 25 |
| 1179 X | OW | −306 | 459 | −23 | 27 |
| 1180 X | OW | 14 | 517 | −131 | 29 |
| 1181 X | OW | −163 | 355 | −111 | 29 |
| 1182 X | OW | 155 | 346 | 549 | 25 |
| 1183 X | OW | −226 | 371 | −45 | 27 |
| 1184 X | OW | −304 | 392 | −312 | 31 |
| 1185 X | OW | 142 | 464 | 828 | 25 |

TABLE 1-continued

| | | | | | |
|---|---|---|---|---|---|
| 1186 X | OW | −161 | 501 | −51 | 25 |
| 1187 X | OW | 143 | 582 | 390 | 29 |
| 1188 X | OW | −274 | 748 | −6 | 28 |
| 1189 X | OW | −152 | 288 | −339 | 23 |
| 1190 X | OW | 239 | 419 | 716 | 27 |
| 1191 X | OW | −32 | 518 | 683 | 28 |
| 1192 X | OW | −201 | 334 | −124 | 25 |
| 1193 X | OW | −233 | 620 | 102 | 21 |
| 1194 X | OW | −326 | 342 | −155 | 28 |
| 1195 X | OW | 372 | 430 | 750 | 52 |
| 1196 X | OW | −103 | 459 | −68 | 28 |
| 1197 X | OW | 216 | 583 | 498 | 26 |
| 1198 X | OW | −354 | 354 | −61 | 38 |
| 1199 X | OW | 104 | 163 | 52 | 29 |
| 1200 X | OW | 60 | 293 | 420 | 26 |
| 1201 X | OW | −177 | 277 | −288 | 27 |
| 1202 X | OW | −128 | 556 | 221 | 32 |
| 1203 X | OW | −348 | 406 | 29 | 38 |
| 1204 X | OW | −269 | 371 | 166 | 29 |
| 1205 X | OW | −233 | 546 | −169 | 32 |
| 1206 X | OW | −11 | 527 | 534 | 29 |
| 1207 X | OW | −241 | 439 | −137 | 31 |
| 1208 X | OW | −58 | 454 | 236 | 29 |
| 1209 X | OW | −239 | 381 | −438 | 27 |
| 1210 X | OW | 150 | 628 | 741 | 38 |
| 1211 X | OW | −96 | 256 | 406 | 26 |
| 1212 X | OW | 349 | 489 | 249 | 26 |
| 1213 X | OW | 110 | 418 | 851 | 26 |
| 1214 X | OW | 244 | 596 | 295 | 26 |
| 1215 X | OW | −140 | 453 | −425 | 28 |
| 1216 X | OW | 28 | 440 | −326 | 27 |
| 1217 X | OW | −160 | 537 | 210 | 25 |
| 1218 X | OW | −76 | 325 | −141 | 30 |
| 1219 X | OW | 80 | 456 | −91 | 32 |
| 1220 X | OW | 36 | 263 | 115 | 39 |
| 1221 X | OW | 194 | 731 | 277 | 25 |
| 1222 X | OW | 220 | 587 | 240 | 28 |
| 1223 X | OW | 128 | 412 | 393 | 30 |
| 1224 X | OW | −74 | 370 | −345 | 40 |
| 1225 X | OW | −337 | 381 | −277 | 33 |
| 1226 X | OW | 245 | 546 | 642 | 29 |
| 1227 X | OW | −100 | 660 | −56 | 24 |
| 1228 X | OW | 113 | 707 | 214 | 32 |
| 1229 X | OW | −319 | 479 | −37 | 29 |
| 1230 X | OW | −127 | 471 | −101 | 28 |
| 1231 X | OW | −166 | 430 | −136 | 43 |
| 1232 X | OW | 117 | 369 | −315 | 40 |
| 1233 X | OW | −21 | 421 | −197 | 27 |
| 1234 X | OW | −272 | 480 | 174 | 27 |
| 1235 X | OW | −51 | 348 | −53 | 30 |
| 1236 X | OW | 175 | 526 | 439 | 25 |
| 1237 X | OW | −69 | 310 | 208 | 31 |
| 1238 X | OW | −75 | 312 | 159 | 29 |
| 1239 X | OW | −91 | 686 | −65 | 31 |
| 1240 X | OW | −324 | 398 | 54 | 29 |
| 1241 X | OW | −174 | 524 | −38 | 31 |
| 1242 X | OW | 152 | 299 | 743 | 25 |
| 1243 X | OW | −83 | 248 | −210 | 26 |
| 1244 X | OW | −103 | 436 | −3 | 23 |
| 1245 X | OW | −119 | 458 | −141 | 37 |
| 1246 X | OW | −97 | 634 | −184 | 31 |
| 1247 X | OW | −164 | 483 | −148 | 25 |
| 1248 X | OW | 147 | 450 | 217 | 37 |
| 1249 X | OW | 86 | 375 | 52 | 26 |
| 1250 X | OW | −311 | 567 | −302 | 31 |
| 1251 X | OW | 199 | 340 | 528 | 31 |
| 1252 X | OW | 39 | 294 | 492 | 34 |
| 1253 X | OW | 106 | 396 | −78 | 25 |
| 1254 X | OW | 385 | 483 | 262 | 29 |
| 1255 X | OW | −228 | 759 | −46 | 34 |
| 1256 X | OW | 60 | 615 | −30 | 44 |
| 1257 X | OW | 164 | 489 | 552 | 27 |
| 1258 X | OW | −85 | 392 | 180 | 28 |
| 1259 X | OW | −19 | 257 | −232 | 27 |
| 1260 X | OW | −142 | 578 | 6 | 24 |
| 1261 X | OW | 49 | 330 | 725 | 24 |
| 1262 X | OW | −33 | 445 | 220 | 25 |
| 1263 X | OW | 81 | 452 | −119 | 28 |
| 1264 X | OW | −86 | 584 | −317 | 30 |
| 1265 X | OW | −360 | 406 | −149 | 27 |
| 1266 X | OW | −57 | 246 | 122 | 32 |
| 1267 X | OW | 53 | 548 | 487 | 26 |
| 1268 X | OW | 307 | 406 | 286 | 27 |
| 1269 X | OW | 60 | 396 | −227 | 22 |
| 1270 X | OW | 349 | 496 | 603 | 32 |
| 1271 X | OW | 104 | 439 | 407 | 31 |
| 1272 X | OW | 121 | 430 | 129 | 31 |
| 1273 X | OW | 91 | 361 | 412 | 28 |
| 1274 X | OW | 188 | 631 | 269 | 29 |
| 1275 X | OW | −332 | 481 | −398 | 61 |
| 1276 X | OW | 125 | 329 | 766 | 28 |
| 1277 X | OW | 294 | 589 | 437 | 28 |
| 1278 X | OW | −192 | 637 | 241 | 57 |
| 1279 X | OW | 28 | 335 | 653 | 26 |
| 1280 X | OW | 146 | 251 | −49 | 28 |
| 1281 X | OW | −38 | 704 | 111 | 27 |
| 1282 X | OW | −240 | 367 | 168 | 26 |
| 1283 X | OW | 233 | 554 | 569 | 33 |
| 1284 X | OW | −48 | 290 | −85 | 29 |
| 1285 X | OW | 174 | 436 | 537 | 34 |
| 1286 X | OW | −237 | 435 | 198 | 35 |
| 1287 X | OW | 75 | 489 | −57 | 30 |
| 1288 X | OW | −8 | 178 | 28 | 37 |
| 1289 X | OW | 165 | 699 | 471 | 29 |
| 1290 X | OW | −227 | 224 | −98 | 39 |
| 1291 X | OW | −170 | 515 | −447 | 35 |
| 1292 X | OW | −202 | 284 | −294 | 27 |
| 1293 X | OW | 60 | 357 | 392 | 30 |
| 1294 X | OW | 41 | 516 | 230 | 35 |
| 1295 X | OW | 41 | 614 | 354 | 36 |
| 1296 X | OW | −214 | 619 | 123 | 24 |
| 1297 X | OW | 45 | 312 | 606 | 32 |
| 1298 X | OW | 74 | 399 | −9 | 30 |
| 1299 X | OW | −40 | 235 | 38 | 26 |
| 1300 X | OW | 350 | 516 | 769 | 34 |
| 1301 X | OW | 201 | 692 | 246 | 26 |
| 1302 X | OW | 196 | 552 | 451 | 30 |
| 1303 X | OW | 266 | 367 | 234 | 29 |
| 1304 X | OW | 307 | 398 | 711 | 28 |
| 1305 X | OW | −79 | 327 | −41 | 34 |
| 1306 X | OW | −245 | 542 | −239 | 37 |
| 1307 X | OW | 70 | 367 | 740 | 26 |
| 1308 X | OW | 240 | 483 | 520 | 34 |
| 1309 X | OW | −228 | 461 | −140 | 35 |
| 1310 X | OW | 104 | 461 | −28 | 27 |
| 1311 X | OW | −299 | 700 | −8 | 26 |
| 1312 X | OW | −75 | 447 | 204 | 28 |
| 1313 X | OW | 327 | 345 | 566 | 29 |
| 1314 X | OW | −79 | 495 | 465 | 44 |
| 1315 X | OW | −23 | 541 | 173 | 32 |
| 1316 X | OW | 47 | 695 | 242 | 29 |
| 1317 X | OW | 32 | 448 | 767 | 30 |
| 1318 X | OW | 283 | 662 | 447 | 27 |
| 1319 X | OW | −241 | 410 | −314 | 33 |
| 1320 X | OW | 147 | 443 | 394 | 30 |
| 1321 X | OW | −188 | 635 | 128 | 30 |
| 1322 X | OW | −6 | 607 | −185 | 33 |
| 1323 X | OW | −361 | 413 | 0 | 31 |
| 1324 X | OW | 212 | 616 | 275 | 31 |
| 1325 X | OW | −362 | 291 | −66 | 44 |
| 1326 X | OW | 23 | 662 | 69 | 28 |
| 1327 X | OW | 11 | 573 | −292 | 30 |
| 1328 X | OW | −99 | 499 | 102 | 74 |
| 1329 X | OW | −61 | 288 | −13 | 30 |
| 1330 X | OW | −330 | 498 | −186 | 22 |
| 1331 X | OW | 116 | 477 | 73 | 29 |
| 1332 X | OW | −191 | 430 | −1 | 29 |
| 1333 X | OW | −24 | 404 | −59 | 34 |
| 1334 X | OW | −81 | 442 | 344 | 27 |
| 1335 X | OW | 9 | 683 | 61 | 41 |
| 1336 X | OW | −6 | 219 | 400 | 33 |
| 1337 X | OW | −38 | 274 | −48 | 45 |
| 1338 X | OW | 152 | 406 | 227 | 29 |
| 1339 X | OW | −55 | 504 | 582 | 34 |
| 1340 X | OW | 256 | 315 | 706 | 39 |
| 1341 X | OW | 118 | 504 | 142 | 34 |
| 1342 X | OW | 12 | 496 | −186 | 30 |
| 1343 X | OW | 132 | 721 | 230 | 35 |

TABLE 1-continued

| | | | | | |
|---|---|---|---|---|---|
| 1344 X | OW | 175 | 544 | 389 | 27 |
| 1345 X | OW | −176 | 620 | 106 | 66 |
| 1346 X | OW | −99 | 252 | 514 | 36 |
| 1347 X | OW | 60 | 307 | 199 | 34 |
| 1348 X | OW | 375 | 437 | 307 | 30 |
| 1349 X | OW | 208 | 719 | 254 | 33 |
| 1350 X | OW | 139 | 425 | 212 | 25 |
| 1351 X | OW | 268 | 480 | 227 | 28 |
| 1352 X | OW | −23 | 247 | 283 | 32 |
| 1353 X | OW | −78 | 473 | −394 | 28 |
| 1354 X | OW | −15 | 539 | 509 | 34 |
| 1355 X | OW | −85 | 597 | −147 | 25 |
| 1356 X | OW | 41 | 299 | 171 | 31 |
| 1357 X | OW | −250 | 576 | −380 | 49 |
| 1358 X | OW | 213 | 313 | 256 | 33 |
| 1359 X | OW | −135 | 487 | 276 | 31 |
| 1360 X | OW | 319 | 394 | 343 | 25 |
| 1361 X | OW | 85 | 665 | 72 | 29 |
| 1362 X | OW | 161 | 362 | 512 | 32 |
| 1363 X | OW | −130 | 468 | 129 | 54 |
| 1364 X | OW | 222 | 539 | 811 | 42 |
| 1365 X | OW | −46 | 405 | −346 | 30 |
| 1366 X | OW | 332 | 704 | 344 | 28 |
| 1367 X | OW | 300 | 535 | 329 | 38 |
| 1368 X | OW | 14 | 241 | 130 | 32 |
| 1369 X | OW | 100 | 661 | 49 | 27 |
| 1370 X | OW | −118 | 458 | 359 | 59 |
| 1371 X | OW | 227 | 317 | 496 | 25 |
| 1372 X | OW | 367 | 468 | 634 | 30 |
| 1373 X | OW | −130 | 531 | 279 | 27 |
| 1374 X | OW | 7 | 524 | −171 | 34 |
| 1375 X | OW | 130 | 525 | 124 | 27 |
| 1376 X | OW | 247 | 528 | 789 | 33 |
| 1377 X | OW | 2 | 156 | 439 | 55 |
| 1378 X | OW | 158 | 237 | −70 | 29 |
| 1379 X | OW | 119 | 168 | 74 | 28 |
| 1380 X | OW | −66 | 610 | 424 | 38 |
| 1381 X | OW | 146 | 720 | 297 | 53 |
| 1382 X | OW | 73 | 600 | 104 | 28 |
| 1383 X | OW | 350 | 547 | 796 | 38 |
| 1384 X | OW | −69 | 651 | −53 | 29 |
| 1385 X | OW | −134 | 475 | 301 | 46 |
| 1386 X | OW | −308 | 542 | −372 | 30 |
| 1387 X | OW | 345 | 361 | 712 | 50 |
| END | | | | | |

```
<160> NUMBER OF SEQ ID NOS: 1

<210> SEQ ID NO 1
<211> LENGTH: 576
<212> TYPE: PRT
<213> ORGANISM: Hepatitis C virus
<220> FEATURE:
<221> NAME/KEY: VARIANT
<222> LOCATION: (335)
<223> OTHER INFORMATION: amino acids at 335, 344 and 550 may be
      threonine or valine at 335, valine or alanine at 344 and arginine
      or glutamine at 550

<400> SEQUENCE: 1

Ala Ser His His His His His Ser Tyr Thr Trp Thr Gly Ala Leu
 1               5                  10                  15

Ile Thr Pro Cys Ala Ala Glu Glu Ser Lys Leu Pro Ile Asn Ala Leu
                20                  25                  30

Ser Asn Ser Leu Leu Arg His His Asn Met Val Tyr Ala Thr Thr Ser
            35                  40                  45

Arg Ser Ala Gly Leu Arg Gln Lys Lys Val Thr Phe Asp Arg Leu Gln
    50                  55                  60

Val Leu Asp Asp His Tyr Arg Asp Val Leu Lys Glu Met Lys Ala Lys
65                  70                  75                  80

Ala Ser Thr Val Lys Ala Lys Leu Leu Ser Val Glu Glu Ala Cys Lys
                85                  90                  95

Leu Thr Pro Pro His Ser Ala Lys Ser Lys Phe Gly Tyr Gly Ala Lys
            100                 105                 110

Asp Val Arg Asn Leu Ser Ser Lys Ala Val Asn His Ile His Ser Val
        115                 120                 125

Trp Lys Asp Leu Leu Glu Asp Thr Val Thr Pro Ile Asp Thr Thr Ile
    130                 135                 140
```

```
Met Ala Lys Asn Glu Val Phe Cys Val Gln Pro Glu Lys Gly Gly Arg
145                 150                 155                 160

Lys Pro Ala Arg Leu Ile Val Phe Pro Asp Leu Gly Val Arg Val Cys
            165                 170                 175

Glu Lys Met Ala Leu Tyr Asp Val Ser Thr Leu Pro Gln Val Val
            180                 185                 190

Met Gly Ser Ser Tyr Gly Phe Gln Tyr Ser Pro Gly Gln Arg Val Glu
            195                 200                 205

Phe Leu Val Asn Thr Trp Lys Ser Lys Asn Pro Met Gly Phe Ser
    210                 215                 220

Tyr Asp Thr Arg Cys Phe Asp Ser Thr Val Thr Glu Asn Asp Ile Arg
225                 230                 235                 240

Val Glu Glu Ser Ile Tyr Gln Cys Cys Asp Leu Ala Pro Glu Ala Arg
                245                 250                 255

Gln Ala Ile Lys Ser Leu Thr Glu Arg Leu Tyr Ile Gly Gly Pro Leu
            260                 265                 270

Thr Asn Ser Lys Gly Gln Asn Cys Gly Tyr Arg Arg Cys Arg Ala Ser
            275                 280                 285

Gly Val Leu Thr Thr Ser Cys Gly Asn Thr Leu Thr Cys Tyr Leu Lys
    290                 295                 300

Ala Ser Ala Ala Cys Arg Ala Ala Lys Leu Gln Asp Cys Thr Met Leu
305                 310                 315                 320

Val Asn Gly Asp Asp Leu Val Val Ile Cys Glu Ser Ala Gly Xaa Gln
            325                 330                 335

Glu Asp Ala Ala Ser Leu Arg Xaa Phe Thr Glu Ala Met Thr Arg Tyr
            340                 345                 350

Ser Ala Pro Pro Gly Asp Pro Pro Gln Pro Glu Tyr Asp Leu Glu Leu
            355                 360                 365

Ile Thr Ser Cys Ser Ser Asn Val Ser Val Ala His Asp Ala Ser Gly
    370                 375                 380

Lys Arg Val Tyr Tyr Leu Thr Arg Asp Pro Thr Thr Pro Leu Ala Arg
385                 390                 395                 400

Ala Ala Trp Glu Thr Ala Arg His Thr Pro Val Asn Ser Trp Leu Gly
            405                 410                 415

Asn Ile Ile Met Tyr Ala Pro Thr Leu Trp Ala Arg Met Ile Leu Met
            420                 425                 430

Thr His Phe Phe Ser Ile Leu Leu Ala Gln Glu Gln Leu Glu Lys Ala
    435                 440                 445

Leu Asp Cys Gln Ile Tyr Gly Ala Cys Tyr Ser Ile Glu Pro Leu Asp
    450                 455                 460

Leu Pro Gln Ile Ile Glu Arg Leu His Gly Leu Ser Ala Phe Ser Leu
465                 470                 475                 480

His Ser Tyr Ser Pro Gly Glu Ile Asn Arg Val Ala Ser Cys Leu Arg
            485                 490                 495

Lys Leu Gly Val Pro Pro Leu Arg Val Trp Arg His Arg Ala Arg Ser
            500                 505                 510

Val Arg Ala Arg Leu Leu Ser Gln Gly Gly Arg Ala Ala Thr Cys Gly
    515                 520                 525

Lys Tyr Leu Phe Asn Trp Ala Val Lys Thr Lys Leu Lys Leu Thr Pro
    530                 535                 540
```

-continued

```
Ile Pro Ala Ala Ser Xaa Leu Asp Leu Ser Gly Trp Phe Val Ala Gly
545                 550                 555                 560

Tyr Ser Gly Gly Asp Ile Tyr His Ser Leu Ser Arg Ala Arg Pro Arg
                565                 570                 575
```

We claim:

1. A crystalline composition comprising an HCV NS5B polypeptide, which comprises the amino acid sequence of SEQ ID NO: 1, wherein said crystalline composition effectively diffracts x-rays for the determination of the atomic coordinates of the polypeptide to a resolution of greater than 4.0 Ångströms.

2. The composition of claim 1, wherein the HCV NS5B polypeptide comprises a valine at position 335, an alanine at position 344, and a glutamine at position 550.

3. The crystalline composition of claim 1, wherein said crystalline composition effectively diffracts x-rays for the determination of the atomic coordinates of the polypeptide to a resolution of greater than 2.8 Ångströms.

4. The crystalline composition of claim 1, wherein said crystalline composition effectively diffracts x-rays for the determination of the atomic coordinates of the polypeptide to a resolution of greater than 2.2 Ångströms.

5. A method for preparing a crystalline composition which comprises an HCV NS5B polypeptide, comprising the steps of allowing the formation of a crystal of a purified and stabilized HCV NS5B polypeptide comprising the amino acid sequence of SEQ ID NO: 1 in a crystallization solution which comprises a precipitant, a protein stabilizing agent and a salt under conditions in which crystallization occurs and wherein said crystalline composition effectively diffracts x-rays for the determination of the atomic coordinates of the polypeptide to a resolution of greater than 4.0 Ångströms.

6. The method of claim 5, wherein the HCV NS5B is stabilized with glycerol.

7. The method of claim 5, wherein the HCV NS5B polypeptide is purified from a preparation comprising the HCV NS5B by cation exchange chromatography before the step of allowing the formation of a crystal.

8. The method of claim 7, wherein the preparation comprises glycine.

9. The method of claim 5, wherein the crystal forms from a crystallization method selected from microbatch and vapor diffusion.

10. The method of claim 5, wherein the protein stabilizing agent is glycerol.

11. The method of claim 10, wherein the concentration of the glycerol is about 2 to 20% (volume/volume).

12. The method of claim 10, wherein the concentration of the glycerol is about 10% (volume/volume).

13. The method of claim 5, wherein the precipitant is polyethylene glycol.

14. The method of claim 13, wherein the molecular weight of the polyethylene glycol is 1000 to 20,000 daltons.

15. The method of claim 13, wherein the molecular weight of the polyethylene glycol is 4000 to 5000 daltons.

16. A crystal comprising an HCV NS5B polypeptide which is prepared according to the method of claim 5.

17. A method for preparing a crystalline composition which comprises an HCV NS5B polypeptide, comprising the steps of allowing the formation of a crystal of a purified and stabilized HCV NS5B polypeptide comprising the amino acid sequence of SEQ ID NO: 1 in a crystallization solution which comprises a precipitant, a protein stabilizing agent and a salt under conditions in which crystallization occurs and wherein said crystalline composition effectively diffracts x-rays for the determination of the atomic coordinates of the polypeptide to a resolution of greater than 2.8 Ångströms.

18. The method of claim 17, wherein the HCV NS5B polypeptide is purified from a preparation comprising the HCV NS5B by cation exchange chromatography before the step of allowing the formation of a crystal.

19. The method of claim 18, wherein the preparation comprises glycine.

20. The method of claim 17, wherein the crystal forms from a crystallization method selected from microbatch and vapor diffusion.

21. The method of claim 17, wherein the protein stabilizing agent is glycerol.

22. The method of claim 21, wherein the concentration of the glycerol is about 2 to 20% (volume/volume).

23. The method of claim 21, wherein the concentration of the glycerol is about 10% (volume/volume).

24. The method of claim 17, wherein the precipitant is polyethylene glycol.

25. The method of claim 24, wherein the molecular weight of the polyethylene glycol is 1000 to 20,000 daltons.

26. The method of claim 24, wherein the molecular weight of the polyethylene glycol is 4000 to 5000 daltons.

27. A crystal comprising an HCV NS5B polypeptide which is prepared according to the method of claim 17.

28. A method for preparing a crystalline composition which comprises an HCV NS5B polypeptide, comprising the steps of allowing the formation of a crystal of a purified and stabilized HCV NS5B polypeptide comprising the amino acid sequence of SEQ ID NO: 1 in a crystallization solution which comprises a precipitant, a protein stabilizing agent and a salt under conditions in which crystallization occurs and wherein said crystalline composition effectively diffracts x-rays for the determination of the atomic coordinates of the polypeptide to a resolution of greater than 2.2 Ångströms.

29. The method of claim 28, wherein the HCV NS5B polypeptide is purified from a preparation comprising the HCV NS5B by cation exchange chromatography before the step of allowing the formation of a crystal.

30. The method of claim 29, wherein the preparation comprises glycine.

31. The method of claim 28, wherein the crystal forms from a crystallization method selected from microbatch and vapor diffusion.

32. The method of claim 28, wherein the protein stabilizing agent is glycerol.

33. The method of claim 32, wherein the concentration of the glycerol is about 2 to 20% (volume/volume).

34. The method of claim 32, wherein the concentration of the glycerol is about 10% (volume/volume).

35. The method of claim 28, wherein the precipitant is polyethylene glycol.

36. The method of claim 35, wherein the molecular weight of the polyethylene glycol is 1000 to 20,000 daltons.

37. The method of claim 35, wherein the molecular weight of the polyethylene glycol is 4000 to 5000 daltons.

38. A crystal comprising an HCV NS5B polypeptide which is prepared according to the method of claim 28.

* * * * *